(12) United States Patent
Zhu et al.

(10) Patent No.: US 9,518,268 B2
(45) Date of Patent: Dec. 13, 2016

(54) DROUGHT TOLERANT TRANSGENIC PLANTS AND METHOD OF MAKING SAME

(71) Applicant: PURDUE RESEARCH FOUNDATION, West Lafayette, IN (US)

(72) Inventors: Jian-Kang Zhu, West Lafayette, IN (US); Yang Zhao, West Lafayette, IN (US); Zhulong Chan, Hubei Province (CN)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 92 days.

(21) Appl. No.: 14/335,017

(22) Filed: Jul. 18, 2014

(65) Prior Publication Data

US 2015/0074844 A1    Mar. 12, 2015

Related U.S. Application Data

(60) Provisional application No. 61/856,198, filed on Jul. 19, 2013.

(51) Int. Cl.
| | | |
|---|---|---|
| A01H 5/00 | (2006.01) | |
| A01H 1/00 | (2006.01) | |
| C07K 14/415 | (2006.01) | |
| C12N 15/82 | (2006.01) | |
| C12N 15/00 | (2006.01) | |

(52) U.S. Cl.
CPC ......... *C12N 15/8273* (2013.01); *C07K 14/415* (2013.01)

(58) Field of Classification Search
None
See application file for complete search history.

(56) References Cited

U.S. PATENT DOCUMENTS

2011/0271408 A1* 11/2011 Cutler .................... A01N 25/00
800/300

OTHER PUBLICATIONS

Fujii, H. et al. (2009) In vitro reconstitution of an abscisic acid signalling pathway. *Nature*, vol. 462, No. 3, pp. 660-664.

Hao, Qi et al. (2011) The molecular basis of ABA-independent inhibition of PP2Cs by a subclass of PYL proteins. *MolCell*, vol. 42, pp. 662-672.
He, Yuan et al. Identification and Characterization of ABA Receptors in *Oryza sativa*. Plos One, Apr. 2014, vol. 9, No. 4, pp. 1-8.
Hsieh, Tsai-Hung et al. (2002) Tomato Plants Ectopically Expressing *Arabidopsis* CBF1 Show Enhanced Resistance to Water Deficit Stress. *Plant Physiology* vol. 130, pp. 618-626.
Jaglo-Ottosen, Kirsten R. et al. (1998) *Arabidopsis* CBF1 overexpression induces COR genes and enhances freezing tolerance. *Science*, vol. 280, pp. 104-106.
Kuhn, Josef M. et al. (2006) The protein phosphatase AtPP2CA negatively regulates abscisic acid signal transduction in *Arabidopsis*, and effects of abh1 on AtPP2CA mRNA. *Plant Physiol*, vol. 140, pp. 127-139.
Liu, Qiang et al. (1998) Two transcription factors, DREB1 and DREB2, with an EREBP/AP2 DNA binding domain separate two cellular signal transduction pathways in drought- and low-temperature-responsive gene expression, respectively, in *Arabidopsis*. *Plant Cell*, vol. 10, pp. 1391-1406.
Ma, Qibin et al. (2009a) Enhanced tolerance to chilling stress in OsMYB3R-2 transgenic rice is mediated by alteration in cell cycle and ectopic expression of stress genes. *Plant Physiol*, vol. 150, pp. 244-256.
Ma, Yue et al. (2009b) Regulators of PP2C phosphatase activity function as abscisic acid sensors. *Science*, vol. 324, pp. 1064-1068.
Park, Sang-Youl et al. (2009) Abscisic acid inhibits type 2C protein phosphatases via the PYR/PYL family of START proteins. *Science*, vol. 324, pp. 1068-1071.
Yin, Ping et al. (2009) Structural insights into the mechanism of abscisic acid signaling by PYL proteins. *Nat Struct Mol Biol*, vol. 16, pp. 1230-1236.

* cited by examiner

*Primary Examiner* — Phuong Bui
(74) *Attorney, Agent, or Firm* — Marianne Fuierer; Moore & Van Allen, PLLC

(57) ABSTRACT

Embodiments of the present invention relate generally to drought tolerant transgenic plants and methods of creating the drought tolerant transgenic plants. In one embodiment, plants are transformed such that a PYL polypeptide is overexpressed in the plant. In an embodiment, the plant is transformed with a cassette or vector that comprises a polynucleotide encoding for one or more of the PYL polypeptides, which may be under the control of an inducible or constitutive promoter. In embodiments, overexpression of PYL13 results in plants having increased drought tolerance, such as a decreased transpiration rate, a decreased stomatal conductance, an increased photosynthetic rate, accelerated stress responsive gene expression, and increased water use efficiency, and/or an increased survival rate compared to a control plant. In some embodiments, other PYL proteins having the single point mutations identified in PYL13 are expressed in the plant.

13 Claims, 16 Drawing Sheets

FIG. 11A

| Plasmids | Forward primers | Reverse primers |
|---|---|---|
| pHBT-HAI1 | CGGCTCCCTCTCCCCTTGCTCGTCGTGGATCCATGGCTGAGATTTGTTACGAAG SEQ ID NO: 74 | GTAGTCTGGAACGTCGTATGGGTAAGGCCTCGTGTCTCGTAGATCAAC SEQ ID NO: 75 |
| pHBT-HAI2 | CGGCTCCCTCTCCCCTTGCTCGTCGTGGATCCATGGGCGGATCCGGATATTGTTATGAAG SEQ ID NO: 76 | GTAGTCTGGAACGTCGTATGGGTAAGGCCTAGCAAGCTAGCTCTTCTTC SEQ ID NO: 77 |
| pHBT-HAI3 | CGGCTCCCTCTCCCCTTGCTCGTCGTGGATCCATGGGCGGATCCGAGATATTGTTACGAAG SEQ ID NO: 78 | GTAGTCTGGAACGTCGTATGGGTAAGGCCTTCTTCTGAGATCAATCACAAC SEQ ID NO: 79 |
| pHBT-AHG1 | CGGCTCCCTCTCCCCTTGCTCGTCGTGGATCCATGGCTCATGAATGAAAATCTACAGAAC SEQ ID NO: 80 | GTAGTCTGGAACGTCGTATGGGTAAGGCCTCTGAGAGCTATTCTTGAGATC SEQ ID NO: 81 |
| pGEX-6P1-PYL13 | GAAGTTCTGTTCCAGGGACCCCTGGGATCCATGGAGAAAGTTCTAAGCAAAAACG SEQ ID NO: 82 | ATGCGGCCGCTCGAGTCGACCCGGGAATTCTTACTTCATCATTTTCTTTGTG SEQ ID NO: 83 |
| pGEX-6P1-PYL2 | GAAGTTCTGTTCCAGGGGACCCCTGGGATCCATGAGTGAGCTCATGAAGCTCATCCCCGCCGTG SEQ ID NO: 84 | ATGCGGCCGCTCGAGTCGACCCGGGAATTCTTATTCATCATCATGACAGGTGC SEQ ID NO: 85 |
| pGEX-6P1-PP2CA | GAAGTTCTGTTCCAGGGACCCCTGGGATCCATGGCTGGGATTGTTGCG SEQ ID NO: 86 | GTCAGTCACGATGCGGCCGCTCGAGTCGACTTAAGACGACGCTTGATTATTCCT SEQ ID NO: 87 |
| pGEX-6P1-ABI1 | GAAGTTCTGTTCCAGGGACCCCTGGGATCCATGGAGGAGAAGTATCTCCGGC SEQ ID NO: 88 | ATGCGGCCGCTCGAGTCGACCCGGGAATTCTCAGTTCAAGGGTTGCTCTTG SEQ ID NO: 89 |
| pGEX-6P1-ABI2 | GAAGTTCTGTTCCAGGGACCCCTGGGATCCATGGACGAAGTTTCCTGC SEQ ID NO: 90 | ATGCGGCCGCTCGAGTCGACCCGGGAATTCTCAATTCAAGGATTTGCTCTTG SEQ ID NO: 91 |
| pGEX-6P1-AHG1 | GAAGTTCTGTTCCAGGGACCCCTGGGATCCATGGAGACTGAAAATCTACAGAAC SEQ ID NO: 92 | ATGCGGGCCGCTCGAGTCGACCCGGGAATTCTTACTGAGTACTATTCTTGAG SEQ ID NO: 93 |
| pET28a-PYL13 | ATCGGATCCATGGAAAAGTTCTAAGCAAAAACG SEQ ID NO: 94 | ATGAATTCTTACTTCATCATTTCTTTGTGAGC SEQ ID NO: 95 |
| pET28a-PYL2 | ATCGGATCCATGAGTCTCATCCCCGGC SEQ ID NO: 96 | ATCGAATTCTTATTCATCATCATGACATAG SEQ ID NO: 97 |
| pET28a-PYR1 | ATCGGATCCTTCGGAGTTAACAC SEQ ID NO: 98 | ATCGAATTCTCAGTCACCTGAGAACCAC SEQ ID NO: 99 |
| pHBT-nLUC | CGGCTCCCTCTCCCCTTGCTCGTCGTGGATCCGACTCTAGACTGCAGACTCGAGATCTCGTACGCGTCC SEQ ID NO: 100 | AGAAACTTATTGCCAAATGTTGAACGATTCATCATCCTTGTCAATCCTTGTCAATCAAGGSEQ ID NO: 101 |
| pHBT-cLUC | AGCTCTCGGCTCCTCTCCCCTTGCTCCCGTATGTCGGTTATGTAAACAATCC SEQ ID NO: 102 | TTTATTGCCAAATGTTTGAACGATCTGCAGTCTAGAGTCGACGGATCCGCCGGGACGGTAC SEQ ID NO: 103 |
| nLUC-PYR1 | CGTGGATCCATGCCTTCGGAGTTAACAC SEQ ID NO: 104 | TCCGTGACCGTCACCTGAGAACCAC SEQ ID NO: 105 |
| nLUC-PYL1 | CGTGGATCCATGGCGGAATTCAGAGTCCTC SEQ ID NO: 106 | TCCGTGACCGTCAACCTAACCTGAGAAGAGTTGTTG SEQ ID NO: 107 |
| nLUC-PYL2 | CGTGGATCCATGAGTCTCATCCCCGGC SEQ ID NO: 108 | TCCGTGATTCATCATCATGACATAG SEQ ID NO: 109 |
| nLUC-PYL3 | ATCGGATCCATGCCTTCGGAGTTAACACCTTGCTCCGTTCACCGTC SEQ ID NO: 110 | TCCGTGGAGGTGGAGAAGCCGTGgaaatg SEQ ID NO: 111 |
| nLUC-PYL4 | CGTGGATCCATGCTTGCCGTTCACCGTC SEQ ID NO: 112 | TCCGTGACAGAGACATCTCTTCTTGCTCTC SEQ ID NO: 113 |
| nLUC-PYL5 | CGTGGATCCATGAGGTCACCGGTGCAACTC SEQ ID NO: 114 | TCCGTGATTGCCGGTTGGTACTTCgag SEQ ID NO: 115 |
| nLUC-PYL6 | CGTGGATCCATGCCAAGCTGCGATACAGTTTC SEQ ID NO: 116 | TCCGTCGACGGAATTTAGAAGTGTTCTCGG SEQ ID NO: 117 |
| nLUC-PYL7 | CGTGGATCCATGGAGATGATCGGAGGAG SEQ ID NO: 118 | TCCGTGAAAGGTTGGTTTCTGTATG SEQ ID NO: 119 |
| nLUC-PYL8 | CGTGGATCCATGGAAGTAACGGGGATTG SEQ ID NO: 120 | TCCGTGAGACTTCTGATTCTGTCGTGTC SEQ ID NO: 121 |
| nLUC-PYL9 | CGTGGATCCATGATGGACGGCGTTGAAG SEQ ID NO: 122 | TCCGTGAGTGAGTAATGTCGTCCTGAG SEQ ID NO: 123 |
| nLUC-PYL10 | CGTGGATCCATGAACGGTGACGAAACAAAG SEQ ID NO: 124 | TCCGTGATATCTTCTTCCCATAGATTC SEQ ID NO: 125 |
| nLUC-PYL11 | CGTGGATCCATGGAAAACTTCTCAAAAATATC SEQ ID NO: 126 | TCCGTGACAACTTTAGATGAGCCAC SEQ ID NO: 127 |
| nLUC-PYL12 | CGTGGATCCATGGAAAACATCTCAAGAAC SEQ ID NO: 128 | TCCGTGAAGTGAGTCCATCATtcc SEQ ID NO: 129 |
| nLUC-PYL13 | CGTGGATCCATGGAAAAGTTCTAAGCAAAAACG SEQ ID NO: 130 | TCCGTGACTTCATCATTTTCTTTGTGAGC SEQ ID NO: 131 |
| cLUC-PYL13 | CGTGGATCCATGGAAAAGTTCTAAGCAAAAACG SEQ ID NO: 132 | TCCGTGACttaTTCATCATTTCTTTGTGAGC SEQ ID NO: 133 |

*FIG. 11B*

SEQUENCE LISTING

```
<160> NUMBER OF SEQ ID NOS: 167

<210> SEQ ID NO 1
<211> LENGTH: 164
<212> TYPE: PRT
<213> ORGANISM: Arabidopsis thaliana

<400> SEQUENCE: 1

Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
            20                  25                  30

Lys Pro Gln Ala Tyr Gln Arg Phe Val Lys Ser Cys Thr Met Arg Ser
        35                  40                  45

Gly Gly Gly Gly Gly Lys Gly Gly Glu Gly Lys Gly Ser Val Arg Asp
    50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
            85                  90                  95

Gly Asn His Arg Leu Val Asn Tyr Lys Ser Lys Thr Lys Val Val Ala
            100                 105                 110

Ser Pro Glu Asp Met Ala Lys Lys Thr Val Val Val Glu Ser Tyr Val
        115                 120                 125
```

```
Val Asp Val Pro Glu Gly Thr Ser Glu Glu Asp Thr Ile Phe Phe Val
    130                 135                 140

Asp Asn Ile Ile Arg Tyr Asn Leu Thr Ser Leu Ala Lys Leu Thr Lys
145                 150                 155                 160

Lys Met Met Lys

<210> SEQ ID NO 2
<211> LENGTH: 30
<212> TYPE: DNA
<213> ORGANISM: Artificial Sequence
<220> FEATURE:
<223> OTHER INFORMATION: pCAMBIA99-1-PYL13 Forward Primer

<400> SEQUENCE: 2
gcgaattcat ggaaagttct aagcaaaaac                                   30

<210> SEQ ID NO 3
<211> LENGTH: 28
<212> TYPE: DNA
<213> ORGANISM: Artificial Sequence
<220> FEATURE:
<223> OTHER INFORMATION: pCAMBIA99-1-PYL13 Reverse Primer

<400> SEQUENCE: 3
gcgtcgactt acttcatcat tttctttg                                     28

<210> SEQ ID NO 4
<211> LENGTH: 33
<212> TYPE: DNA
<213> ORGANISM: Artificial Sequence
<220> FEATURE:
<223> OTHER INFORMATION: ProPYL13: PYL13-HA-YFP Forward Primer

<400> SEQUENCE: 4
gcctgtcgac cacttactta ccctaatgcg tgt                               33

<210> SEQ ID NO 5
<211> LENGTH: 33
<212> TYPE: DNA
<213> ORGANISM: Artificial Sequence
<220> FEATURE:
<223> OTHER INFORMATION: ProPYL13: PYL13-HA-YFP Reverse Primer

<400> SEQUENCE: 5
gcctgggccc cttcatcatt ttctttgtga gct                               33

<210> SEQ ID NO 6
<211> LENGTH: 31
<212> TYPE: DNA
<213> ORGANISM: Artificial Sequence
<220> FEATURE:
<223> OTHER INFORMATION: pHBT95-PYL13 Forward Primer

<400> SEQUENCE: 6
cgggatccat ggaaagttct aagcaaaaac g                                 31

<210> SEQ ID NO 7
<211> LENGTH: 35
<212> TYPE: DNA
<213> ORGANISM: Artificial Sequence
<220> FEATURE:
<223> OTHER INFORMATION: pHBT95-PYL13 Reverse Primer

<400> SEQUENCE: 7
gtcaaggcct ttacttcatc attttctttg tgagc                             35
```

<210> SEQ ID NO 8
<211> LENGTH: 37
<212> TYPE: DNA
<213> ORGANISM: Artificial Sequence
<220> FEATURE:
<223> OTHER INFORMATION: pHBT95-Q38K Forward Primer

<400> SEQUENCE: 8
caaaccacaa gcttataaac gtttcgtcaa aagttgc                                37

<210> SEQ ID NO 9
<211> LENGTH: 37
<212> TYPE: DNA
<213> ORGANISM: Artificial Sequence
<220> FEATURE:
<223> OTHER INFORMATION: pHBT95-Q38K Reverse Primer

<400> SEQUENCE: 9
cttttgacga aacgtttata agcttgtggt ttgtcga                                37

<210> SEQ ID NO 10
<211> LENGTH: 37
<212> TYPE: DNA
<213> ORGANISM: Artificial Sequence
<220> FEATURE:
<223> OTHER INFORMATION: pHBT95-F71L Forward Primer

<400> SEQUENCE: 10
gacgttagtc tccggcctcc cggcggattt cagcacg                                37

<210> SEQ ID NO 11
<211> LENGTH: 37
<212> TYPE: DNA
<213> ORGANISM: Artificial Sequence
<220> FEATURE:
<223> OTHER INFORMATION: pHBT95-F71L Reverse Primer

<400> SEQUENCE: 11
gctgaaatcc gccgggaggc cggagactaa cgtcacg                                37

<210> SEQ ID NO 12
<211> LENGTH: 37
<212> TYPE: DNA
<213> ORGANISM: Artificial Sequence
<220> FEATURE:
<223> OTHER INFORMATION: pHBT95-N98D Forward Primer

<400> SEQUENCE: 12
aagtattatt ggcggtgacc ataggcttgt taattac                                37

<210> SEQ ID NO 13
<211> LENGTH: 37
<212> TYPE: DNA
<213> ORGANISM: Artificial Sequence
<220> FEATURE:
<223> OTHER INFORMATION: pHBT95-N98D Reverse Primer

<400> SEQUENCE: 13
attaacaagc ctatggtcac cgccaataat acttacc                                37

<210> SEQ ID NO 14
<211> LENGTH: 38
<212> TYPE: DNA
<213> ORGANISM: Artificial Sequence
<220> FEATURE:

-continued

<223> OTHER INFORMATION: pHBT95-T135N Forward Primer

<400> SEQUENCE: 14
gatgtgccgg aaggaaatag cgaggaagat acaatatt                    38

<210> SEQ ID NO 15
<211> LENGTH: 38
<212> TYPE: DNA
<213> ORGANISM: Artificial Sequence
<220> FEATURE:
<223> OTHER INFORMATION: pHBT95-T135N Reverse Primer

<400> SEQUENCE: 15
attgtatctt cctcgctatt tccttccggc acatccac                    38

<210> SEQ ID NO 16
<211> LENGTH: 37
<212> TYPE: DNA
<213> ORGANISM: Artificial Sequence
<220> FEATURE:
<223> OTHER INFORMATION: pHBT95-Q38KF71L Forward Primer

<400> SEQUENCE: 16
caaaccacaa gcttataaac gtttcgtcaa aagttgc                     37

<210> SEQ ID NO 17
<211> LENGTH: 37
<212> TYPE: DNA
<213> ORGANISM: Artificial Sequence
<220> FEATURE:
<223> OTHER INFORMATION: pHBT95-Q38KF71L Reverse Primer

<400> SEQUENCE: 17
cttttgacga aacgtttata agcttgtggt ttgtcga                     37

<210> SEQ ID NO 18
<211> LENGTH: 37
<212> TYPE: DNA
<213> ORGANISM: Artificial Sequence
<220> FEATURE:
<223> OTHER INFORMATION: pHBT95-Q38KF71L Forward Primer

<400> SEQUENCE: 18
gacgttagtc tccggcctcc cggcggattt cagcacg                     37

<210> SEQ ID NO 19
<211> LENGTH: 37
<212> TYPE: DNA
<213> ORGANISM: Artificial Sequence
<220> FEATURE:
<223> OTHER INFORMATION: pHBT95-Q38KF71L Reverse Primer

<400> SEQUENCE: 19
gctgaaatcc gccgggaggc cggagactaa cgtcacg                     37

<210> SEQ ID NO 20
<211> LENGTH: 37
<212> TYPE: DNA
<213> ORGANISM: Artificial Sequence
<220> FEATURE:
<223> OTHER INFORMATION: pHBT95-Q38KN98D Forward Primer

<400> SEQUENCE: 20
caaaccacaa gcttataaac gtttcgtcaa aagttgc                     37

-continued

```
<210> SEQ ID NO 21
<211> LENGTH: 37
<212> TYPE: DNA
<213> ORGANISM: Artificial Sequence
<220> FEATURE:
<223> OTHER INFORMATION: pHBT95-Q38KN98D Reverse Primer

<400> SEQUENCE: 21
cttttgacga aacgtttata agcttgtggt ttgtcga                              37

<210> SEQ ID NO 22
<211> LENGTH: 37
<212> TYPE: DNA
<213> ORGANISM: Artificial Sequence
<220> FEATURE:
<223> OTHER INFORMATION: pHBT95-Q38KN98D Forward Primer

<400> SEQUENCE: 22
aagtattatt ggcggtgacc ataggcttgt taattac                              37

<210> SEQ ID NO 23
<211> LENGTH: 37
<212> TYPE: DNA
<213> ORGANISM: Artificial Sequence
<220> FEATURE:
<223> OTHER INFORMATION: pHBT95-Q38KN98D Reverse Primer

<400> SEQUENCE: 23
attaacaagc ctatggtcac cgccaataat acttacc                              37

<210> SEQ ID NO 24
<211> LENGTH: 37
<212> TYPE: DNA
<213> ORGANISM: Artificial Sequence
<220> FEATURE:
<223> OTHER INFORMATION: pHBT95-Q38KT135N Forward Primer

<400> SEQUENCE: 24
caaaccacaa gcttataaac gtttcgtcaa aagttgc                              37

<210> SEQ ID NO 25
<211> LENGTH: 37
<212> TYPE: DNA
<213> ORGANISM: Artificial Sequence
<220> FEATURE:
<223> OTHER INFORMATION: pHBT95-Q39KT135N Reverse Primer

<400> SEQUENCE: 25
cttttgacga aacgtttata agcttgtggt ttgtcga                              37

<210> SEQ ID NO 26
<211> LENGTH: 38
<212> TYPE: DNA
<213> ORGANISM: Artificial Sequence
<220> FEATURE:
<223> OTHER INFORMATION: pHBT95-Q38KT135N Forward Primer

<400> SEQUENCE: 26
gatgtgccgg aaggaaatag cgaggaagat acaatatt                             38

<210> SEQ ID NO 27
<211> LENGTH: 38
<212> TYPE: DNA
<213> ORGANISM: Artificial Sequence
<220> FEATURE:
<223> OTHER INFORMATION: pHBT95-Q38KT135N Reverse Primer
```

<400> SEQUENCE: 27
attgtatctt cctcgctatt tccttccggc acatccac                    38

<210> SEQ ID NO 28
<211> LENGTH: 37
<212> TYPE: DNA
<213> ORGANISM: Artificial Sequence
<220> FEATURE:
<223> OTHER INFORMATION: pHBT95-F71LN98D Forward Primer

<400> SEQUENCE: 28
gacgttagtc tccggcctcc cggcggattt cagcacg                     37

<210> SEQ ID NO 29
<211> LENGTH: 37
<212> TYPE: DNA
<213> ORGANISM: Artificial Sequence
<220> FEATURE:
<223> OTHER INFORMATION: pHBT95-F71LN98D Reverse Primer

<400> SEQUENCE: 29
gctgaaatcc gccgggaggc cggagactaa cgtcacg                     37

<210> SEQ ID NO 30
<211> LENGTH: 37
<212> TYPE: DNA
<213> ORGANISM: Artificial Sequence
<220> FEATURE:
<223> OTHER INFORMATION: pHBT95-F71LN98D Forward Primer

<400> SEQUENCE: 30
aagtattatt ggcggtgacc ataggcttgt taattac                     37

<210> SEQ ID NO 31
<211> LENGTH: 37
<212> TYPE: DNA
<213> ORGANISM: Artificial Sequence
<220> FEATURE:
<223> OTHER INFORMATION: pHBT95-F71LN98D Reverse Primer

<400> SEQUENCE: 31
attaacaagc ctatggtcac cgccaataat acttacc                     37

<210> SEQ ID NO 32
<211> LENGTH: 37
<212> TYPE: DNA
<213> ORGANISM: Artificial Sequence
<220> FEATURE:
<223> OTHER INFORMATION: pHBT95-F71LT135N Forward Primer

<400> SEQUENCE: 32
gacgttagtc tccggcctcc cggcggattt cagcacg                     37

<210> SEQ ID NO 33
<211> LENGTH: 37
<212> TYPE: DNA
<213> ORGANISM: Artificial Sequence
<220> FEATURE:
<223> OTHER INFORMATION: pHBT95-F71LT135N Reverse Primer

<400> SEQUENCE: 33
gctgaaatcc gccgggaggc cggagactaa cgtcacg                     37

<210> SEQ ID NO 34
<211> LENGTH: 38

```
<212> TYPE: DNA
<213> ORGANISM: Artificial Sequence
<220> FEATURE:
<223> OTHER INFORMATION: pHBT95-F71LT135N Forward Primer

<400> SEQUENCE: 34
gatgtgccgg aaggaaatag cgaggaagat acaatatt                              38

<210> SEQ ID NO 35
<211> LENGTH: 38
<212> TYPE: DNA
<213> ORGANISM: Artificial Sequence
<220> FEATURE:
<223> OTHER INFORMATION: pHBT95-F71LT135N Reverse Primer

<400> SEQUENCE: 35
attgtatctt cctcgctatt tccttccggc acatccac                              38

<210> SEQ ID NO 36
<211> LENGTH: 37
<212> TYPE: DNA
<213> ORGANISM: Artificial Sequence
<220> FEATURE:
<223> OTHER INFORMATION: pHBT95-N98DT135N Forward Primer

<400> SEQUENCE: 36
aagtattatt ggcggtgacc ataggcttgt taattac                               37

<210> SEQ ID NO 37
<211> LENGTH: 37
<212> TYPE: DNA
<213> ORGANISM: Artificial Sequence
<220> FEATURE:
<223> OTHER INFORMATION: pHBT95-N98DT135N Reverse Primer

<400> SEQUENCE: 37
attaacaagc ctatggtcac cgccaataat acttacc                               37

<210> SEQ ID NO 38
<211> LENGTH: 38
<212> TYPE: DNA
<213> ORGANISM: Artificial Sequence
<220> FEATURE:
<223> OTHER INFORMATION: pHBT95-N98DT135N Forward Primer

<400> SEQUENCE: 38
gatgtgccgg aaggaaatag cgaggaagat acaatatt                              38

<210> SEQ ID NO 39
<211> LENGTH: 38
<212> TYPE: DNA
<213> ORGANISM: Artificial Sequence
<220> FEATURE:
<223> OTHER INFORMATION: pHBT95-N98DT135N Reverse Primer

<400> SEQUENCE: 39
attgtatctt cctcgctatt tccttccggc acatccac                              38

<210> SEQ ID NO 40
<211> LENGTH: 37
<212> TYPE: DNA
<213> ORGANISM: Artificial Sequence
<220> FEATURE:
<223> OTHER INFORMATION: pHBT95-Q38KF71LN98D Forward Primer

<400> SEQUENCE: 40
```
caaaccacaa gcttataaac gtttcgtcaa aagttgc                                    37

<210> SEQ ID NO 41
<211> LENGTH: 37
<212> TYPE: DNA
<213> ORGANISM: Artificial Sequence
<220> FEATURE:
<223> OTHER INFORMATION: pHBT95-Q38KF71LN98D Reverse Primer

<400> SEQUENCE: 41
cttttgacga aacgtttata agcttgtggt ttgtcga                                    37

<210> SEQ ID NO 42
<211> LENGTH: 37
<212> TYPE: DNA
<213> ORGANISM: Artificial Sequence
<220> FEATURE:
<223> OTHER INFORMATION: pHBT95-Q38KF71LN98D Forward Primer

<400> SEQUENCE: 42
gacgttagtc tccggcctcc cggcggattt cagcacg                                    37

<210> SEQ ID NO 43
<211> LENGTH: 37
<212> TYPE: DNA
<213> ORGANISM: Artificial Sequence
<220> FEATURE:
<223> OTHER INFORMATION: pHBT95-Q38KF71LN98D Reverse Primer

<400> SEQUENCE: 43
gctgaaatcc gccgggaggc cggagactaa cgtcacg                                    37

<210> SEQ ID NO 44
<211> LENGTH: 37
<212> TYPE: DNA
<213> ORGANISM: Artificial Sequence
<220> FEATURE:
<223> OTHER INFORMATION: pHBT95-Q38KF71LN98D Forward Primer

<400> SEQUENCE: 44
aagtattatt ggcggtgacc ataggcttgt taattac                                    37

<210> SEQ ID NO 45
<211> LENGTH: 37
<212> TYPE: DNA
<213> ORGANISM: Artificial Sequence
<220> FEATURE:
<223> OTHER INFORMATION: pHBT95-Q38KF71LN98D Reverse Primer

<400> SEQUENCE: 45
attaacaagc ctatggtcac cgccaataat acttacc                                    37

<210> SEQ ID NO 46
<211> LENGTH: 37
<212> TYPE: DNA
<213> ORGANISM: Artificial Sequence
<220> FEATURE:
<223> OTHER INFORMATION: pHBT95-Q38KF71LT135N Forward Primer

<400> SEQUENCE: 46
caaaccacaa gcttataaac gtttcgtcaa aagttgc                                    37

<210> SEQ ID NO 47
<211> LENGTH: 37
<212> TYPE: DNA
<213> ORGANISM: Artificial Sequence
<220> FEATURE:
<223> OTHER INFORMATION: pHBT95-Q38KF71LT135N Reverse Primer

<400> SEQUENCE: 47
cttttgacga aacgtttata agcttgtggt ttgtcga   37

<210> SEQ ID NO 48
<211> LENGTH: 37
<212> TYPE: DNA
<213> ORGANISM: Artificial Sequence
<220> FEATURE:
<223> OTHER INFORMATION: pHBT95-Q38KF71LT135N Forward Primer

<400> SEQUENCE: 48
gacgttagtc tccggcctcc cggcggattt cagcacg   37

<210> SEQ ID NO 49
<211> LENGTH: 37
<212> TYPE: DNA
<213> ORGANISM: Artificial Sequence
<220> FEATURE:
<223> OTHER INFORMATION: pHBT95-Q38KF71LT135N Reverse Primer

<400> SEQUENCE: 49
gctgaaatcc gccgggaggc cggagactaa cgtcacg   37

<210> SEQ ID NO 50
<211> LENGTH: 38
<212> TYPE: DNA
<213> ORGANISM: Artificial Sequence
<220> FEATURE:
<223> OTHER INFORMATION: pHBT95-Q38KF71LT135N Forward Primer

<400> SEQUENCE: 50
gatgtgccgg aaggaaatag cgaggaagat acaatatt   38

<210> SEQ ID NO 51
<211> LENGTH: 38
<212> TYPE: DNA
<213> ORGANISM: Artificial Sequence
<220> FEATURE:
<223> OTHER INFORMATION: pHBT95-Q38KF71LT135N Reverse Primer

<400> SEQUENCE: 51
attgtatctt cctcgctatt tccttccggc acatccac   38

<210> SEQ ID NO 52
<211> LENGTH: 37
<212> TYPE: DNA
<213> ORGANISM: Artificial Sequence
<220> FEATURE:
<223> OTHER INFORMATION: pHBT95-F71LN98DT135N Forward Primer

<400> SEQUENCE: 52
gacgttagtc tccggcctcc cggcggattt cagcacg   37

<210> SEQ ID NO 53
<211> LENGTH: 37
<212> TYPE: DNA
<213> ORGANISM: Artificial Sequence
<220> FEATURE:
<223> OTHER INFORMATION: pHBT95-F71LN98DT135N Reverse Primer

<400> SEQUENCE: 53
gctgaaatcc gccgggaggc cggagactaa cgtcacg   37

<210> SEQ ID NO 54
<211> LENGTH: 37
<212> TYPE: DNA
<213> ORGANISM: Artificial Sequence
<220> FEATURE:
<223> OTHER INFORMATION: pHBT95-F71LN98DT135N Forward Primer

<400> SEQUENCE: 54
aagtattatt ggcggtgacc ataggcttgt taattac     37

<210> SEQ ID NO 55
<211> LENGTH: 37
<212> TYPE: DNA
<213> ORGANISM: Artificial Sequence
<220> FEATURE:
<223> OTHER INFORMATION: pHBT95-F71LN98DT135N Reverse Primer

<400> SEQUENCE: 55
attaacaagc ctatggtcac cgccaataat acttacc     37

<210> SEQ ID NO 56
<211> LENGTH: 38
<212> TYPE: DNA
<213> ORGANISM: Artificial Sequence
<220> FEATURE:
<223> OTHER INFORMATION: pHBT95-F71LN98DT135N Forward Primer

<400> SEQUENCE: 56
gatgtgccgg aaggaaatag cgaggaagat acaatatt     38

<210> SEQ ID NO 57
<211> LENGTH: 38
<212> TYPE: DNA
<213> ORGANISM: Artificial Sequence
<220> FEATURE:
<223> OTHER INFORMATION: pHBT95-F71LN98DT135N Reverse Primer

<400> SEQUENCE: 57
attgtatctt cctcgctatt tccttccggc acatccac     38

<210> SEQ ID NO 58
<211> LENGTH: 37
<212> TYPE: DNA
<213> ORGANISM: Artificial Sequence
<220> FEATURE:
<223> OTHER INFORMATION: pHBT95-Q38KF71LN98DT135N Forward Primer

<400> SEQUENCE: 58
caaaccacaa gcttataaac gtttcgtcaa aagttgc     37

<210> SEQ ID NO 59
<211> LENGTH: 37
<212> TYPE: DNA
<213> ORGANISM: Artificial Sequence
<220> FEATURE:
<223> OTHER INFORMATION: pHBT95-Q38KF71LN98DT135N Reverse Primer

<400> SEQUENCE: 59
cttttgacga aacgtttata agcttgtggt ttgtcga     37

<210> SEQ ID NO 60
<211> LENGTH: 37
<212> TYPE: DNA
<213> ORGANISM: Artificial Sequence
<220> FEATURE:
<223> OTHER INFORMATION: pHBT95-Q38KF71LN98DT135N Forward Primer -continued

<400> SEQUENCE: 60
gacgttagtc tccggcctcc cggcggattt cagcacg                                    37

<210> SEQ ID NO 61
<211> LENGTH: 37
<212> TYPE: DNA
<213> ORGANISM: Artificial Sequence
<220> FEATURE:
<223> OTHER INFORMATION: pHBT95-Q38KF71LN98DT135N Reverse Primer

<400> SEQUENCE: 61
gctgaaatcc gccgggaggc cggagactaa cgtcacg                                    37

<210> SEQ ID NO 62
<211> LENGTH: 37
<212> TYPE: DNA
<213> ORGANISM: Artificial Sequence
<220> FEATURE:
<223> OTHER INFORMATION: pHBT95-Q38KF71LN98DT135N Forward Primer

<400> SEQUENCE: 62
aagtattatt ggcggtgacc ataggcttgt taattac                                    37

<210> SEQ ID NO 63
<211> LENGTH: 37
<212> TYPE: DNA
<213> ORGANISM: Artificial Sequence
<220> FEATURE:
<223> OTHER INFORMATION: pHBT95-Q38KF71LN98DT135N Reverse Primer

<400> SEQUENCE: 63
attaacaagc ctatggtcac cgccaataat acttacc                                    37

<210> SEQ ID NO 64
<211> LENGTH: 38
<212> TYPE: DNA
<213> ORGANISM: Artificial Sequence
<220> FEATURE:
<223> OTHER INFORMATION: pHBT95-Q38KF71LN98DT135N Forward Primer

<400> SEQUENCE: 64
gatgtgccgg aaggaaatag cgaggaagat acaatatt                                   38

<210> SEQ ID NO 65
<211> LENGTH: 38
<212> TYPE: DNA
<213> ORGANISM: Artificial Sequence
<220> FEATURE:
<223> OTHER INFORMATION: pHBT95-Q38KF71LN98DT135N Reverse Primer

<400> SEQUENCE: 65
attgtatctt cctcgctatt tccttccggc acatccac                                   38

<210> SEQ ID NO 66
<211> LENGTH: 50
<212> TYPE: DNA
<213> ORGANISM: Artificial Sequence
<220> FEATURE:
<223> OTHER INFORMATION: pHBT-ABI2 Forward Primer

<400> SEQUENCE: 66
cggctccctc tccccttgct ccgtggatcc atggacgaag tttctcctgc                      50

<210> SEQ ID NO 67

```
<211> LENGTH: 55
<212> TYPE: DNA
<213> ORGANISM: Artificial Sequence
<220> FEATURE:
<223> OTHER INFORMATION: pHBT-ABI2 Reverse Primer

<400> SEQUENCE: 67
gtagtctgga acgtcgtatg ggtaaggcct attcaaggat ttgctcttga atttc        55

<210> SEQ ID NO 68
<211> LENGTH: 49
<212> TYPE: DNA
<213> ORGANISM: Artificial Sequence
<220> FEATURE:
<223> OTHER INFORMATION: pHBT-HAB1 Forward Primer

<400> SEQUENCE: 68
cggctccctc tccccttgct ccgtggatcc atggaggaga tgactcccg              49

<210> SEQ ID NO 69
<211> LENGTH: 54
<212> TYPE: DNA
<213> ORGANISM: Artificial Sequence
<220> FEATURE:
<223> OTHER INFORMATION: pHBT-HAB1 Reverse Primer

<400> SEQUENCE: 69
gtagtctgga acgtcgtatg ggtaaggcct ggttctggtc ttgaactttc tttg         54

<210> SEQ ID NO 70
<211> LENGTH: 52
<212> TYPE: DNA
<213> ORGANISM: Artificial Sequence
<220> FEATURE:
<223> OTHER INFORMATION: pHBT-HAB2 Forward Primer

<400> SEQUENCE: 70
cggctccctc tccccttgct ccgtggatcc atggaagaga tttcacctgc ag           52

<210> SEQ ID NO 71
<211> LENGTH: 54
<212> TYPE: DNA
<213> ORGANISM: Artificial Sequence
<220> FEATURE:
<223> OTHER INFORMATION: pHBT-HAB2 Reverse Primer

<400> SEQUENCE: 71
gtagtctgga acgtcgtatg ggtaaggcct agatctggtc ttgaactttc tttg         54

<210> SEQ ID NO 72
<211> LENGTH: 49
<212> TYPE: DNA
<213> ORGANISM: Artificial Sequence
<220> FEATURE:
<223> OTHER INFORMATION: pHBT-PP2CA Forward Primer

<400> SEQUENCE: 72
cggctccctc tccccttgct ccgtggatcc atggctggga tttgttgcg              49

<210> SEQ ID NO 73
<211> LENGTH: 52
<212> TYPE: DNA
<213> ORGANISM: Artificial Sequence
<220> FEATURE:
<223> OTHER INFORMATION: pHBT-PP2CA Reverse Primer

<400> SEQUENCE: 73
```

-continued gtagtctgga acgtcgtatg ggtaaggcct agacgacgct tgattattcc tc        52

<210> SEQ ID NO 74
<211> LENGTH: 51
<212> TYPE: DNA
<213> ORGANISM: Artificial Sequence
<220> FEATURE:
<223> OTHER INFORMATION: pHBT-HAI1 Forward Primer

<400> SEQUENCE: 74
cggctccctc tccccttgct ccgtggatcc atggctgaga tttgttacga g          51

<210> SEQ ID NO 75
<211> LENGTH: 51
<212> TYPE: DNA
<213> ORGANISM: Artificial Sequence
<220> FEATURE:
<223> OTHER INFORMATION: pHBT-HAI1 Reverse Primer

<400> SEQUENCE: 75
gtagtctgga acgtcgtatg ggtaaggcct cgtgtctcgt cgtagatcaa c          51

<210> SEQ ID NO 76
<211> LENGTH: 52
<212> TYPE: DNA
<213> ORGANISM: Artificial Sequence
<220> FEATURE:
<223> OTHER INFORMATION: pHBT-HAI2 Forward Primer

<400> SEQUENCE: 76
cggctccctc tccccttgct ccgtggatcc atggcggata tttgttatga ag        52

<210> SEQ ID NO 77
<211> LENGTH: 50
<212> TYPE: DNA
<213> ORGANISM: Artificial Sequence
<220> FEATURE:
<223> OTHER INFORMATION: pHBT-HAI2 Reverse Primer

<400> SEQUENCE: 77
gtagtctgga acgtcgtatg ggtaaggcct agcaacgtgt ctctttcttc            50

<210> SEQ ID NO 78
<211> LENGTH: 52
<212> TYPE: DNA
<213> ORGANISM: Artificial Sequence
<220> FEATURE:
<223> OTHER INFORMATION: pHBT-HAI3 Forward Primer

<400> SEQUENCE: 78
cggctccctc tccccttgct ccgtggatcc atggccgaga tatgttacga ag        52

<210> SEQ ID NO 79
<211> LENGTH: 51
<212> TYPE: DNA
<213> ORGANISM: Artificial Sequence
<220> FEATURE:
<223> OTHER INFORMATION: pHBT-HAI3 Reverse Primer

<400> SEQUENCE: 79
gtagtctgga acgtcgtatg ggtaaggcct tcttctgaga tcaatcacaa c          51

<210> SEQ ID NO 80
<211> LENGTH: 50
<212> TYPE: DNA

<213> ORGANISM: Artificial Sequence
<220> FEATURE:
<223> OTHER INFORMATION: pHBT-AHG1 Forward Primer

<400> SEQUENCE: 80
cggctccctc tcccttgct ccgtggatcc atgactgaaa tctacagaac         50

<210> SEQ ID NO 81
<211> LENGTH: 51
<212> TYPE: DNA
<213> ORGANISM: Artificial Sequence
<220> FEATURE:
<223> OTHER INFORMATION: pHBT-AHG1 Reverse Primer

<400> SEQUENCE: 81
gtagtctgga acgtcgtatg ggtaaggcct ctgagagcta ttcttgagat c       51

<210> SEQ ID NO 82
<211> LENGTH: 53
<212> TYPE: DNA
<213> ORGANISM: Artificial Sequence
<220> FEATURE:
<223> OTHER INFORMATION: pGEX-6P1-PYL13 Forward Primer

<400> SEQUENCE: 82
gaagttctgt tccaggggcc cctgggatcc atggaaagtt ctaagcaaaa acg     53

<210> SEQ ID NO 83
<211> LENGTH: 52
<212> TYPE: DNA
<213> ORGANISM: Artificial Sequence
<220> FEATURE:
<223> OTHER INFORMATION: pGEX-6P1-PYL13 Reverse Primer

<400> SEQUENCE: 83
atgcggccgc tcgagtcgac ccgggaattc ttacttcatc attttctttg tg      52

<210> SEQ ID NO 84
<211> LENGTH: 51
<212> TYPE: DNA
<213> ORGANISM: Artificial Sequence
<220> FEATURE:
<223> OTHER INFORMATION: pGEX-6P1-PYL2 Forward Primer

<400> SEQUENCE: 84
gaagttctgt tcaggggcc cctgggatcc atgagctcat ccccggccgt g        51

<210> SEQ ID NO 85
<211> LENGTH: 54
<212> TYPE: DNA
<213> ORGANISM: Artificial Sequence
<220> FEATURE:
<223> OTHER INFORMATION: pGEX-6P1-PYL2 Reverse Primer

<400> SEQUENCE: 85
atgcggccgc tcgagtcgac ccgggaattc ttattcatca tcatgcatag gtgc    54

<210> SEQ ID NO 86
<211> LENGTH: 49
<212> TYPE: DNA
<213> ORGANISM: Artificial Sequence
<220> FEATURE:
<223> OTHER INFORMATION: pGEX-6P1-PP2CA Forward Primer

<400> SEQUENCE: 86
gaagttctgt tccaggggcc cctgggatcc atggctggga tttgttgcg          49

<210> SEQ ID NO 87
<211> LENGTH: 55
<212> TYPE: DNA
<213> ORGANISM: Artificial Sequence
<220> FEATURE:
<223> OTHER INFORMATION: pGEX-6P1-PP2CA Reverse Primer

<400> SEQUENCE: 87
gtcagtcacg atgcggccgc tcgagtcgac ttaagacgac gcttgattat tcctc    55

<210> SEQ ID NO 88
<211> LENGTH: 50
<212> TYPE: DNA
<213> ORGANISM: Artificial Sequence
<220> FEATURE:
<223> OTHER INFORMATION: pGEX-6P1-ABI1 Forward Primer

<400> SEQUENCE: 88
gaagttctgt tccaggggcc cctgggatcc atggaggaag tatctccggc    50

<210> SEQ ID NO 89
<211> LENGTH: 52
<212> TYPE: DNA
<213> ORGANISM: Artificial Sequence
<220> FEATURE:
<223> OTHER INFORMATION: pGEX-6P1-ABI1 Reverse Primer

<400> SEQUENCE: 89
atgcggccgc tcgagtcgac ccgggaattc tcagttcaag ggtttgctct tg    52

<210> SEQ ID NO 90
<211> LENGTH: 50
<212> TYPE: DNA
<213> ORGANISM: Artificial Sequence
<220> FEATURE:
<223> OTHER INFORMATION: pGEX-6P1-ABI2 Forward Primer

<400> SEQUENCE: 90
gaagttctgt tccaggggcc cctgggatcc atggacgaag tttctcctgc    50

<210> SEQ ID NO 91
<211> LENGTH: 52
<212> TYPE: DNA
<213> ORGANISM: Artificial Sequence
<220> FEATURE:
<223> OTHER INFORMATION: pGEX-6P1-ABI2 Reverse Primer

<400> SEQUENCE: 91
atgcggccgc tcgagtcgac ccgggaattc tcaattcaag gatttgctct tg    52

<210> SEQ ID NO 92
<211> LENGTH: 50
<212> TYPE: DNA
<213> ORGANISM: Artificial Sequence
<220> FEATURE:
<223> OTHER INFORMATION: pGEX-6P1-AHG1 Forward Primer

<400> SEQUENCE: 92
gaagttctgt tccaggggcc cctgggatcc atgactgaaa tctacagaac    50

<210> SEQ ID NO 93
<211> LENGTH: 51
<212> TYPE: DNA
<213> ORGANISM: Artificial Sequence
<220> FEATURE:

-continued

<223> OTHER INFORMATION: pGEX-6P1-AHG1 Reverse Primer

<400> SEQUENCE: 93
atgcggccgc tcgagtcgac ccgggaattc ttactgagag ctattcttga g    51

<210> SEQ ID NO 94
<211> LENGTH: 32
<212> TYPE: DNA
<213> ORGANISM: Artificial Sequence
<220> FEATURE:
<223> OTHER INFORMATION: pET28a-PYL13 Forward Primer

<400> SEQUENCE: 94
atcggatcca tggaaagttc taagcaaaaa cg    32

<210> SEQ ID NO 95
<211> LENGTH: 34
<212> TYPE: DNA
<213> ORGANISM: Artificial Sequence
<220> FEATURE:
<223> OTHER INFORMATION: pET28a-PYL13 Reverse Primer

<400> SEQUENCE: 95
atcgaattct tacttcatca ttttctttgt gagc    34

<210> SEQ ID NO 96
<211> LENGTH: 26
<212> TYPE: DNA
<213> ORGANISM: Artificial Sequence
<220> FEATURE:
<223> OTHER INFORMATION: pET28a-PYL2 Forward Primer

<400> SEQUENCE: 96
atcggatcca tgagctcatc cccggc    26

<210> SEQ ID NO 97
<211> LENGTH: 29
<212> TYPE: DNA
<213> ORGANISM: Artificial Sequence
<220> FEATURE:
<223> OTHER INFORMATION: pET28a-PYL2 Reverse Primer

<400> SEQUENCE: 97
atcgaattct tattcatcat catgcatag    29

<210> SEQ ID NO 98
<211> LENGTH: 28
<212> TYPE: DNA
<213> ORGANISM: Artificial Sequence
<220> FEATURE:
<223> OTHER INFORMATION: pET28a-PYR1 Forward Primer

<400> SEQUENCE: 98
atcggatcca tgccttcgga gttaacac    28

<210> SEQ ID NO 99
<211> LENGTH: 29
<212> TYPE: DNA
<213> ORGANISM: Artificial Sequence
<220> FEATURE:
<223> OTHER INFORMATION: pET28a-PYR1 Reverse Primer

<400> SEQUENCE: 99
atcgaattct cacgtcacct gagaaccac    29

```
<210> SEQ ID NO 100
<211> LENGTH: 66
<212> TYPE: DNA
<213> ORGANISM: Artificial Sequence
<220> FEATURE:
<223> OTHER INFORMATION: pHBT-nLUC Forward Primer

<400> SEQUENCE: 100
cggctccctc tccccttgct ccgtggatcc gtcgactcta gactgcagca gatctcgtac      60
gcgtcc                                                                66

<210> SEQ ID NO 101
<211> LENGTH: 54
<212> TYPE: DNA
<213> ORGANISM: Artificial Sequence
<220> FEATURE:
<223> OTHER INFORMATION: pHBT-nLUC Reverse Primer

<400> SEQUENCE: 101
agaaacttta ttgccaaatg tttgaacgat tcatccatcc ttgtcaatca aggc            54

<210> SEQ ID NO 102
<211> LENGTH: 53
<212> TYPE: DNA
<213> ORGANISM: Artificial Sequence
<220> FEATURE:
<223> OTHER INFORMATION: pHBT-cLUC Forward Primer

<400> SEQUENCE: 102
agctctcggc tccctctccc cttgctccgt atgtccggtt atgtaaacaa tcc             53

<210> SEQ ID NO 103
<211> LENGTH: 64
<212> TYPE: DNA
<213> ORGANISM: Artificial Sequence
<220> FEATURE:
<223> OTHER INFORMATION: pHBT-cLUC Reverse Primer

<400> SEQUENCE: 103
tttattgcca aatgtttgaa cgatctgcag tctagagtcg acggatccgc cccgggacgc      60
gtac                                                                  64

<210> SEQ ID NO 104
<211> LENGTH: 28
<212> TYPE: DNA
<213> ORGANISM: Artificial Sequence
<220> FEATURE:
<223> OTHER INFORMATION: nLUC-PYR1 Forward Primer

<400> SEQUENCE: 104
cgtggatcca tgccttcgga gttaacac                                        28

<210> SEQ ID NO 105
<211> LENGTH: 26
<212> TYPE: DNA
<213> ORGANISM: Artificial Sequence
<220> FEATURE:
<223> OTHER INFORMATION: nLUC-PYR1 Reverse Primer

<400> SEQUENCE: 105
tccgtcgacc gtcacctgag aaccac                                          26

<210> SEQ ID NO 106
<211> LENGTH: 29
<212> TYPE: DNA
```

<210> SEQ ID NO 107
<211> LENGTH: 31
<212> TYPE: DNA
<213> ORGANISM: Artificial Sequence
<220> FEATURE:
<223> OTHER INFORMATION: nLUC-PYL1 Forward Primer

<400> SEQUENCE: 106
cgtggatcca tggcgaattc agagtcctc                                    29

<210> SEQ ID NO 107
<211> LENGTH: 31
<212> TYPE: DNA
<213> ORGANISM: Artificial Sequence
<220> FEATURE:
<223> OTHER INFORMATION: nLUC-PYL1 Reverse Primer

<400> SEQUENCE: 107
tccgtcgacc ctaacctgag aagagttgtt g                                 31

<210> SEQ ID NO 108
<211> LENGTH: 26
<212> TYPE: DNA
<213> ORGANISM: Artificial Sequence
<220> FEATURE:
<223> OTHER INFORMATION: nLUC-PYL2 Forward Primer

<400> SEQUENCE: 108
cgtggatcca tgagctcatc cccggc                                       26

<210> SEQ ID NO 109
<211> LENGTH: 31
<212> TYPE: DNA
<213> ORGANISM: Artificial Sequence
<220> FEATURE:
<223> OTHER INFORMATION: nLUC-PYL2 Reverse Primer

<400> SEQUENCE: 109
tccgtcgatt catcatcatg cataggtgca g                                 31

<210> SEQ ID NO 110
<211> LENGTH: 27
<212> TYPE: DNA
<213> ORGANISM: Artificial Sequence
<220> FEATURE:
<223> OTHER INFORMATION: nLUC-PYL3 Forward Primer

<400> SEQUENCE: 110
cgtggatcca tgaatcttgc tccaatc                                      27

<210> SEQ ID NO 111
<211> LENGTH: 30
<212> TYPE: DNA
<213> ORGANISM: Artificial Sequence
<220> FEATURE:
<223> OTHER INFORMATION: nLUC-PYL3 Reverse Primer

<400> SEQUENCE: 111
tccgtcgagg tcggagaagc cgtggaaatg                                   30

<210> SEQ ID NO 112
<211> LENGTH: 28
<212> TYPE: DNA
<213> ORGANISM: Artificial Sequence
<220> FEATURE:
<223> OTHER INFORMATION: nLUC-PYL4 Forward Primer

<400> SEQUENCE: 112
cgtggatcca tgcttgccgt tcaccgtc                                     28

<210> SEQ ID NO 113
<211> LENGTH: 32
<212> TYPE: DNA
<213> ORGANISM: Artificial Sequence
<220> FEATURE:
<223> OTHER INFORMATION: nLUC-PYL4 Reverse Primer

<400> SEQUENCE: 113
tccgtcgaca gagacatctt cttcttgctc tc                                 32

<210> SEQ ID NO 114
<211> LENGTH: 30
<212> TYPE: DNA
<213> ORGANISM: Artificial Sequence
<220> FEATURE:
<223> OTHER INFORMATION: nLUC-PYL5 Forward Primer

<400> SEQUENCE: 114
cgtggatcca tgaggtcacc ggtgcaactc                                    30

<210> SEQ ID NO 115
<211> LENGTH: 28
<212> TYPE: DNA
<213> ORGANISM: Artificial Sequence
<220> FEATURE:
<223> OTHER INFORMATION: nLUC-PYL5 Reverse Primer

<400> SEQUENCE: 115
tccgtcgatt gccggttggt acttcgag                                      28

<210> SEQ ID NO 116
<211> LENGTH: 31
<212> TYPE: DNA
<213> ORGANISM: Artificial Sequence
<220> FEATURE:
<223> OTHER INFORMATION: nLUC-PYL6 Forward Primer

<400> SEQUENCE: 116
cgtggatcca tgccaacgtc gatacagttt c                                  31

<210> SEQ ID NO 117
<211> LENGTH: 31
<212> TYPE: DNA
<213> ORGANISM: Artificial Sequence
<220> FEATURE:
<223> OTHER INFORMATION: nLUC-PYL6 Reverse Primer

<400> SEQUENCE: 117
tccgtcgacg agaatttaga agtgttctcg g                                  31

<210> SEQ ID NO 118
<211> LENGTH: 28
<212> TYPE: DNA
<213> ORGANISM: Artificial Sequence
<220> FEATURE:
<223> OTHER INFORMATION: nLUC-PYL7 Forward Primer

<400> SEQUENCE: 118
cgtggatcca tggagatgat cggaggag                                      28

<210> SEQ ID NO 119
<211> LENGTH: 26
<212> TYPE: DNA
<213> ORGANISM: Artificial Sequence
<220> FEATURE:

```
<223> OTHER INFORMATION: nLUC-PYL7 Reverse Primer

<400> SEQUENCE: 119
tccgtcgaaa ggttggtttc tgtatg                                          26

<210> SEQ ID NO 120
<211> LENGTH: 28
<212> TYPE: DNA
<213> ORGANISM: Artificial Sequence
<220> FEATURE:
<223> OTHER INFORMATION: nLUC-PYL8 Forward Primer

<400> SEQUENCE: 120
cgtggatcca tggaagctaa cgggattg                                        28

<210> SEQ ID NO 121
<211> LENGTH: 29
<212> TYPE: DNA
<213> ORGANISM: Artificial Sequence
<220> FEATURE:
<223> OTHER INFORMATION: nLUC-PYL8 Reverse Primer

<400> SEQUENCE: 121
tccgtcgaga ctctcgattc tgtcgtgtc                                       29

<210> SEQ ID NO 122
<211> LENGTH: 28
<212> TYPE: DNA
<213> ORGANISM: Artificial Sequence
<220> FEATURE:
<223> OTHER INFORMATION: nLUC-PYL9 Forward Primer

<400> SEQUENCE: 122
cgtggatcca tgatggacgg cgttgaag                                        28

<210> SEQ ID NO 123
<211> LENGTH: 25
<212> TYPE: DNA
<213> ORGANISM: Artificial Sequence
<220> FEATURE:
<223> OTHER INFORMATION: nLUC-PYL9 Reverse Primer

<400> SEQUENCE: 123
tccgtcgact gagtaatgtc ctgag                                           25

<210> SEQ ID NO 124
<211> LENGTH: 30
<212> TYPE: DNA
<213> ORGANISM: Artificial Sequence
<220> FEATURE:
<223> OTHER INFORMATION: nLUC-PYL10 Forward Primer

<400> SEQUENCE: 124
cgtggatcca tgaacggtga cgaaacaaag                                      30

<210> SEQ ID NO 125
<211> LENGTH: 29
<212> TYPE: DNA
<213> ORGANISM: Artificial Sequence
<220> FEATURE:
<223> OTHER INFORMATION: nLUC-PYL10 Reverse Primer

<400> SEQUENCE: 125
tccgtcgata tcttcttctc catagattc                                       29
```

```
<210> SEQ ID NO 126
<211> LENGTH: 31
<212> TYPE: DNA
<213> ORGANISM: Artificial Sequence
<220> FEATURE:
<223> OTHER INFORMATION: nLUC-PYL11 Forward Primer

<400> SEQUENCE: 126
cgtggatcca tggaaacttc tcaaaaatat c                              31

<210> SEQ ID NO 127
<211> LENGTH: 26
<212> TYPE: DNA
<213> ORGANISM: Artificial Sequence
<220> FEATURE:
<223> OTHER INFORMATION: nLUC-PYL11 Reverse Primer

<400> SEQUENCE: 127
tccgtcgaca actttagatg agccac                                    26

<210> SEQ ID NO 128
<211> LENGTH: 28
<212> TYPE: DNA
<213> ORGANISM: Artificial Sequence
<220> FEATURE:
<223> OTHER INFORMATION: nLUC-PYL12 Forward Primer

<400> SEQUENCE: 128
cgtggatcca tgaaaacatc tcaagaac                                  28

<210> SEQ ID NO 129
<211> LENGTH: 27
<212> TYPE: DNA
<213> ORGANISM: Artificial Sequence
<220> FEATURE:
<223> OTHER INFORMATION: nLUC-PYL12 Reverse Primer

<400> SEQUENCE: 129
tccgtcgaag tgagctccat catcttc                                   27

<210> SEQ ID NO 130
<211> LENGTH: 32
<212> TYPE: DNA
<213> ORGANISM: Artificial Sequence
<220> FEATURE:
<223> OTHER INFORMATION: nLUC-PYL13 Forward Primer

<400> SEQUENCE: 130
cgtggatcca tggaaagttc taagcaaaaa cg                             32

<210> SEQ ID NO 131
<211> LENGTH: 30
<212> TYPE: DNA
<213> ORGANISM: Artificial Sequence
<220> FEATURE:
<223> OTHER INFORMATION: nLUC-PYL13 Reverse Primer

<400> SEQUENCE: 131
tccgtcgact tcatcatttt ctttgtgagc                                30

<210> SEQ ID NO 132
<211> LENGTH: 32
<212> TYPE: DNA
<213> ORGANISM: Artificial Sequence
<220> FEATURE:
<223> OTHER INFORMATION: cLUC-PYL13 Forward Primer
```

<400> SEQUENCE: 132
cgtggatcca tggaaagttc taagcaaaaa cg                        32

<210> SEQ ID NO 133
<211> LENGTH: 33
<212> TYPE: DNA
<213> ORGANISM: Artificial Sequence
<220> FEATURE:
<223> OTHER INFORMATION: cLUC-PYL13 Reverse Primer

<400> SEQUENCE: 133
tccgtcgact tattcatcat tttctttgtg agc                       33

<210> SEQ ID NO 134
<211> LENGTH: 22
<212> TYPE: DNA
<213> ORGANISM: Artificial Sequence
<220> FEATURE:
<223> OTHER INFORMATION: PYL13 Forward Primer for PCR

<400> SEQUENCE: 134
atggaaagtt ctaagcaaaa ac                                   22

<210> SEQ ID NO 135
<211> LENGTH: 24
<212> TYPE: DNA
<213> ORGANISM: Artificial Sequence
<220> FEATURE:
<223> OTHER INFORMATION: PYL13 Reverse Primer for PCR

<400> SEQUENCE: 135
ttacttcatc attttctttg tgag                                 24

<210> SEQ ID NO 136
<211> LENGTH: 21
<212> TYPE: DNA
<213> ORGANISM: Artificial Sequence
<220> FEATURE:
<223> OTHER INFORMATION: YFP Forward Primer for PCR

<400> SEQUENCE: 136
acgtaaacgg ccacaagttc a                                    21

<210> SEQ ID NO 137
<211> LENGTH: 24
<212> TYPE: DNA
<213> ORGANISM: Artificial Sequence
<220> FEATURE:
<223> OTHER INFORMATION: YFP Reverse Primer for PCR

<400> SEQUENCE: 137
actggtagct caggtagtgg ttgt                                 24

<210> SEQ ID NO 138
<211> LENGTH: 17
<212> TYPE: DNA
<213> ORGANISM: Artificial Sequence
<220> FEATURE:
<223> OTHER INFORMATION: RD29A Forward Primer

<400> SEQUENCE: 138
gccgacggga tttgacg                                         17

<210> SEQ ID NO 139
<211> LENGTH: 23

```
<212> TYPE: DNA
<213> ORGANISM: Artificial Sequence
<220> FEATURE:
<223> OTHER INFORMATION: RD29A Reverse Primer

<400> SEQUENCE: 139
gccggaaatt tatcctcttc tga                                              23

<210> SEQ ID NO 140
<211> LENGTH: 23
<212> TYPE: DNA
<213> ORGANISM: Artificial Sequence
<220> FEATURE:
<223> OTHER INFORMATION: RAB18 Forward Primer

<400> SEQUENCE: 140
tcggtcgttg tattgtgctt ttt                                              23

<210> SEQ ID NO 141
<211> LENGTH: 24
<212> TYPE: DNA
<213> ORGANISM: Artificial Sequence
<220> FEATURE:
<223> OTHER INFORMATION: RAB18 Reverse Primer

<400> SEQUENCE: 141
ccagatgctc attacacact catg                                             24

<210> SEQ ID NO 142
<211> LENGTH: 20
<212> TYPE: DNA
<213> ORGANISM: Artificial Sequence
<220> FEATURE:
<223> OTHER INFORMATION: COR15A Forward Primer

<400> SEQUENCE: 142
aacgaggcca caaagaaagc                                                  20

<210> SEQ ID NO 143
<211> LENGTH: 25
<212> TYPE: DNA
<213> ORGANISM: Artificial Sequence
<220> FEATURE:
<223> OTHER INFORMATION: COR15A Reverse Primer

<400> SEQUENCE: 143
cagcttcttt acccaatgta tctgc                                            25

<210> SEQ ID NO 144
<211> LENGTH: 22
<212> TYPE: DNA
<213> ORGANISM: Artificial Sequence
<220> FEATURE:
<223> OTHER INFORMATION: KIN1 Forward Primer

<400> SEQUENCE: 144
tctcatcatc actaaccaaa ac                                               22

<210> SEQ ID NO 145
<211> LENGTH: 18
<212> TYPE: DNA
<213> ORGANISM: Artificial Sequence
<220> FEATURE:
<223> OTHER INFORMATION: KIN1 Reverse Primer

<400> SEQUENCE: 145
```

```
gacccgaatc gctacttg                                                    18

<210> SEQ ID NO 146
<211> LENGTH: 22
<212> TYPE: DNA
<213> ORGANISM: Artificial Sequence
<220> FEATURE:
<223> OTHER INFORMATION: ACTIN2 Forward Primer

<400> SEQUENCE: 146
ctaagctctc aagatcaaag gc                                               22

<210> SEQ ID NO 147
<211> LENGTH: 22
<212> TYPE: DNA
<213> ORGANISM: Artificial Sequence
<220> FEATURE:
<223> OTHER INFORMATION: ACTIN2 Reverse Primer

<400> SEQUENCE: 147
aacattgcaa agagtttcaa gg                                               22

<210> SEQ ID NO 148
<211> LENGTH: 495
<212> TYPE: DNA
<213> ORGANISM: Artificial Sequence
<220> FEATURE:
<223> OTHER INFORMATION: PYL13 cDNA

<400> SEQUENCE: 148
atggaaagtt ctaagcaaaa acgatgtcgc tctagcgtag tcgagaccat tgaagcacca      60
ttaccactag tgtggtccat cctacgtagt ttcgacaaac cacaagctta tcaacgtttc     120
gtcaaaagtt gcaccatgcg ctctggcggc ggcggcggca aaggaggaga aggaaaaggc     180
tccgtccggg acgtgacgtt agtctccggc ttcccggcgg atttcagcac ggagaggctc     240
gaagagctag atgatgagtc tcacgtgatg gtggtaagta ttattggcgg taaccatagg     300
cttgttaatt acaaatcgaa aacgaaggtg gtcgcgtcgc cggaggatat ggcaaagaag     360
acggtggtgg tggagagtta cgtggtggat gtgccggaag gaactagcga ggaagataca     420
atattttttg ttgataacat tattcggtat aaccttactt cacttgctaa gctcacaaag     480
aaaatgatga agtaa                                                      495

<210> SEQ ID NO 149
<211> LENGTH: 191
<212> TYPE: PRT
<213> ORGANISM: Arabidopsis thaliana

<400> SEQUENCE: 149

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95
```

-continued

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Val His Arg
            115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
            165                 170                 175

Ala Met Ala Arg Asn Ser Gly Asp Gly Ser Gly Ser Gln Val Thr
        180                 185                 190

<210> SEQ ID NO 150
<211> LENGTH: 221
<212> TYPE: PRT
<213> ORGANISM: Arabidopsis thaliana

<400> SEQUENCE: 150

Met Ala Asn Ser Glu Ser Ser Ser Pro Val Asn Glu Glu Glu Asn
1               5                   10                  15

Ser Gln Arg Ile Ser Thr Leu His His Gln Thr Met Pro Ser Asp Leu
            20                  25                  30

Thr Gln Asp Glu Phe Thr Gln Leu Ser Gln Ser Ile Ala Glu Phe His
        35                  40                  45

Thr Tyr Gln Leu Gly Asn Gly Arg Cys Ser Ser Leu Leu Ala Gln Arg
    50                  55                  60

Ile His Ala Pro Pro Glu Thr Val Trp Ser Val Val Arg Arg Phe Asp
65                  70                  75                  80

Arg Pro Gln Ile Tyr Lys His Phe Ile Lys Ser Cys Asn Val Ser Glu
                85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
        115                 120                 125

Asp Arg Arg Val Thr Gly Phe Ser Ile Thr Gly Gly Glu His Arg Leu
130                 135                 140

Arg Asn Tyr Lys Ser Val Thr Thr Val His Arg Phe Glu Lys Glu Glu
145                 150                 155                 160

Glu Glu Glu Arg Ile Trp Thr Val Val Leu Glu Ser Tyr Val Val Asp
                165                 170                 175

Val Pro Glu Gly Asn Ser Glu Glu Asp Thr Arg Leu Phe Ala Asp Thr
            180                 185                 190

Val Ile Arg Leu Asn Leu Gln Lys Leu Ala Ser Ile Thr Glu Ala Met
        195                 200                 205

Asn Arg Asn Asn Asn Asn Asn Ser Ser Gln Val Arg
    210                 215                 220

<210> SEQ ID NO 151
<211> LENGTH: 190
<212> TYPE: PRT
<213> ORGANISM: Arabidopsis thaliana

<400> SEQUENCE: 151

Met Ser Ser Ser Pro Ala Val Lys Gly Leu Thr Asp Glu Glu Gln Lys
1               5                   10                  15

```
Thr Leu Glu Pro Val Ile Lys Thr Tyr His Gln Phe Glu Pro Asp Pro
             20                  25                  30

Thr Thr Cys Thr Ser Leu Ile Thr Gln Arg Ile His Ala Pro Ala Ser
         35                  40                  45

Val Val Trp Pro Leu Ile Arg Arg Phe Asp Asn Pro Glu Arg Tyr Lys
 50                  55                  60

His Phe Val Lys Arg Cys Arg Leu Ile Ser Gly Asp Gly Asp Val Gly
 65                  70                  75                  80

Ser Val Arg Glu Val Thr Val Ile Ser Gly Leu Pro Ala Ser Thr Ser
             85                  90                  95

Thr Glu Arg Leu Glu Phe Val Asp Asp His Arg Val Leu Ser Phe
             100                 105                 110

Arg Val Val Gly Gly Glu His Arg Leu Lys Asn Tyr Lys Ser Val Thr
             115                 120                 125

Ser Val Asn Glu Phe Leu Asn Gln Asp Ser Gly Lys Val Tyr Thr Val
             130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                 165                 170                 175

Leu Gly Val Ala Ala Thr Ser Ala Pro Met His Asp Asp Glu
                 180                 185                 190

<210> SEQ ID NO 152
<211> LENGTH: 209
<212> TYPE: PRT
<213> ORGANISM: Arabidopsis thaliana

<400> SEQUENCE: 152

Met Asn Leu Ala Pro Ile His Asp Pro Ser Ser Ser Thr Thr Thr
 1               5                  10                  15

Thr Ser Ser Ser Thr Pro Tyr Gly Leu Thr Lys Asp Glu Phe Ser Thr
             20                  25                  30

Leu Asp Ser Ile Ile Arg Thr His His Thr Phe Pro Arg Ser Pro Asn
         35                  40                  45

Thr Cys Thr Ser Leu Ile Ala His Arg Val Asp Ala Pro Ala His Ala
 50                  55                  60

Ile Trp Arg Phe Val Arg Asp Phe Ala Asn Pro Asn Lys Tyr Lys His
 65                  70                  75                  80

Phe Ile Lys Ser Cys Thr Ile Arg Val Asn Gly Asn Gly Ile Lys Glu
                 85                  90                  95

Ile Lys Val Gly Thr Ile Arg Glu Val Ser Val Val Ser Gly Leu Pro
                 100                 105                 110

Ala Ser Thr Ser Val Glu Ile Leu Glu Val Leu Asp Glu Glu Lys Arg
             115                 120                 125

Ile Leu Ser Phe Arg Val Leu Gly Gly Glu His Arg Leu Asn Asn Tyr
         130                 135                 140

Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                 165                 170                 175

Pro Gln Gly Asn Thr Glu Glu Asp Thr Arg Met Phe Val Asp Thr Val
                 180                 185                 190

Val Lys Ser Asn Leu Gln Asn Leu Ala Val Ile Ser Thr Ala Ser Pro
```

```
            195                 200                 205
Thr

<210> SEQ ID NO 153
<211> LENGTH: 207
<212> TYPE: PRT
<213> ORGANISM: Arabidopsis thaliana

<400> SEQUENCE: 153

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
            20                  25                  30

Leu Ser Arg Asp Ser Thr Ala Ala Arg Phe His Thr His Glu Val Gly
        35                  40                  45

Pro Asn Gln Cys Cys Ser Ala Val Ile Gln Glu Ile Ser Ala Pro Ile
    50                  55                  60

Ser Thr Val Trp Ser Val Val Arg Arg Phe Asp Asn Pro Gln Ala Tyr
65                  70                  75                  80

Lys His Phe Leu Lys Ser Cys Ser Val Ile Gly Gly Asp Gly Asp Asn
                85                  90                  95

Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
        115                 120                 125

Ser Phe Ser Val Val Gly Gly Asp His Arg Leu Ser Asn Tyr Arg Ser
    130                 135                 140

Val Thr Thr Leu His Pro Ser Pro Ile Ser Gly Thr Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
            180                 185                 190

Ile Ala Glu Asn Thr Ala Ala Glu Ser Lys Lys Lys Met Ser Leu
        195                 200                 205

<210> SEQ ID NO 154
<211> LENGTH: 203
<212> TYPE: PRT
<213> ORGANISM: Arabidopsis thaliana

<400> SEQUENCE: 154

Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
            20                  25                  30

Val Cys Leu Thr Arg Gly Met His Val Pro Glu His Val Ala Met His
        35                  40                  45

His Thr His Asp Val Gly Pro Asp Gln Cys Cys Ser Ser Val Val Gln
    50                  55                  60

Met Ile His Ala Pro Pro Glu Ser Val Trp Ala Leu Val Arg Arg Phe
65                  70                  75                  80

Asp Asn Pro Lys Val Tyr Lys Asn Phe Ile Arg Gln Cys Arg Ile Val
                85                  90                  95

Gln Gly Asp Gly Leu His Val Gly Asp Leu Arg Glu Val Met Val Val
            100                 105                 110
```

```
Ser Gly Leu Pro Ala Val Ser Ser Thr Glu Arg Leu Glu Ile Leu Asp
        115                 120                 125

Glu Glu Arg His Val Ile Ser Phe Ser Val Val Gly Gly Asp His Arg
130                 135                 140

Leu Lys Asn Tyr Arg Ser Val Thr Thr Leu His Ala Ser Asp Asp Glu
145                 150                 155                 160

Gly Thr Val Val Glu Ser Tyr Ile Val Asp Val Pro Pro Gly Asn
            165                 170                 175

Thr Glu Glu Glu Thr Leu Ser Phe Val Asp Thr Ile Val Arg Cys Asn
                180                 185                 190

Leu Gln Ser Leu Ala Arg Ser Thr Asn Arg Gln
        195                 200
```

<210> SEQ ID NO 155
<211> LENGTH: 215
<212> TYPE: PRT
<213> ORGANISM: Arabidopsis thaliana

<400> SEQUENCE: 155

```
Met Pro Thr Ser Ile Gln Phe Gln Arg Ser Thr Ala Ala Glu Ala
1               5                   10                  15

Ala Asn Ala Thr Val Arg Asn Tyr Pro His His Gln Lys Gln Val
            20                  25                  30

Gln Lys Val Ser Leu Thr Arg Gly Met Ala Asp Val Pro Glu His Val
        35                  40                  45

Glu Leu Ser His Thr His Val Val Gly Pro Ser Gln Cys Phe Ser Val
50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
            100                 105                 110

Arg Val Val Ser Gly Leu Pro Ala Ala Phe Ser Leu Glu Arg Leu Glu
        115                 120                 125

Ile Met Asp Asp Arg His Val Ile Ser Phe Ser Val Val Gly Gly
        130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
            180                 185                 190

Ala Asp Thr Ile Val Arg Cys Asn Leu Gln Ser Leu Ala Lys Leu Ala
        195                 200                 205

Glu Asn Thr Ser Lys Phe Ser
210                 215
```

<210> SEQ ID NO 156
<211> LENGTH: 211
<212> TYPE: PRT
<213> ORGANISM: Arabidopsis thaliana

<400> SEQUENCE: 156

```
Met Glu Met Ile Gly Gly Asp Asp Thr Asp Thr Glu Met Tyr Gly Ala
1               5                   10                  15
```

```
Leu Val Thr Ala Gln Ser Leu Arg Leu Arg His Leu His His Cys Arg
        20                  25                  30

Glu Asn Gln Cys Thr Ser Val Leu Val Lys Tyr Ile Gln Ala Pro Val
    35                  40                  45

His Leu Val Trp Ser Leu Val Arg Arg Phe Asp Gln Pro Gln Lys Tyr
50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
                85                  90                  95

Thr Glu Arg Leu Glu Gln Leu Asp Asp Glu His Ile Leu Gly Ile
            100                 105                 110

Asn Ile Ile Gly Gly Asp His Arg Leu Lys Asn Tyr Ser Ser Ile Leu
            115                 120                 125

Thr Val His Pro Glu Met Ile Asp Gly Arg Ser Gly Thr Met Val Met
130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
            180                 185                 190

Thr Phe Cys Asn Ala Ser Asn Gly Tyr Arg Glu Lys Asn His Thr Glu
            195                 200                 205

Thr Asn Leu
    210

<210> SEQ ID NO 157
<211> LENGTH: 188
<212> TYPE: PRT
<213> ORGANISM: Arabidopsis thaliana

<400> SEQUENCE: 157

Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
            20                  25                  30

Ser Ser Thr Leu Val Lys His Ile Asn Ala Pro Val His Ile Val Trp
        35                  40                  45

Ser Leu Val Arg Arg Phe Asp Gln Pro Gln Lys Tyr Lys Pro Phe Ile
    50                  55                  60

Ser Arg Cys Val Val Lys Gly Asn Met Glu Ile Gly Thr Val Arg Glu
65                  70                  75                  80

Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
            100                 105                 110

Gly Asp His Arg Leu Lys Asn Tyr Ser Ser Ile Ile Ser Leu His Pro
            115                 120                 125

Glu Thr Ile Glu Gly Arg Ile Gly Thr Leu Val Ile Glu Ser Phe Val
            130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
```

```
                165                 170                 175
Arg Leu Ala Val Gln Asp Thr Thr Glu Ser Arg Val
            180                 185

<210> SEQ ID NO 158
<211> LENGTH: 187
<212> TYPE: PRT
<213> ORGANISM: Arabidopsis thaliana

<400> SEQUENCE: 158

Met Met Asp Gly Val Glu Gly Thr Ala Met Tyr Gly Gly Leu Glu
1               5                   10                  15

Thr Val Gln Tyr Val Arg Thr His His Gln His Leu Cys Arg Glu Asn
                20                  25                  30

Gln Cys Thr Ser Ala Leu Val Lys His Ile Lys Ala Pro Leu His Leu
            35                  40                  45

Val Trp Ser Leu Val Arg Arg Phe Asp Gln Pro Gln Lys Tyr Lys Pro
        50                  55                  60

Phe Val Ser Arg Cys Thr Val Ile Gly Asp Pro Glu Ile Gly Ser Leu
65                  70                  75                  80

Arg Glu Val Asn Val Lys Ser Gly Leu Pro Ala Thr Thr Ser Thr Glu
                85                  90                  95

Arg Leu Glu Leu Leu Asp Asp Glu His Ile Leu Gly Ile Lys Ile
            100                 105                 110

Ile Gly Gly Asp His Arg Leu Lys Asn Tyr Ser Ser Ile Leu Thr Val
        115                 120                 125

His Pro Glu Ile Ile Glu Gly Arg Ala Gly Thr Met Val Ile Glu Ser
    130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185

<210> SEQ ID NO 159
<211> LENGTH: 183
<212> TYPE: PRT
<213> ORGANISM: Arabidopsis thaliana

<400> SEQUENCE: 159

Met Asn Gly Asp Glu Thr Lys Lys Val Glu Ser Glu Tyr Ile Lys Lys
1               5                   10                  15

His His Arg His Glu Leu Val Glu Ser Gln Cys Ser Ser Thr Leu Val
                20                  25                  30

Lys His Ile Lys Ala Pro Leu His Leu Val Trp Ser Ile Val Arg Arg
            35                  40                  45

Phe Asp Glu Pro Gln Lys Tyr Lys Pro Phe Ile Ser Arg Cys Val Val
        50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110

Leu Lys Asn Tyr Ser Ser Thr Ile Ser Leu His Ser Glu Thr Ile Asp
```

```
            115                 120                 125
Gly Lys Thr Gly Thr Leu Ala Ile Glu Ser Phe Val Val Asp Val Pro
        130                 135                 140
Glu Gly Asn Thr Lys Glu Gly Thr Cys Phe Phe Val Glu Ala Leu Ile
145                 150                 155                 160
Gln Cys Asn Leu Asn Ser Leu Ala Asp Val Thr Glu Arg Leu Gln Ala
                165                 170                 175
Glu Ser Met Glu Lys Lys Ile
            180

<210> SEQ ID NO 160
<211> LENGTH: 161
<212> TYPE: PRT
<213> ORGANISM: Arabidopsis thaliana

<400> SEQUENCE: 160

Met Glu Thr Ser Gln Lys Tyr His Thr Cys Gly Ser Thr Leu Val Gln
1               5                   10                  15
Thr Ile Asp Ala Pro Leu Ser Leu Val Trp Ser Ile Leu Arg Arg Phe
            20                  25                  30
Asp Asn Pro Gln Ala Tyr Lys Gln Phe Val Lys Thr Cys Asn Leu Ser
        35                  40                  45
Ser Gly Asp Gly Gly Glu Gly Ser Val Arg Glu Val Thr Val Val Ser
    50                  55                  60
Gly Leu Pro Ala Glu Phe Ser Arg Glu Arg Leu Asp Glu Leu Asp Asp
65                  70                  75                  80
Glu Ser His Val Met Met Ile Ser Ile Ile Gly Gly Asp His Arg Leu
                85                  90                  95
Val Asn Tyr Arg Ser Lys Thr Met Ala Phe Val Ala Ala Asp Thr Glu
            100                 105                 110
Glu Lys Thr Val Val Val Glu Ser Tyr Val Val Asp Val Pro Glu Gly
        115                 120                 125
Asn Ser Glu Glu Glu Thr Thr Ser Phe Ala Asp Thr Ile Val Gly Phe
    130                 135                 140
Asn Leu Lys Ser Leu Ala Lys Leu Ser Glu Arg Val Ala His Leu Lys
145                 150                 155                 160
Leu

<210> SEQ ID NO 161
<211> LENGTH: 159
<212> TYPE: PRT
<213> ORGANISM: Arabidopsis thaliana

<400> SEQUENCE: 161

Met Lys Thr Ser Gln Glu Gln His Val Cys Gly Ser Thr Val Val Gln
1               5                   10                  15
Thr Ile Asn Ala Pro Leu Pro Leu Val Trp Ser Ile Leu Arg Arg Phe
            20                  25                  30
Asp Asn Pro Lys Thr Phe Lys His Phe Val Lys Thr Cys Lys Leu Arg
        35                  40                  45
Ser Gly Asp Gly Gly Glu Gly Ser Val Arg Glu Val Thr Val Val Ser
    50                  55                  60
Asp Leu Pro Ala Ser Phe Ser Leu Glu Arg Leu Asp Glu Leu Asp Asp
65                  70                  75                  80
Glu Ser His Val Met Val Ile Ser Ile Ile Gly Gly Asp His Arg Leu
                85                  90                  95
```

Val Asn Tyr Gln Ser Lys Thr Val Phe Val Ala Glu Glu Glu
            100                 105                 110

Lys Thr Val Val Glu Ser Tyr Val Val Asp Val Pro Glu Gly Asn
    115                 120                 125

Thr Glu Glu Thr Thr Leu Phe Ala Asp Thr Ile Val Gly Cys Asn
    130                 135                 140

Leu Arg Ser Leu Ala Lys Leu Ser Glu Lys Met Met Glu Leu Thr
145                 150                 155

<210> SEQ ID NO 162
<211> LENGTH: 162
<212> TYPE: PRT
<213> ORGANISM: Arabidopsis lyrata

<400> SEQUENCE: 162

Met Asp Thr Ser Gln Glu Tyr His Lys Cys Gly Ser Thr Leu Ala Gln
1               5                   10                  15

Thr Ile Asp Ala Pro Leu Ser Ile Val Trp Ser Ile Leu Arg Arg Phe
            20                  25                  30

Asp Asn Pro Gln Ala Tyr Lys Gln Phe Val Lys Thr Cys Asn Leu Ser
        35                  40                  45

Phe Gly Asp Gly Gly Thr Gly Ser Val Arg Glu Val Thr Val Val Ser
    50                  55                  60

Gly Leu Pro Ala Glu Phe Ser Gln Glu Arg Leu Asp Glu Leu Asp Asp
65                  70                  75                  80

Glu Ser His Met Met Val Ile Ser Ile Ile Gly Gly Asp His Arg Leu
                85                  90                  95

Val Asn Tyr Arg Ser Lys Thr Met Ala Phe Val Ala Ala Asp Glu Glu
            100                 105                 110

Glu Lys Thr Val Val Glu Ser Tyr Val Val Asp Val Pro Glu Gly
        115                 120                 125

Asn Ser Glu Glu Glu Thr Thr Ser Phe Ala Asp Asn Ile Val Gly Phe
    130                 135                 140

Asn Leu Lys Ser Leu Ala Lys Leu Ser Glu Lys Met Val Ala His Leu
145                 150                 155                 160

Lys Leu

<210> SEQ ID NO 163
<211> LENGTH: 159
<212> TYPE: PRT
<213> ORGANISM: Arabidopsis lyrata

<400> SEQUENCE: 163

Met Lys Thr Ser Gln Lys Gln His Val Cys Gly Ser Thr Leu Val Gln
1               5                   10                  15

Thr Ile Asn Ala Pro Leu Pro Leu Val Trp Ser Ile Leu Arg Arg Phe
            20                  25                  30

Asp Asn Pro Lys Thr Tyr Lys Gln Phe Val Lys Lys Cys Glu Leu Arg
        35                  40                  45

Ser Gly Asp Gly Gly Glu Gly Ser Val Arg Glu Val Thr Val Val Ser
    50                  55                  60

Asp Phe Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

```
Val Asn Tyr Arg Ser Lys Thr Met Val Phe Val Ala Thr Glu Glu Glu
                100                 105                 110

Lys Thr Val Val Glu Glu Ser Tyr Val Val Asp Val Pro Gly Gly Asn
        115                 120                 125

Thr Asp Glu Glu Thr Thr Leu Phe Ala Asn Thr Ile Val Lys Cys Asn
130                 135                 140

Leu Arg Ser Leu Ala Lys Leu Ser Glu Lys Met Val Glu Leu Thr
145                 150                 155

<210> SEQ ID NO 164
<211> LENGTH: 164
<212> TYPE: PRT
<213> ORGANISM: Arabidopsis lyrata

<400> SEQUENCE: 164

Met Glu Ser Ser Lys Gln Lys Arg Cys His Ser Ser Val Val Glu Thr
1               5                   10                  15

Ile Glu Ala Pro Leu Pro Leu Val Trp Ser Ile Leu Arg Ser Phe Asp
                20                  25                  30

Lys Pro Gln Ala Tyr Gln Arg Phe Val Lys Ser Cys Thr Met Arg Ser
            35                  40                  45

Ser Gly Gly Gly Gly Lys Gly Gly Glu Gly Lys Gly Ser Val Arg Asp
50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Ile Ser Ile Ile Gly
                85                  90                  95

Gly Asn His Arg Leu Val Asn Tyr Lys Ser Lys Thr Thr Val Val Ala
                100                 105                 110

Ser Pro Glu Asp Val Thr Glu Lys Thr Val Val Glu Ser Tyr Val Val
            115                 120                 125

Val Asp Val Pro Glu Gly Asn Ser Glu Glu Asp Thr Lys Phe Phe Val
        130                 135                 140

Asp Asn Ile Ile Arg Tyr Asn Leu Thr Ser Leu Ala Lys Leu Thr Lys
145                 150                 155                 160

Lys Met Met Gly

<210> SEQ ID NO 165
<211> LENGTH: 185
<212> TYPE: PRT
<213> ORGANISM: Glycine max

<400> SEQUENCE: 165

Met Leu Cys Lys Gln Asn Leu Glu Thr Pro Thr Ile Lys Ala Met Leu
1               5                   10                  15

Asn Thr Tyr His Ala Ser Lys Leu Pro Ser Asn Gln Cys Gly Ser Ser
                20                  25                  30

Leu Val Gln Thr Ile Asp Ala Pro Leu Pro Leu Val Trp Ser Leu Ile
            35                  40                  45

Arg Arg Phe Glu Tyr Pro Gln Gly Tyr Lys Leu Phe Val Lys Lys Cys
        50                  55                  60

Thr Leu Leu Asp Gly Asn Gly Gly Ile Gly Ser Val Arg Glu Val Met
65                  70                  75                  80

Val Thr Ser Gly Leu Pro Ala Gly Val Ser Val Glu Arg Leu Asp Lys
                85                  90                  95
```

Leu Asp Asp Asp Lys His Val Phe Lys Phe Ser Ile Ile Gly Gly Asp
            100                 105                 110

His Arg Leu Val Asn Tyr Ser Ser Thr Ile Thr Leu His Gln Glu Glu
            115                 120                 125

Glu Glu Tyr Gly Gly Lys Thr Val Ala Ile Glu Ser Tyr Ala Val Asp
            130                 135                 140

Val Pro Ala Gly Ser Thr Val Asp Asp Thr Cys Ser Phe Ala Asn Thr
145                 150                 155                 160

Ile Ile Ala Cys Asn Leu Arg Ser Leu Ala Lys Ile Thr Glu Glu Met
            165                 170                 175

Val Cys Lys Ala Asn Gln Ile Lys Val
            180                 185

<210> SEQ ID NO 166
<211> LENGTH: 185
<212> TYPE: PRT
<213> ORGANISM: Glycine max

<400> SEQUENCE: 166

Met Leu Cys Lys Gln Asp Leu Glu Thr Pro Thr Ile Lys Ala Met Leu
1               5                   10                  15

Asn Thr Tyr His Ala Ser Lys Leu Ser Ser Asn Gln Cys Gly Ser Ser
            20                  25                  30

Leu Val Gln Thr Ile Asp Ala Pro Leu Pro Leu Val Trp Ser Leu Ile
            35                  40                  45

Arg Arg Phe Glu Tyr Pro Gln Gly Tyr Lys Leu Phe Val Lys Lys Cys
        50                  55                  60

Asn Leu Leu Asp Gly Asp Gly Gly Ile Gly Ser Val Arg Glu Val Met
65                  70                  75                  80

Ile Thr Ser Gly Leu Pro Ala Gly Val Ser Val Glu Arg Leu Asp Lys
            85                  90                  95

Leu Asp Asp Asp Lys His Val Leu Lys Phe Ser Ile Ile Gly Gly Asp
            100                 105                 110

His Arg Leu Val Asn Tyr Ser Ser Thr Ile Thr Leu His Glu Glu Glu
            115                 120                 125

Glu Glu Tyr Gly Gly Lys Thr Val Ala Ile Glu Ser Tyr Ala Val Asp
            130                 135                 140

Val Pro Ala Gly Ser Ser Gly Asp Asp Thr Cys Ser Phe Ala Asn Thr
145                 150                 155                 160

Ile Ile Ala Cys Asn Leu Arg Ser Leu Ala Lys Ile Thr Glu Glu Lys
            165                 170                 175

Val Cys Lys Val Asn Gln Ile Lys Leu
            180                 185

<210> SEQ ID NO 167
<211> LENGTH: 197
<212> TYPE: PRT
<213> ORGANISM: Arabidopsis thaliana

<400> SEQUENCE: 167

Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His His Cys Arg
            20                  25                  30

Glu Asn Gln Cys Thr Ser Val Leu Val Lys Tyr Ile Gln Ala Pro Val
            35                  40                  45

```
His Leu Val Trp Ser Leu Val Arg Arg Phe Asp Gln Pro Gln Lys Tyr
    50              55              60
Lys Pro Phe Ile Ser Arg Cys Thr Val Asn Gly Asp Pro Glu Ile Gly
65              70              75              80
Cys Leu Arg Glu Val Asn Val Lys Ser Gly Leu Pro Ala Thr Thr Ser
            85              90              95
Thr Glu Arg Leu Glu Gln Leu Asp Asp Glu Glu His Ile Leu Gly Ile
            100             105             110
Asn Ile Ile Gly Gly Asp His Arg Leu Lys Asn Tyr Ser Ser Ile Leu
        115             120             125
Thr Val His Pro Glu Met Ile Asp Gly Arg Ser Gly Thr Met Val Met
    130             135             140
Glu Ser Phe Val Val Asp Val Pro Gln Gly Asn Thr Lys Asp Asp Thr
145             150             155             160
Cys Tyr Phe Val Glu Ser Leu Ile Lys Cys Asn Leu Lys Ser Leu Ala
            165             170             175
Cys Val Ser Glu Arg Leu Ala Ala Gln Asp Ile Thr Asn Ser Ile Ala
            180             185             190
Thr Phe Cys Asn Ala
        195
```

DROUGHT TOLERANT TRANSGENIC PLANTS AND METHOD OF MAKING SAME

CLAIM OF PRIORITY UNDER 35 U.S.C. §119

This non-provisional U.S. patent application claims priority to U.S. provisional patent application No. 61/856,198, entitled "DROUGHT TOLERANT TRANSGENIC PLANTS AND METHOD OF MAKING SAME" filed Jul. 19, 2013, assigned to the assignee hereof, and hereby expressly incorporated by reference herein.

STATEMENT AS TO U.S. GOVERNMENT INTERESTS IN INVENTIONS MADE UNDER FEDERALLY SPONSORED RESEARCH AND DEVELOPMENT

This invention was made with government support under GM059138, awarded by National Institutes of Health. The government has certain rights in the invention.

BACKGROUND

Abscisic acid (ABA) is an important phytohormone that participates in plant abiotic stress signaling. In some plants, endogenous ABA is produced in response to environmental stresses, such as heat stress, water stress, and salt stress. Under these conditions, an increase in ABA triggers a pathway that ultimately results in an increased expression of stress-tolerance related genes. These stress-tolerance related genes are typically inhibited by enzymes called clade-A protein phosphatases type 2Cs (PP2Cs, comprising ABI1, ABI2, HAB1, HAB2, AHG1, PP2CA, HAI1, HAI2, and HAI3), but the inhibition is released and the stress-tolerance related genes are expressed in the presence of ABA and a family of PYR/PYL/RCAR proteins (hereafter referred to as PYLs).

The PYLs are ABA receptors in the cytoplasm and nucleus (Fujii et al., 2009; Ma et al., 2009b; Park et al., 2009). The PYL family has 14 members in *Arabidopsis*, including PYR1 and PYL1-13, each containing a START domain. Several of the PYLs have been shown to bind to and inhibit PP2Cs in the presence of ABA (Fujii et al., 2009; Ma et al., 2009b; Park et al., 2009). Structural studies confirmed that the PYLs are ABA receptors and found the PP2Cs can function as co-receptors because they enhance the ABA-binding affinities of the PYLs (Santiago et al., 2009; Yin et al., 2009). In *Arabidopsis* protoplasts, PYR1 and PYL1-12 relieved PP2C (ABI1) inhibition of ABA-dependent activation of RD29B-LUC expression by the SnRK2 protein kinases such as OST1/SnRK2.6 (Fujii et al., 2009).

PYLs have an ABA-binding pocket comprised of four highly conserved regions named CL1-4 (Yin et al., 2009). The structure of PYL changes after ABA binding (Santiago et al., 2009; Yin et al., 2009), allowing the formation of an ABA-PYL-PP2C complex and the inhibition of PP2Cs, thus releasing the inhibition of SnRK2.2/2.3/2.6 by clade A PP2Cs. SnRK2.2/2.3/2.6 are positive regulators of ABA signaling. Activated SnRK2.2/2.3/2.6 can phosphorylate and activate transcription factors such as ABFs/AREBs to induce the expression of ABA-responsive genes such as RD29B (Fujii et al., 2009). In guard cells, the SnRK2s can also phosphorylate and activate the NADPH oxidase catalytic subunit RBOHF, leading to the production of reactive oxygen species (ROS).

The interactions between PYLs and PP2Cs are highly specific. Many monomeric PYL proteins may also interact with certain PP2Cs in an ABA-independent manner in yeast two hybrid assays and pull down assays (Hao et al., 2011; Park et al., 2009). However, this interaction is weak and in the particular case of PYL10-ABI1 interaction, the dissociation constant (Kd) changed from 1.2 μM without ABA to 0.02 μM with ABA (Hao et al, 2011), indicating that the interaction between PYL10 and ABI1 is enhanced by ABA. In vitro assays found that PYL10 shows obvious ABA-independent inhibition of ABI1, HAB1 and HAB2 with a PYL:PP2C ratio of 1:1, and PYL5-10 (except the untested PYL7) show ABA-independent inhibition of ABI1, HAB1, HAB2, and PP2CA to different degrees with the PYL:PP2C ratio of 10:1 and 100:1 (Hao et al., 2011). However, the ABA-independent inhibitions are much weaker than ABA-dependent ones.

Although the PYL family proteins have been studied intensively in recent years, little information is available for PYL13, which differs from other PYLs in the highly conserved regions of their ABA-binding pocket.

BRIEF SUMMARY OF SELECTED EMBODIMENTS OF THE PRESENT INVENTION

Embodiments of the present invention relate generally to new drought tolerant transgenic plants and methods of creating the drought tolerant transgenic plants. In an embodiment, a transgenic plant having increased drought tolerance compared to a control plant is provided. In an embodiment, the transgenic plant is transformed with a recombinant DNA construct comprising a polynucleotide sequence which comprises a nucleotide sequence encoding a polypeptide that is at least 95% identical to a PYL protein, such as SEQ ID NO: 1.

In a further embodiment, the polypeptide consists of SEQ ID NO: 1. In some embodiments, the polynucleotide sequence encodes a polypeptide having at least one homologous point mutation based on the Q38K, F71L, and T135N variations from PYL13. For example, the polypeptide is based on an amino acid sequence selected from the group consisting of SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, and SEQ ID NO: 161, wherein the at least one homologous point mutation is inserted into the amino acid sequence via the polynucleotide sequence.

In an exemplary embodiment, the polypeptide is overexpressed compared to the control plant. In some embodiments, the polynucleotide sequence is operably linked to a promoter. For example, the promoter may be selected from the group consisting of a constitutive promoter, an inducible promoter, a tissue specific promoter, and a stress-responsive promoter. In some embodiments, the transgenic plant exhibits an increased survival rate after drought as compared to the control plant. In some embodiments, the transgenic plant comprises at least one characteristic selected from the group consisting of a decreased relative transpiration rate, a decreased relative stomatal conductance, an increased relative photosynthetic rate, and an increased relative water use efficiency as compared to the control plant. In still further embodiments, the transgenic plant comprises accelerated stress responsive gene expression as compared to the control plant. The accelerated stress response gene expression may be selected from the group consisting of RD29A, KIN1, COR15A, and RAB18. In a still further embodiment, a transgenic seed obtained from the transformed plant of claim 1, and wherein the transgenic seed comprises said recombinant DNA construct, is provided.

The control plant can be a wild-type plant, a calibrator transgenic line, or any other plant suitable for the purpose of comparison.

In one embodiment, the gene encoding the PYL polypeptide is under the control of a tissue-specific promoter. In one embodiment, the gene encoding the PYL polypeptide is under the control of a stress-responsive promoter. In one embodiment, the gene encoding the PYL polypeptide is under the control of a constitutive promoter. In some embodiments, the constitutive promoter is the cauliflower mosaic virus 35S promoter. In one embodiment, the gene encoding the PYL polypeptide is under the control of a temporal-specific promoter.

In one embodiment, a method of producing a transgenic plant with increased drought tolerance as compared to a control plant is provided. In an embodiment, the method includes (i) providing a recombinant DNA construct comprising a polynucleotide sequence encoding a polypeptide that is at least 95% identical to a PYL protein such as SEQ ID NO: 1; and (ii) introducing the recombinant DNA construct into a plant to produce a transgenic plant, wherein the transgenic plant exhibits increased drought tolerance. In an embodiment, the polypeptide consists of SEQ ID NO: 1. In some embodiments, other PYL proteins modified with the variations identified in PYL13 are used. In an embodiment, the method further includes crossing the transgenic plant with itself or crossing the transgenic plant with another plant to produce a transgenic seed.

In some embodiments, a construct comprises a plasmid or vector containing a gene of interest along with promoter and regulator sequences associated with expression and regulation of the gene of interest in the recipient cell.

Other aspects and features, as recited by the claims, will become apparent to those skilled in the art upon review of the following non-limited detailed description of the invention in conjunction with the accompanying figures.

BRIEF DESCRIPTION OF THE SEVERAL VIEWS OF THE DRAWINGS

Figure 1:
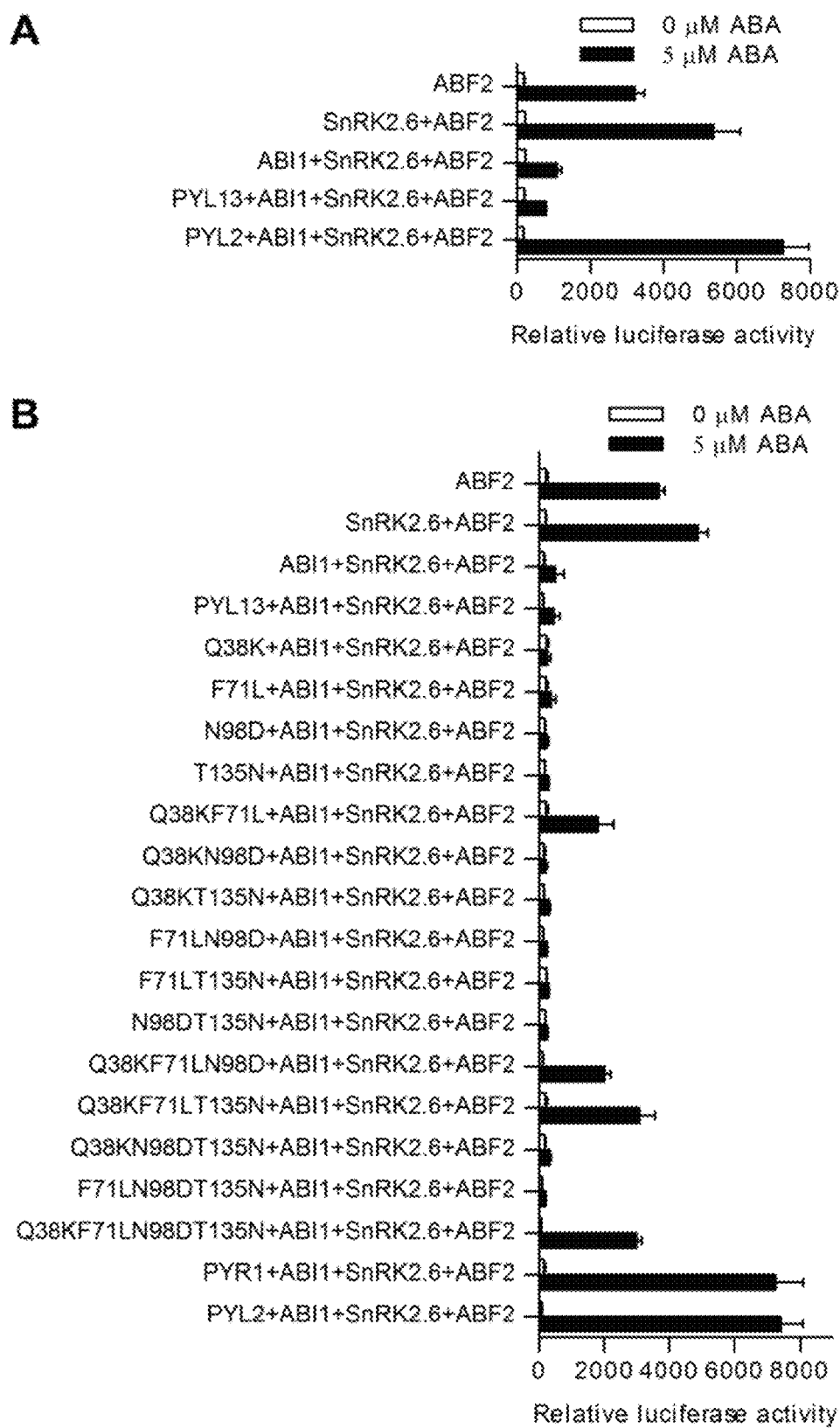
Figure 2A:
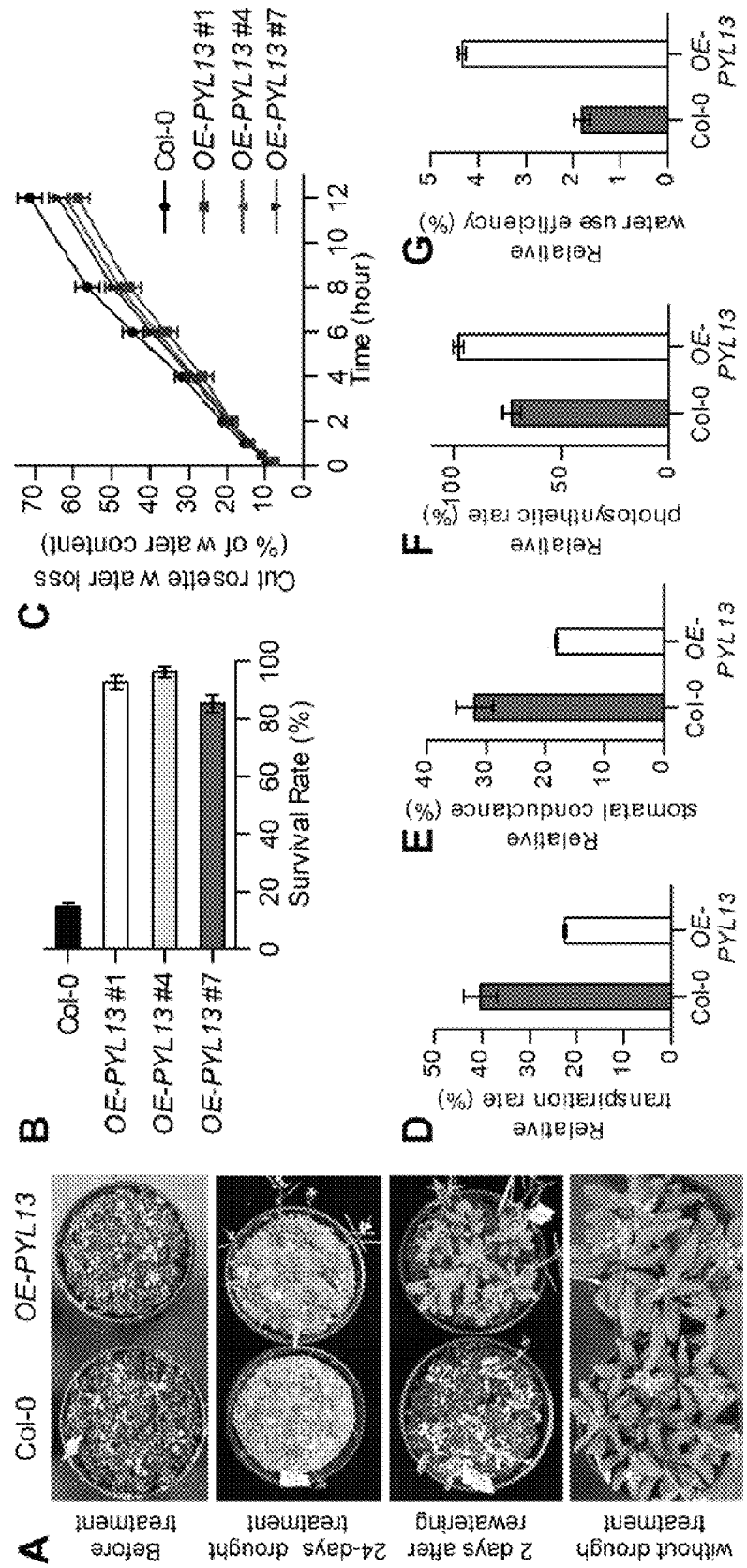
Figure 2B:
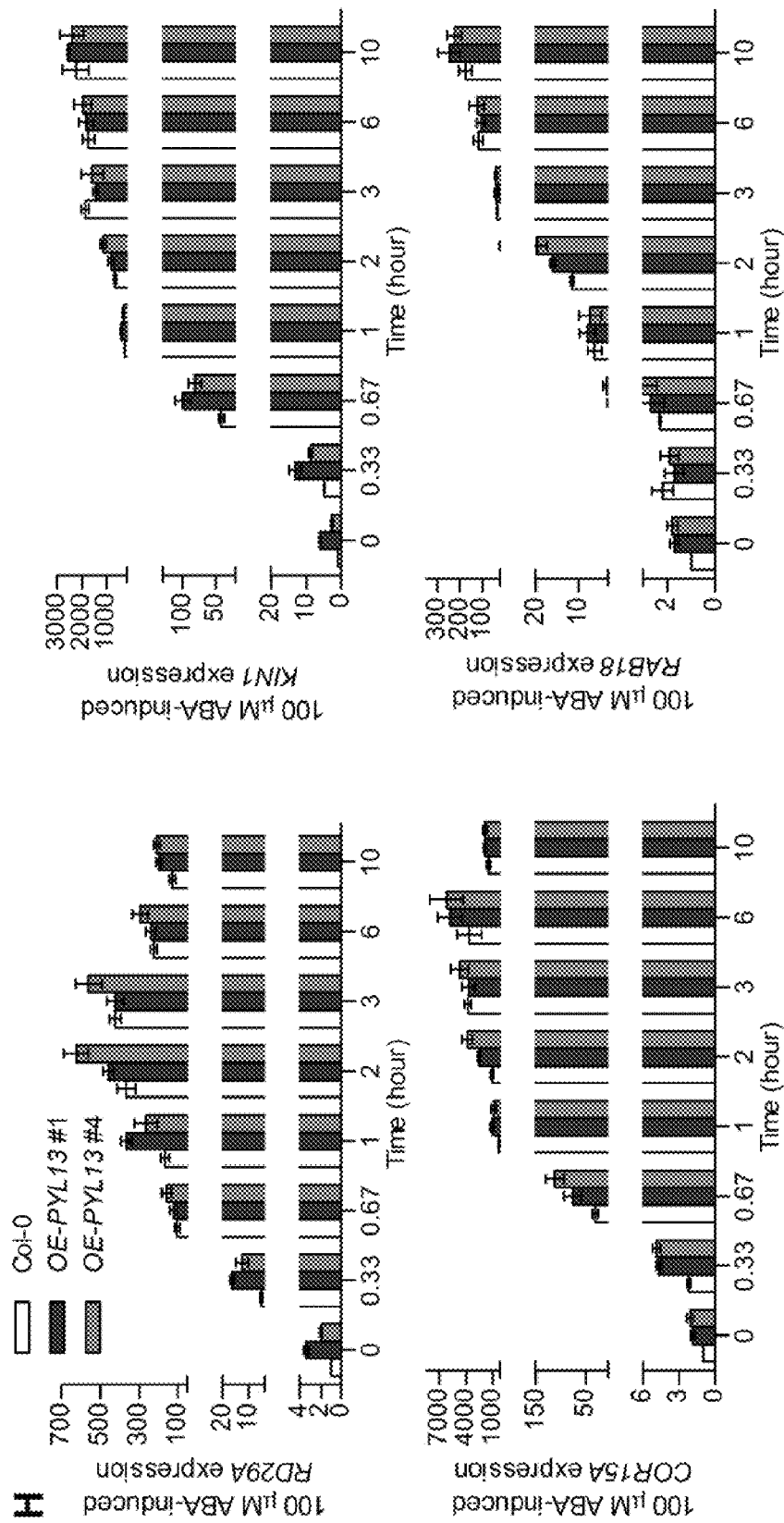
Figure 3:
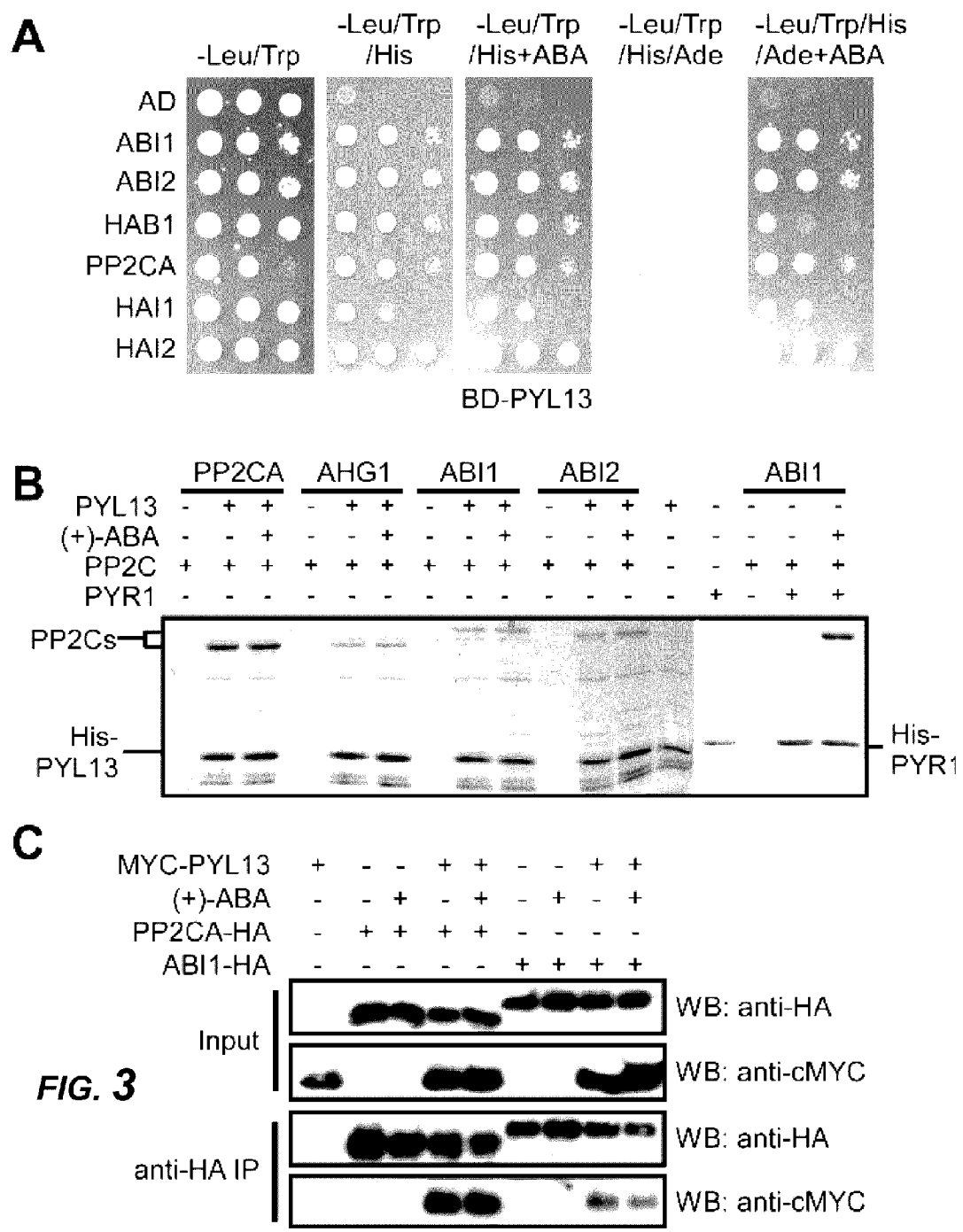
Figure 4:
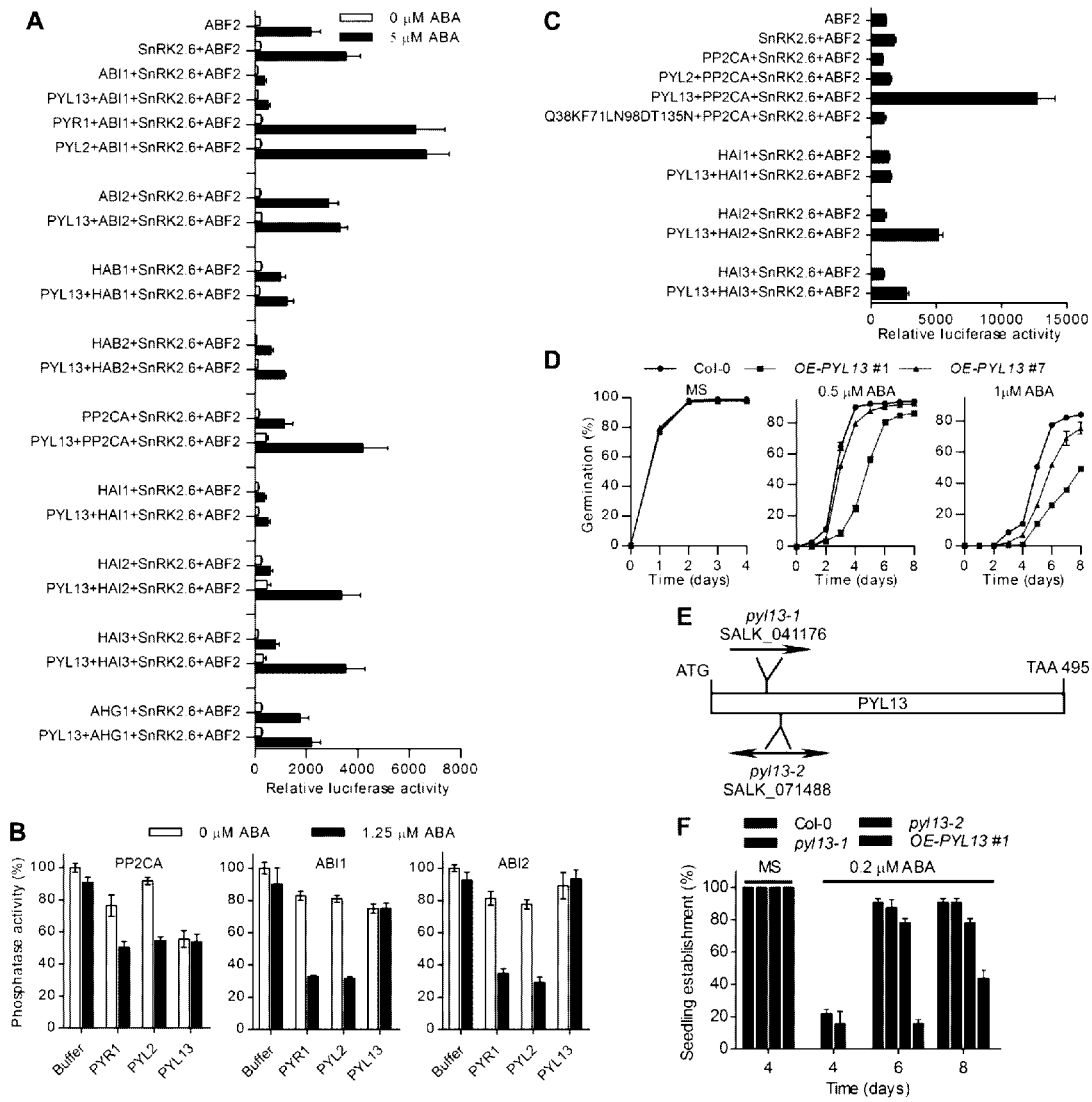
Figure 5:
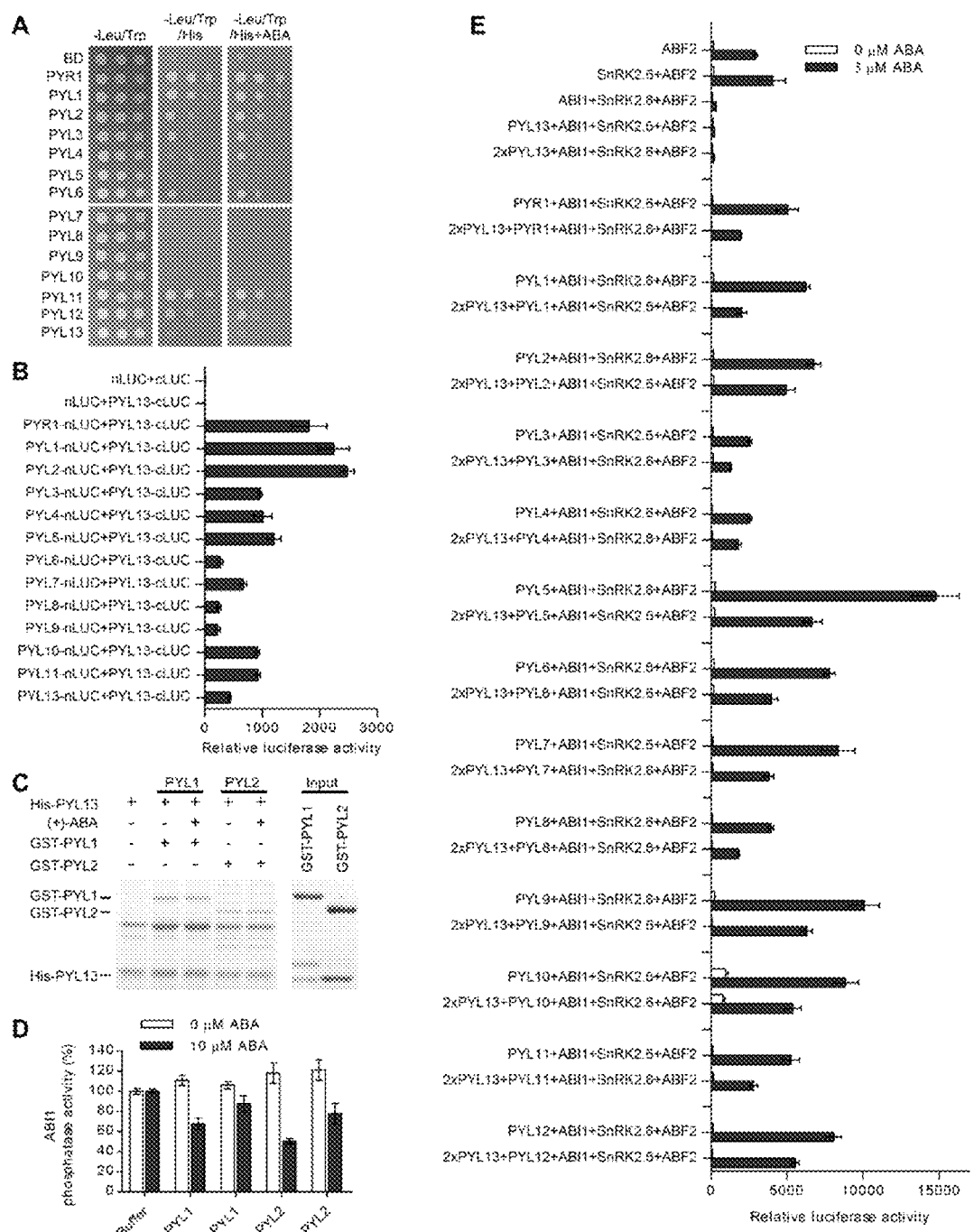
Figure 6:
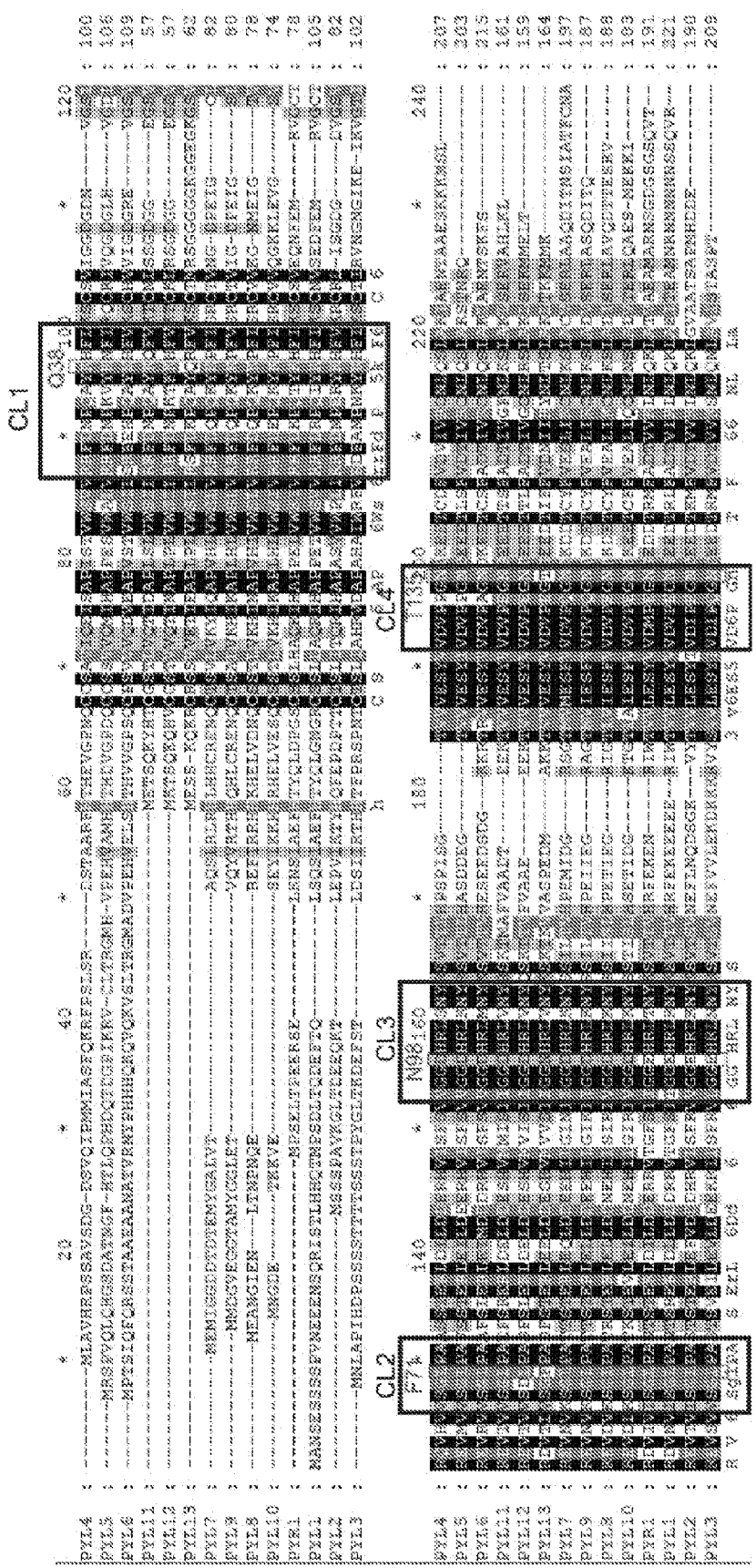
Figure 7:
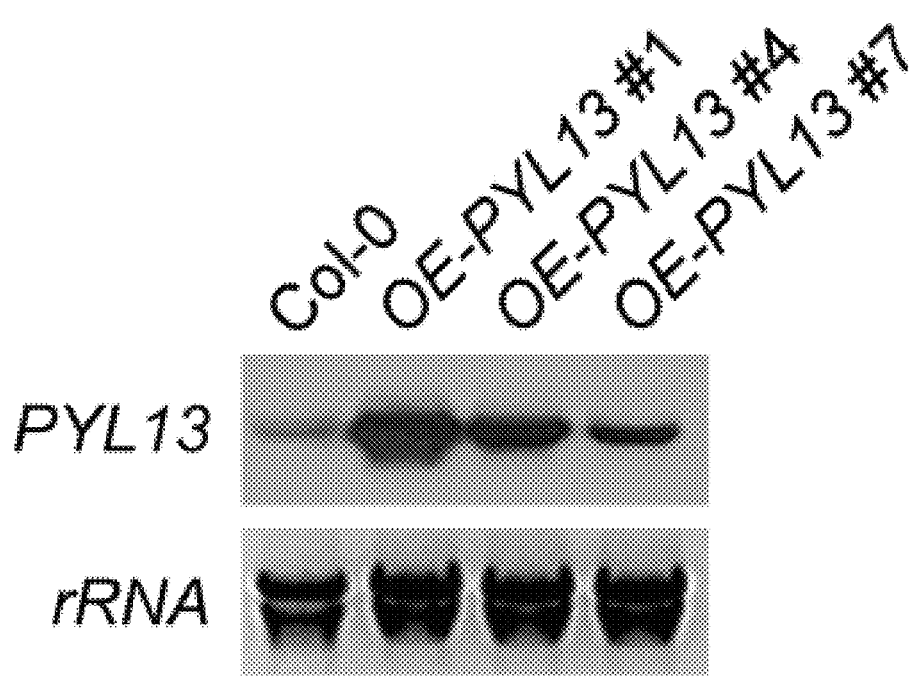
Figure 8:
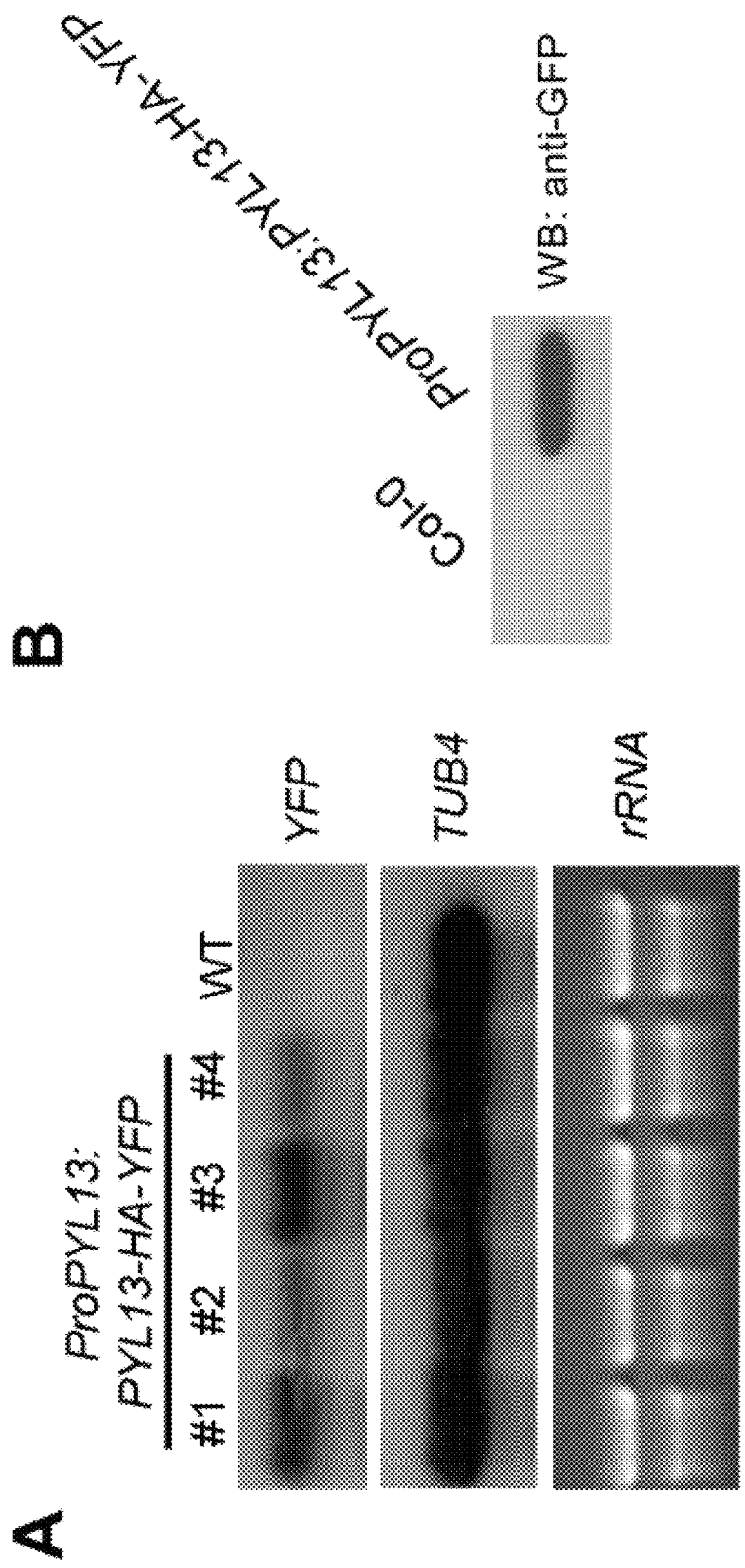
Figure 9:
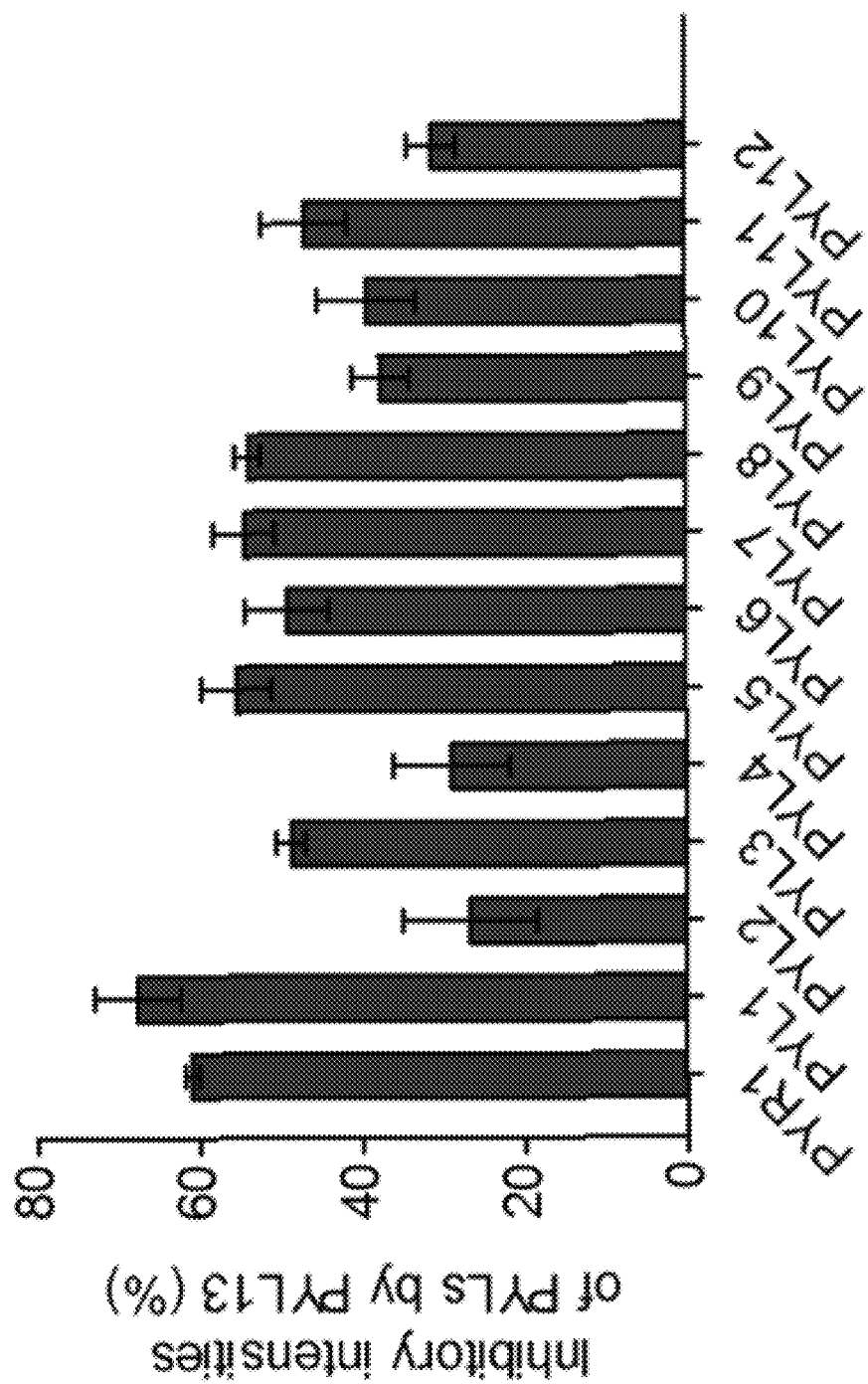
Figure 10:
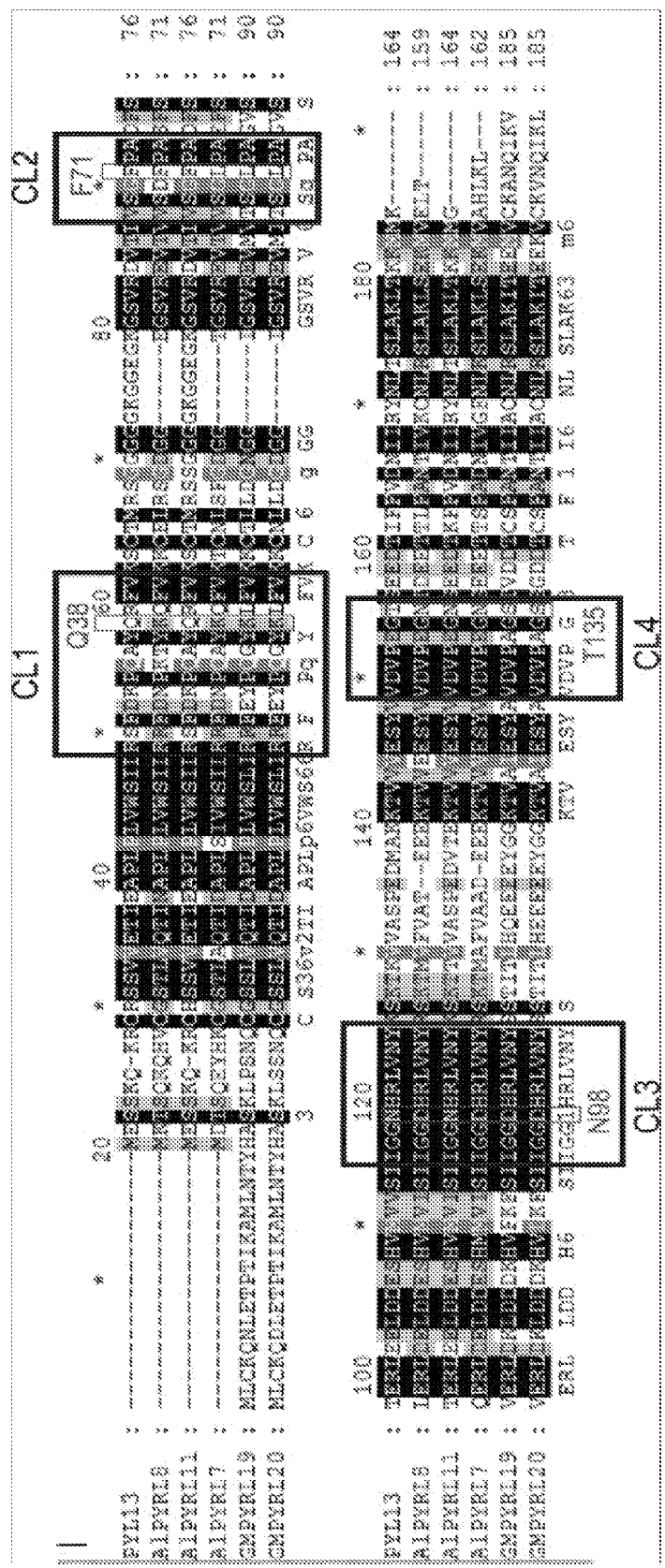
Figure 12:
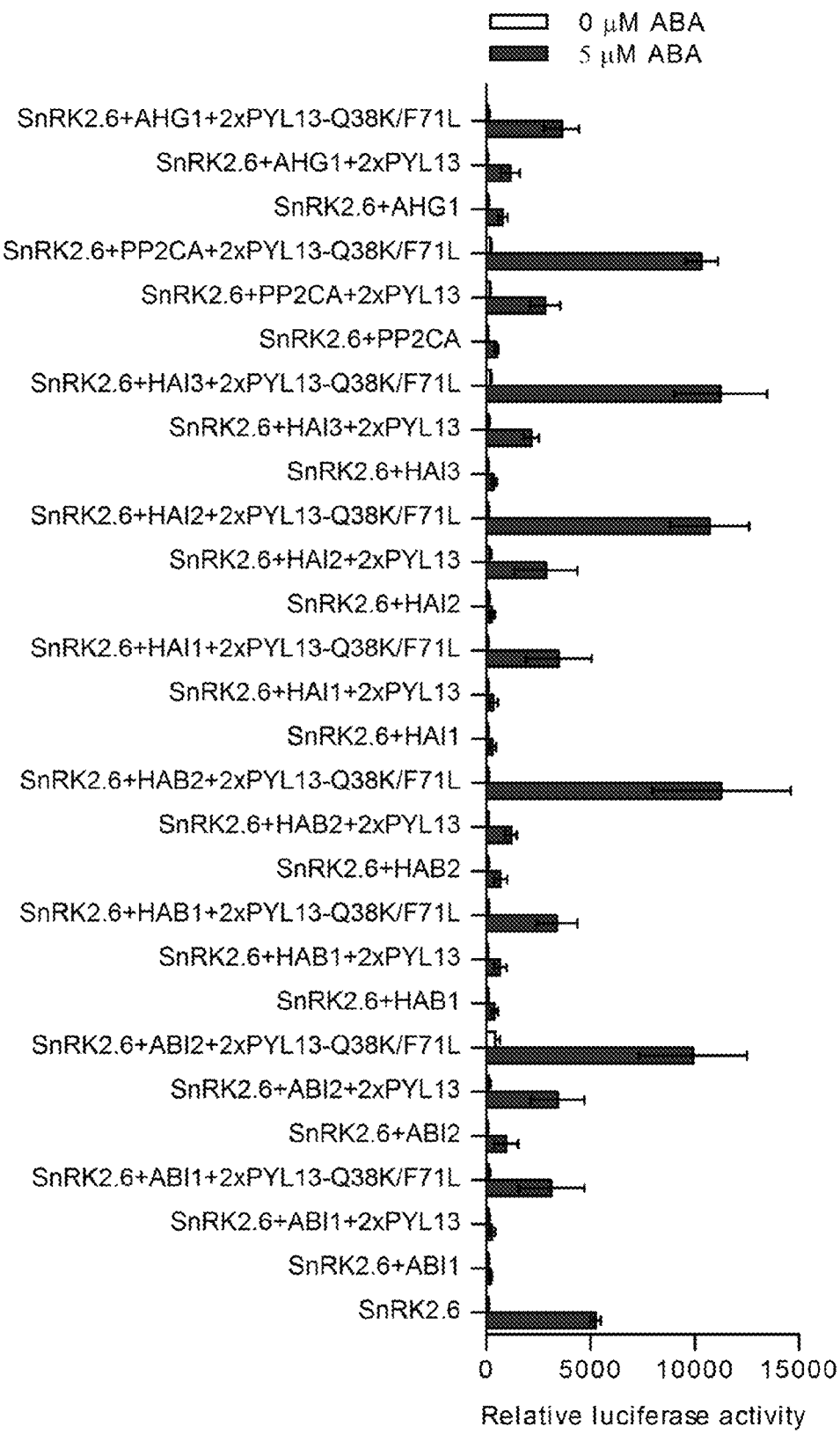
Figure 13:
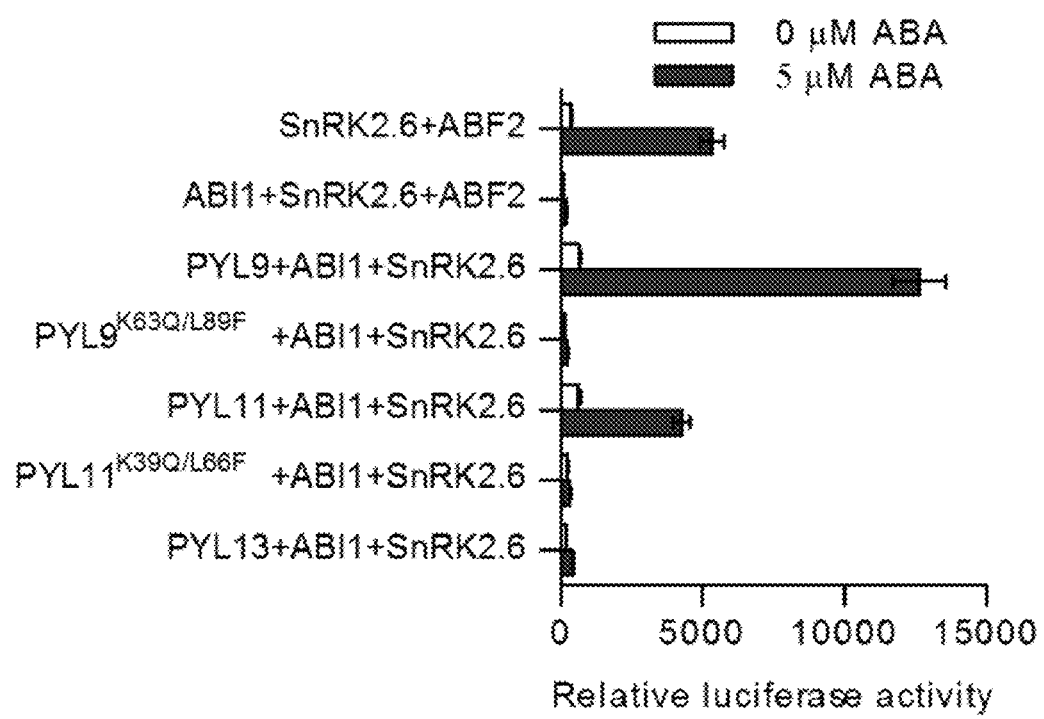

Having thus described embodiments of the present invention in general terms, reference will now be made to the accompanying drawings, which are not necessarily draw to scale, and wherein:

FIG. 1, panel A and panel B, provides data on the difference between PYL13 and other PYLs based on the induction of stress-responsive RD29B-LUC expression in the presence and absence of ABA, in accordance with embodiments of the disclosure;

FIG. 2A provides representative photographs treatment and control plants under various conditions (panel A), survival rates of treatment and control plants two days after watering was resumed (panel B), cumulative transpirational water loss from rosettes of the treatment and control plants (panel C), transpiration rate of treatment and control plants (panel D), stomatal conductance of treatment and control plants (panel E), photosynthetic rate of treatment and control plants (panel F), and water use efficiency of treatment and control plants (panel G), in accordance with embodiments of the disclosure;

FIG. 2B provides data on expression of stress responsive genes in treatment and control plants, in accordance with an embodiment of the disclosure;

FIG. 3 provides data on the binding of PYL13 to clade A PP2Cs in an ABA-independent manner, in accordance with an embodiment of the disclosure;

FIG. 4 provides data on PYL13 inhibition of clade A PP2Cs in an ABA-independent manner, in accordance with an embodiment of the disclosure;

FIG. 5 provides data on PYL13 interaction and inhibition of other PYLs, in accordance with an embodiment of the disclosure;

FIG. 6 provides sequence alignments of PYL13 and other PYLs showing difference in selected residues, note that an abbreviated sequence having 197 residues (SEQ ID NO: 167) is provided for PYL7 to comply with space limitations (the full sequence for PYL7 is provided in SEQ ID NO: 156), in accordance with an embodiment of the disclosure;

FIG. 7 provides a Northern Blot analysis of PYL13 expression in treatment and control lines, in accordance with an embodiment of the disclosure;

FIG. 8 provides data on the expression of PYL13-3HA-YFP in transgenic plants, in accordance with an embodiment of the disclosure;

FIG. 9 provides data on the inhibition of other PYLs by PYL13, in accordance with an embodiment of the disclosure;

FIG. 10 provides exemplary PYL13 homologs identified according to the *Arabidopsis* phylogenetic tree, in accordance with an embodiment of the disclosure;

Figure 11A:
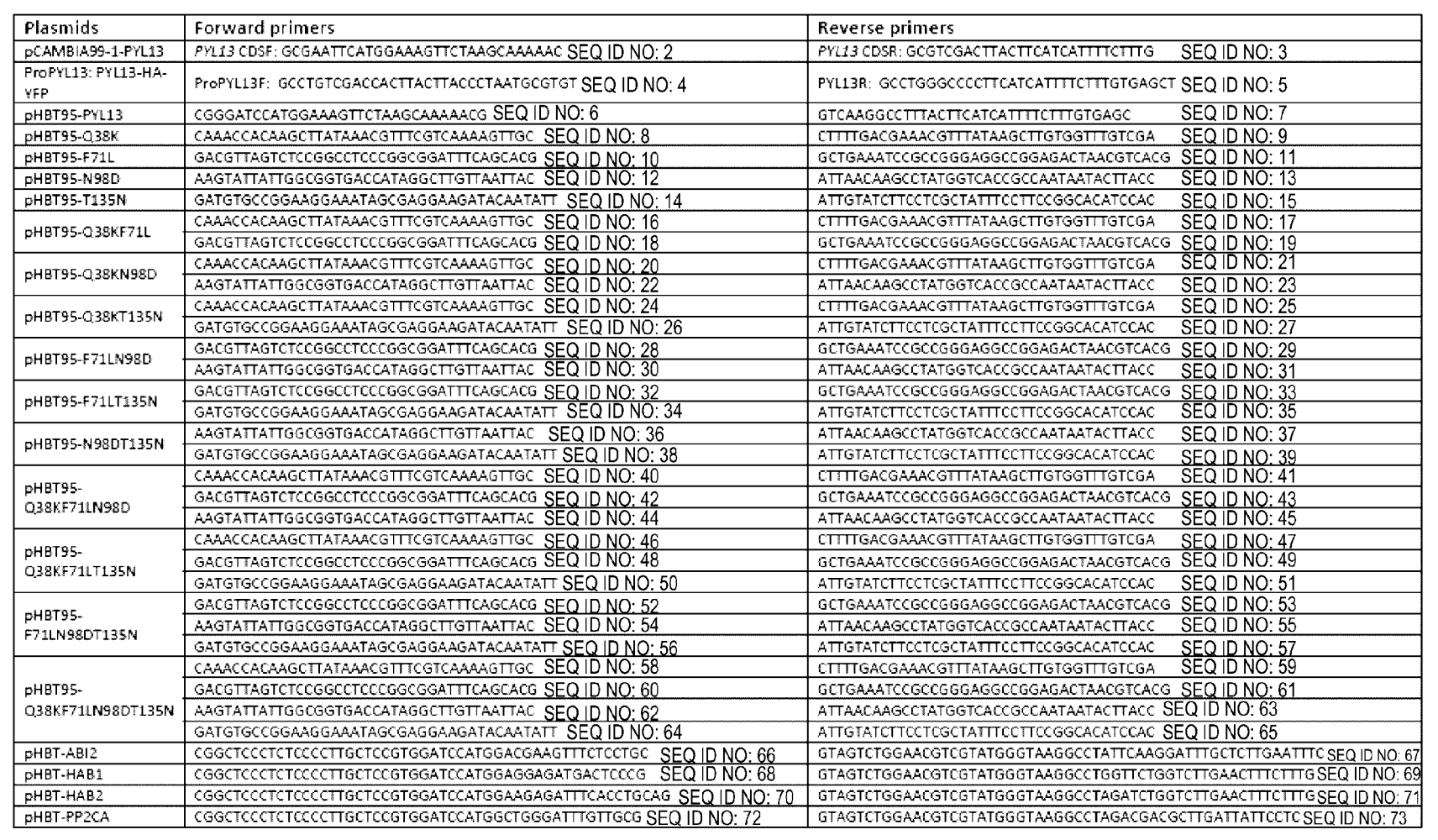

FIGS. 11A and 11B provides exemplary primers for use in constructing the plasmids disclosed herein, in accordance with an embodiment of the disclosure;

FIG. 12 provides data on wild-type and modified PYL13 in the presence of various PP2C enzymes based on the induction of stress-responsive RD29B-LUC expression in the presence and absence of ABA, in accordance with embodiments of the disclosure;

FIG. 13 provides data on PYL9 and PYL11 proteins modified with single point mutations based on the variations identified in PYL13, in accordance with embodiments of the disclosure; and FIGS. 14A and 14B provides data on ABA-independent induction of stress-responsive RD29B-LUC in abi1/abi2/hab1 (A) and abi1hab1pp2ca (B) triple mutant protoplasts that transiently expressed PYL9-K63Q/L89F, PYL11-K39Q/L66F, PYL13 and SnRK2.6.

DETAILED DESCRIPTION

Embodiments of the present disclosure will now be described more fully hereinafter with reference to the accompanying drawings, in which some, but not all, embodiments are shown. Indeed, the invention may be embodied in many different forms and should not be construed as limited to the embodiments set forth herein; rather, these embodiments are provided so that this disclosure will satisfy applicable legal requirements. Additionally, while embodiments are disclosed as "comprising" elements, it should be understood that the embodiments may also "consist of" elements or "consist essentially of" elements. Where possible, any terms expressed in the singular form herein are meant to also include the plural form and vice versa unless explicitly stated otherwise. Also, as used herein, the term "a" and/or "an" shall mean "one or more," even though the phrase "one or more" is also used herein. Like numbers refer to like elements throughout.

Throughout this disclosure, various information sources are referred to and/or are specifically incorporated. The information sources include scientific journal articles, patent documents, textbooks, and websites. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the disclosure.

The present disclosure is based on a newly discovered link between over-expression of PYL13 and drought tolerance in plants. To test the function of PYL13, the interaction of PYL13 with clade A PP2Cs and the effects of PYL13 on the PP2Cs was examined both in vitro and in vivo. PYL13 was found to bind to the PP2Cs and in particular can constitutively inhibit PP2CA in an ABA-independent manner. Unexpectedly, PYL13 interacts with the other PYLs and can reduce the ability of other PYLs to inhibit PP2Cs. Transgenic plants over-expressing PYL13 exhibit improved drought resistance and increased sensitivity to ABA inhibition of germination and postgermination seedling establishment while pyl13 mutant plants are less sensitive to ABA inhibition of postgermination seedling establishment, indicating that PYL13 is functionally important in planta. Further, modifying the other PYL proteins, i.e., PYR1 and PYL1-12, with single point mutations that mimic the variation found in PYL13 based on sequence alignment results in generating mutant PYL proteins that exhibit the same or better effect as over-expression of wild-type PYL13 in plants with respect to expressing stress-tolerance genes.

The present disclosure is directed to providing drought resistance to various plant species. The present disclosure provides a novel transgenic plant and method of producing transgenic plants that have increased drought tolerance. In an embodiment, the transgenic plant has increased expression of a PYL protein, such as PYL13. For example, in an embodiment the transgenic plant has an expression cassette comprising a nucleotide sequence that encodes PYL13. The expression cassette may be a part of a vector transformed into the plant or may be incorporated into the plant DNA. While exemplary nucleotide sequences will be provided herein, it should be understood that additional nucleotide sequences may encode the same protein due to the degeneracy of the DNA code. The transgenic plant may comprise these additional nucleotide sequences in addition to or instead of the nucleotide sequences recited herein. In some embodiments, the expression cassette comprises a promoter and/or additional elements that facilitate the expression or over-expression of the PYL protein in the transgenic plant. Incorporation and expression of the gene or functionally-similar genes can result in drought resistant plants.

In an embodiment, a transgenic plant having increased drought tolerance as compared to a control plant is provided. In an embodiment, the transgenic plant is transformed with a recombinant DNA construct comprising a polynucleotide sequence which comprises a nucleotide sequence encoding a polypeptide that is at least 95% identical to the following amino acid sequence:

```
                                        (SEQ ID NO: 1)
MESSKQKRCRSSVVETIEAPLPLVWSILRSFDKPQAYQRFVKSCTMRSGG

GGGKGGEGKGSVRDVTLVSGFPADFSTERLEELDDESHVMVVSIIGGNHR

LVNYKSKTKVVASPEDMAKKTVVVESYVVDVPEGTSEEDTIFFVDNIIRY

NLTSLAKLTKKMMK
```

For example, the polypeptide may differ at up to 5% of the residues compared to SEQ ID NO: 1 while still retaining the ability to increase drought tolerance in plants. In an embodiment, one or more of the point mutations, e.g., Q38 in CL1, F71 in CL2, and T135 in CL4 as shown in FIG. 6, are conserved in the polypeptide. In an exemplary embodiment, the polypeptide consists of SEQ ID NO: 1. Given that the construct comprises the polynucleotide encoding the polypeptide, additional amino acids may be appended to one or both ends of the polypeptide, whether the polypeptide comprises at least 95% of SEQ ID NO: 1 or consists of SEQ ID NO: 1. In a further embodiment, the transgenic plant exhibits overexpression of PYL13 based on the construct and one or more promoters associated with the polynucleotide sequence.

An exemplary PYL13 coding sequence for the PYL13 polypeptide is as follows:

```
                                        (SEQ ID NO: 148)
ATGGAAAGTTCTAAGCAAAAACGATGTCGCTCTAGCGTAGTCGAGACCAT

TGAAGCACCATTACCACTAGTGTGGTCCATCCTACGTAGTTTCGACAAAC

CACAAGCTTATCAACGTTTCGTCAAAAGTTGCACCATGCGCTCTGGCGGC

GGCGGCGGCAAAGGAGGAGAAGGAAAAGGCTCCGTCCGGGACGTGACGTT

AGTCTCCGGCTTCCCGGCGGATTTCAGCACGGAGAGGCTCGAAGAGCTAG

ATGATGAGTCTCACGTGATGGTGGTAAGTATTATTGGCGGTAACCATAGG

CTTGTTAATTACAAATCGAAAACGAAGGTGGTCGCGTCGCCGGAGGATAT

GGCAAAGAAGACGGTGGTGGTGGAGAGTTACGTGGTGGATGTGCCGGAAG

GAACTAGCGAGGAAGATACAATATTTTTTGTTGATAACATTATTCGGTAT

AACCTTACTTCACTTGCTAAGCTCACAAAGAAAATGATGAAGTAA
```

The transgenic plant may be any type of plant. For example, the transgenic plant may be a monocot or a dicot. As further examples, the transgenic plant may be an angiosperm, a gymnosperm, an algae, etc. In exemplary embodiments, the transgenic plant is a crop, such as a crop that may have a reduced yield when under drought stress. The transgenic plants and methods disclosed herein may increase the yield of the crop plants when under drought stress as compared to control crop plants.

DEFINITIONS

The following terms are used throughout this disclosure:

The term "drought" as used herein refers to the set of environmental conditions under which a plant will begin to suffer the effects of moisture deprivation, such as decreased stomatal conductance and photosynthesis, decreased growth rate, loss of turgor (wilting), or ovule abortion. Plants experiencing drought stress typically exhibit a significant reduction in biomass and yield. Water deprivation may be caused by lack of rainfall or limited irrigation. Further, water deficit may be caused by high temperatures, low humidity, saline soils, freezing temperatures, competition for limited moisture in the rooting zone, or damaged roots. Plant species vary in their capacity to tolerate water deficit and therefore the precise environmental conditions that cause drought stress cannot be generalized. For example CAM plants may experience drought stress under different conditions compared to C3 or C4 plants. However, drought tolerant plants produce higher biomass and yield compared to plants that are not drought tolerant under water limited conditions and may also exhibit enhanced survivability and/or delayed dessication/permanent wilting point under water limited conditions. Differences in physical appearance, recovery, and yield can be quantified and statistically analyzed using known measurement and analysis techniques.

The term "gene" as used herein refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

The term "operably linked" or "operably-linked" as used herein refers to positioning of a regulatory region and a nucleotide sequence to enable influencing transcription initiation or translation initiation or transcription termination of the nucleotide sequence The term "over-expression" as used herein refers to a greater expression level of a gene in a plant, plant cell, or plant tissue, compared to expression a wild-type plant, cell, or tissue, at any developmental or temporal stage for the gene. Over-expression can occur when, for example, the genes encoding one or more polypeptides are under the control of a strong promoter (e.g., the cauliflower mosaic virus 35S transcription initiation region). Over-expression may also be under the control of an inducible, stress-responsive, or tissue-specific promoter. Over-expression may occur throughout the plant, in specific tissue of the plant, or in the presence or absence of particular environmental signals, depending on the promoter used. Over-expression may take place in plant cells normally lacking expression of polypeptides functionally equivalent or identical to the present polypeptides. Over-expression may also occur in plant cells where endogenous expression of the present polypeptide or functionally equivalent molecules normally occurs, but such normal expression is at a lower level. Over-expression results in a greater than normal production, or "overproduction" of the polypeptide in the plant, cell, or tissue.

The term "plant" as used herein includes whole plants, shoot vegetative organs/structures (for example, leaves, stems, and tubers), roots, flowers and floral organs/structures (for example, bracts, sepals, petals, stamens, carpels, anthers, and ovules), seed (including embryo, endosperm, and seed coat), and fruit (the mature ovary), plant tissue (for example, vascular tissue, ground tissue, and the like), and cells (for example, guard cells, egg cells, and the like), and progeny of the same. The class of plants that can be used in the method of the invention generally as broad as the class of higher and lower plants amenable to transformation techniques, including angiosperms (monocotyledonous plants and dicotyledonous plants), gymnosperms, ferns, horsetails, psilophytes, lycophytes, bryophytes, and multicellular algae.

The term "polynucleotide" as used herein is a nucleic acid molecule comprising a plurality of polymerized nucleotides, e.g., at least about five consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and in some embodiments is single-stranded.

The term "polypeptide" as used herein is an amino acid sequence comprising a plurality of consecutive polymerized amino acid residues e.g., at least about five consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, and/or non-naturally occurring amino acid residues.

The term "protein" as used herein refers to an amino acid sequence, oligopeptide, peptide, polypeptide or portions thereof whether naturally occurring or synthetic.

The term "recombinant polynucleotide" as used herein is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector or cassette, or otherwise recombined with one or more additional nucleic acids.

The term "recombinant polypeptide" as used herein is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

The term "regulatory region" as used herein refers to nucleotide sequences that, when operably linked to a sequence, influence transcription initiation or translation initiation or transcription termination of said sequence and the rate of said processes, and/or stability, and/or mobility of transcription or translation product. Regulatory regions include, without limitation, promoter sequences, enhancer sequences, response elements, protein recognition sites, inducible elements, protein-binding sequences, 5' and 3' untranslated regions (UTRs), transcriptional start sites, termination sequences, polyadenylation sequences, and introns. Regulatory regions can be classified into two categories: promoters and other regulatory regions.

The term "transgenic plant" as used herein refers to a plant that contains genetic material not found in a wild-type plant of the same species, cultivar, or variety. The genetic material may include a transgene, an insertional mutagenesis event (such as by transposon or T-DNA insertional mutagenesis), an activation tagging sequence, a mutated sequence, a homologous recombination event, or a sequence modified by chimeraplasty. Typically, the foreign genetic material has been introduced into the plant by human manipulation, but any method can be used as one of skill in the art recognizes. A transgenic plant may contain an expression vector or cassette. The expression cassette typically comprises a polypeptide-encoding sequence operably linked to appropriate inducible or constitutive regulatory sequences that allow for the expression of a polypeptide. The expression cassette can be introduced into a plant by transformation or by breeding after transformation of a parent plant.

The term "wild-type" or "wild type" as used herein refers to a plant cell, seed, plant component, plant tissue, plant organ, or whole plant that has not been genetically modified or treated in an experimental sense. Wild-type cells, seed, components, tissue, organs, or whole plants may be used as controls to compare level of expression and the extent and nature of trait modification with cells, tissue, or plants of the same species in which a polypeptide's expression is altered, e.g., in that is has been knocked out, over-expressed, or ectopically expressed.

INCREASING DROUGHT TOLERANCE IN PLANTS

PYL13 Differs from the Other PYLs and does not Function as an ABA Receptor

The PYL family contains fourteen members. Although previous studies suggested that many are ABA receptors and have redundancy (Park et al., 2009), they also showed functional differences (Hao et al., 2011). In the presence of ABA, the proteins PYR1 and PYL1-12 reduced the activity of ABI1 and activated SnRK2.6 to induce RD29B-LUC expression in *Arabidopsis* protoplasts (Fujii et al., 2009).

To test whether PYL13 can act as an ABA receptor, the ABA signaling pathway in wild-type protoplasts was reconstituted. Turning now to FIG. 1, wild-type (Col-0) protoplasts were used in both panels A and B. After transfection, the protoplasts were incubated for 4.5 hours under light in the absence of ABA (open bars) or in the presence of 5 μM ABA (closed bars). Error bars indicate s.e.m. (n=3). The addition of PYL2 inhibited ABI1 activity and enabled the expression of ABA-dependent induction of the ABA-responsive reporter RD29B-LUC (FIG. 1A). However, cotransfection of PYL13 with ABI1, SnRK2.6, and ABF2 did not enable the expression of RD29B-LUC (FIG. 1A). ZmUBQ-GUS was used as the internal control. PYL13 cannot antagonize the ability of ABI1 to inhibit the ABA-dependent induction of RD29B-LUC expression in protoplasts. Instead, the ABA signaling pathway was reconstituted by co-expression of PYLs, ABI1, SnRK2.6, and ABF2. The results suggest that PYL13 is a unique member of the PYL family and cannot function as an ABA receptor. Therefore, the response of other members of the PYL family would not predict the response of PYL13 expression or over-expression in plants.

As noted earlier, the ABA-binding pocket in PYLs consists of four highly conserved regions named CL1-4 (Yin et al., 2009). Amino acid sequence alignment shows that PYL13 differs from other PYLs in key residues in CL1-4 (Q38 in CL1, F71 in CL2, N98 in CL3, and T135 in CL4; FIG. 6). As shown in FIG. 6, PYL13 has a glutamine at residue 38. In contrast, PYR1 and PYL1-12 have a lysine at the same position based on the sequence alignment shown in FIG. 6. Similarly, PYL13 has a phenylalanine at residue 71 but the other PYL proteins have leucine; PYL13 has an asparagine at residue 98 but the other PYL proteins have aspartic or glutamic acid (both electrically charged negative amino acids); and PYL13 has threonine at residue 135 but the other PYL proteins have asparagine. These differences between PYL13 and the other PYL proteins may explain why PYL13 is ABA-independent while the other PYL proteins initiate expression of stress-tolerance genes primarily in the presence of ABA.

To test whether these sequence variations may explain the functional difference of PYL13, point mutations (Q38K, F71L, N98D, and T135N) were introduced to PYL13 to mimic the other PYLs, and these mutated PYL13 were transfected together with ABI1, SnRK2.6, and ABF2 in protoplasts. None of the single mutations in PYL13 could mimic PYR1 in elevating RD29B-LUC expression. Double mutations (Q38K/F71L), triple mutations (Q38K/F71L/N98D and Q38K/F71L/T135N), and quadruple mutations (Q38K/F71L/N98D/T135N) of PYL13 could partially confer an ABA-dependent induction of RD29B-LUC expression (FIG. 1B). Q38 and F71 in CL1-2 appear to be the most important residues because PYL13 with these two residues mutated became largely functional in the reconstitution assay. N98 in CL3 appears to be not important, and the T135N mutation in CL4 could enhance the ability of PYL13 mutants to inhibit ABI1 activity in the presence of ABA. Without wishing to be bound by theory, these results suggest that three amino acid variations (Q38 in CL1, F71 in CL2, and T135 in CL4) can explain the inability of PYL13 to act as an ABA receptor.

Over-Expression of PYL13 Confers Drought Resistance in *Arabidopsis*

A previous study showed that over-expression of PYL5 leads to an enhanced response to ABA and to drought resistance (Santiago et al., 2009b). In this study, however, the plants were subjected to drought stress, which elevated the endogenous ABA and initiated the expression of stress-tolerance genes via the PYL-PP2C binding. Given that PYL13 does not function as an ABA receptor, it is not obvious that the PYL13 will have any function, let alone the same function of PYL5, in plants. Further, initiating the expression of stress-tolerance genes without elevated ABA levels via PYL13 over-expression may have benefits. For example, plants may not need to be under stress and thus have elevated ABA levels prior to expressing stress-tolerance genes. In this manner, plants may be pre-conditioned to tolerate stress conditions before the plants experience the stress conditions. Faster recovery from stress conditions, such as drought, may also occur.

To test the function of PYL13 over-expression, PYL13 over-expression (OE-PYL13) lines were generated, and three homozygous T3 lines were chosen for phenotypic analysis. Northern blot analysis indicated that PYL13 transcripts were obviously more abundant in OE-PYL13 lines than in the wild type (FIG. 7).

Turning now to FIG. 2, in an embodiment over-expression of PYL13 confers drought tolerance. For example, OE-PYL13 lines exhibited an improved drought resistance (FIG. 2A). Fourteen-day-old plants were subjected to drought treatment. The representative photographs in FIG. 2A show plants before drought treatment, after drought treatment, and without drought treatment. The "after drought treatment" plants were photographed two days after watering was resumed. After a 24-day drought treatment in soil, more than 80% of OE-PYL13 transgenic plants survived and fewer than 20% of the wild-type plants survived (FIG. 2B). The surviving plants were counted two days after watering was resumed. Error bars indicate s.e.m. (n=3). The greater drought-stress survival of OE-PYL13 lines was associated with reduced water loss from leaves of the OE-PYL13 lines. Cumulative transpiration water loss from rosette leaves detached at the same developmental stage was slower in OE-PYL13 lines than in the wild type (FIG. 2C). Error bars indicate s.e.m. (n=3). To characterize the drought resistance in OE-PYL13 transgenic plants, several physiological parameters were determined based on three independent transgenic lines. When water was withheld for 5 days, transgenic plants over-expressing PYL13 showed a slower transpiration rate than wild-type plants (FIG. 2D) and this was accompanied with a reduced stomatal conductance (FIG. 2E). The photosynthetic rate (FIG. 2F) and water-use efficiency (FIG. 2G) were greater in OE-PYL13 lines than in the wild type. Error bars indicate s.e.m. (n=3). These results demonstrate that over-expression of PYL13 unexpectedly and significantly confers drought resistance in *Arabidopsis*.

Over-Expression of PYL13 Promotes Stress-Responsive Gene Expression

To further characterize the PYL13 over-expression lines, the expression of stress responsive genes including RD29A, KIN1, COR15A, and RAB18 in the transgenic plants (FIG. 2H) was evaluated. Quantitative RT-PCR was conducted on samples with 100 μM ABA treatment for 0 min, 20 min, 40 min, 1 h, 2 h, 3 h, 6 h, and 10 h. The expression levels of RD29A, KIN1, COR15A and RAB18 in Col-0 before ABA treatment were set as 1. Error bars indicate s.e.m. (n=3).

Under the unstressed control condition, the transcript levels of the four tested stress-responsive genes were 2- to 6-fold higher in the OE-PYL13 lines than in the wild type Col-0. Expression of RD29A, KIN1, COR15A, and RAB18 was induced by ABA treatment in the OE-PYL13 transgenic lines as well as in Col-0. However, the levels of RD29A, KIN1, and COR15A were higher in OE-PYL13 seedlings than in Col-0 seedlings at early time points (e.g. 20 and 40 min) after ABA treatment. At later time points (e.g. 6 h), the levels of RD29A, KIN1, COR15A, and RAB18 in OE-PYL13 seedlings was similar to that in Col-0 seedlings. These results indicate that over-expression of PYL13 accelerates stress responsive gene expression in plants.

PYL13 Interacts with Clade A PP2Cs in an ABA-Independent Manner

To investigate how PYL13 may function in plants, the interaction between PYL13 and clade A PP2Cs in yeast two-hybrid assays was examined, as shown in FIG. 3. The results show that PYL13 binds to all PP2Cs tested in an ABA-independent manner (FIG. 3A). PYL13 binds strongly with ABI1, ABI2, PP2CA, and HAI2 but weakly with HAB1 and HAI1 (FIG. 3A). As shown in FIG. 3A, PYL13 interacts with clade A PP2Cs in a yeast two-hybrid assay. PYL13 fused to the GAL4-DNA-binding domain (BD) was used as prey, and PP2Cs fused to the GAL4-activating domain (AD) were used as baits. Interaction was determined by growth assay on media lacking His and His/Ade in the presence and absence of ABA. Dilutions ($10^{-1}$, $10^{-2}$, and $10^{-3}$) of saturated cultures were spotted onto the plates, which were photographed after 5 days.

These results were confirmed in pull-down assays with purified recombinant proteins, in which PYL13 interacted with all PP2Cs tested in an ABA-independent manner while PYR1 interacted with ABI1 in an ABA-dependent manner (FIG. 3B). In the pull-down assay, PYL13 binding was much stronger with PP2CA than with AHG1, ABI1, or ABI2 (FIG. 3B). As shown in FIG. 3B, recombinant PYL13 binds to clade A PP2Cs in an ABA-independent manner. His-tagged PYL13 (~22 kD) and His-tagged PYR1 (~25 kD) were used to pull down PP2Cs without tag. PYL13 interacted with PP2CA, AHG1, ABI1, and ABI2 independent of ABA while PYR1 interacted with ABI1 in the presence of 200 μM ABA.

To determine whether PYL13 and PP2Cs may interact in an ABA-independent manner in vivo, c-myc-tagged PYL13 and hemagglutinin (HA)-tagged PP2Cs were co-expressed in protoplasts. Coimmunoprecipitation (co-IP) assays using ABI1-HA and PP2CA-HA as baits captured c-myc-PYL13 in an ABA-independent manner (FIG. 3C). The binding of PP2CA with PYL13 again appeared much stronger than that of ABI1 with PYL13. These results demonstrated that PYL13 constitutively binds to clade A PP2Cs but that the binding intensity differs among clade A PP2Cs. The ABA-independent binding of PYL13 with PP2CA and ABI1 in protoplasts is shown in FIG. 3C. Total soluble proteins (input) were extracted from *Arabidopsis* protoplasts that transiently expressed the indicated constructs. PP2C-interacting proteins were immunoprecipitated with anti-HA mouse antibodies and detected with anti-HA and anti-cMYC rabbit antibodies.

Although PYL10 also forms stable complexes with ABI1 in the absence of ABA, the binding of PYL10 to ABI1 is much stronger in the presence than in the absence of ABA (Hao et al., 2011). In contrast, interactions between PYL13 and PP2C were unaffected by ABA, i.e., these interactions are completely ABA-independent.

PYL13 Differentially Inhibits Clade A PP2Cs in an ABA-Independent Manner and is Important for Seed Germination PYL13 interacts with all clade A PP2Cs tested but binds most strongly to PP2CA. To investigate whether PYL13 inhibits PP2Cs in planta, PYL13 was co-expressed with all clade A PP2Cs in wild-type protoplasts, as shown in FIG. 4. Transfections of all PP2Cs together with SnRK2.6 and ABF2 inhibited RD29B-LUC expression to different degrees, see FIG. 4A, and the degree of inhibition was correlated with the intensity of interaction between PP2Cs and SnRK2.6 (Fujii et al., 2009). As shown in FIG. 4A, inhibition of RD29B-LUC expression by PP2CA, HAI2, and HAI3 was antagonized by PYL13 in wild-type protoplasts. The ABA signaling pathway was reconstituted by co-expression of PYLs, PP2Cs, SnRK2.6, and ABF2. RD29B-LUC was used as the ABA-responsive reporter. ZmUBQ-GUS was used as the internal control. After transfection, protoplasts were incubated for 4.5 h under light in the absence of ABA (open bars) or in the presence of 5 μM ABA (closed bars). Error bars indicate s.e.m. (n=9).

As an example, the PP2C interaction intensities with SnRK2.6 were ABI1>HAB1>ABI2 in yeast two-hybrid (Y2H) assays, and the inhibition of RD29B-LUC expression was greater for ABI1 than HAB1 and was greater for HAB1 than for ABI2 in the protoplast experiments (FIG. 4A). Co-transfections of PYL13 together with ABI1, ABI2, HAB1, HAB2, or AHG1 did not enable RD29B-LUC expression, but co-transfections of PYL13 with PP2CA, HAI2, or HAI3 enabled the ABA-dependent induction of RD29B-LUC expression (FIG. 4A). In the control experiments, co-transfections of PYR1 and PYL2 with ABI1 restored RD29B-LUC expression (FIG. 4A). These results indicated that PYL13 inhibits the phosphatase activities of PP2CA, HAI2, and HAI3. The ABA-responsiveness of the PYL13-transfected protoplasts as well as of the protoplasts without any transfected PYLs was presumably due to the activities of endogenous PYLs present in the protoplasts.

To investigate the underlying mechanism by which PYL13 differentially inhibits the function of PP2Cs, the effects of PYL13 on the phosphatase activities of purified PP2Cs was evaluated with and without ABA. The results showed that PYL13 acts as a strong constitutive inhibitor of PP2CA phosphatase activity and a weak inhibitor of ABI1 activity but has almost no inhibitory activity against ABI2 at the molar ratio of 1:1 (FIG. 4B). The inhibition by PYL13 is ABA-independent, whereas the inhibition by PYR1 and PYL2 is ABA-induced (FIG. 4B). The activities of clade A PP2Cs were differentially inhibited by PYL13 independently of ABA. The phosphatase activities of PP2CA, ABI1, and ABI2 were measured in the absence or presence of ABA (1.25 µM), and with or without PYLs. The concentration of PP2Cs and PYLs was 0.3 µM. The $A_{405}$ value of reaction without PP2C was set as 0% and that of the reaction with PP2C but without ABA and PYLs was set as 100%. Error bars indicate s.e.m. (n=6 for PP2CA and ABI2, and n=3 for ABI1).

As shown in FIG. 4B, PYL13 reduced PP2CA phosphatase activity to 55±5% without ABA and to 54±5% with 1.25 µM ABA, and reduced ABI1 phosphatase activity to 75±3% without ABA and to 75±3% with 1.25 µM ABA. In contrast, PYL13 only reduced ABI2 phosphatase activity to 89±8% without ABA and to 93±6% with 1.25 µM ABA, and this level of activity did not differ from that in the buffer control with ABA (93±5%). These results show that PYL13 differentially inhibits the phosphatase activities of PP2Cs in an ABA-independent manner. One skilled in the art would not expect the results from the ABA-dependent PYL proteins to apply to PYL13.

The basal RD29B-LUC expression level was elevated in protoplasts co-transfected with PP2CA-PYL13, HAI2-PYL13, or HAI3-PYL13, which is consistent with PYL13 inhibition of these PP2Cs in an ABA-independent manner in vivo (FIG. 4A). To exclude interference by endogenous PP2Cs in wild type protoplasts and to assess the ABA-independent selective inhibition of PP2Cs by PYL13, PYL13 was co-expressed with PP2CA, HAI1, HAI2, and HAI3 in abi1/hab1/abi2 triple mutant protoplasts, as shown in FIG. 4C. After transfection, protoplasts were incubated for 4.5 h under light in the absence of ABA. Error bars indicate s.e.m. (n=3). This mutant is deficient in ABI1, HAB1, and ABI2 but does not show strong constitutive activation of SnRK2.2/2.3/2.6 (Fujii et al., 2009). Expression of RD29B-LUC in the absence of ABA was increased in the co-transfections of PP2CA-PYL13, HAI2-PYL13, or HAI3-PYL13 together with SnRK2.6 and ABF2 but an increase was not observed in the control transfections of PYL13-HAI1 or PYL2-PP2CA (FIG. 4C). The quadruple mutation Q38K/F71L/N98D/T135N abolished the ability of PYL13 to elevate RD29B-LUC expression in the absence of ABA, indicating that the four amino acid variations are responsible for the ABA-independent inhibition of PP2Cs by PYL13 (FIG. 4C). These data further suggested that PYL13 inhibits PP2CA, HAI2, and HAI3 in an ABA-independent manner in vivo.

Over-expression of AtPP2CA resulted in ABA insensitivity while knockout of AtPP2CA caused ABA hypersensitivity during seed germination (Kuhn et al., 2006). Given the strong inhibition by PYL13 on PP2CA activity in vitro and in vivo, PYL13 over-expression was investigated to determine whether PP2CA function in planta is impacted. Seed germination of PYL13 over-expression lines on MS medium containing 0.0, 0.5, or 1 µM ABA was evaluated. The panels show the percentage of seeds with emerged radical. Error bars indicate s.e.m. (n=3). In the absence of exogenous ABA, OE-PYL13 seeds germinated as well as wild-type seeds (FIG. 4D, left panel). In the presence of 0.5 µM ABA, the germination of OE-PYL13 #1 was greatly inhibited by ABA (FIG. 4D, middle panel). In the presence of 1 µM ABA, ABA-hypersensitive inhibition of seed germination was observed for OE-PYL13 #1 and OE-PYL13 #7 (FIG. 4D, right panel). Postgermination seedling establishment inhibition at 0.2 µM ABA level was observed for OE-PYL13 #1 (FIG. 4F). The germination sensitivity to ABA was correlated with the expression level of PYL13, as shown in the Northern blot analysis in FIG. 7. Ethidium bromide stained rRNA bands are shown as the loading control. In contrast, pyl13-1 (SALK_041176) and pyl13-2 (SALK_071488) mutants (FIG. 4E) are less sensitive to ABA inhibition of postgermination seedling establishment (FIG. 4F). The open box in FIG. 4E indicates exon. The two T-DNA insertions are also indicated. FIG. 4F shows seedling establishment of the wild type, pyl13 mutants, and OE-PYL13 transgenic line in MS medium and MS plus 0.2 µM ABA. The panels show the percentage of seeds that developed green cotyledons. Error bars indicate s.e.m. (n=3).

The genetic results are consistent with the observation of PYL13 inhibition of PP2CA and the known function of PP2CA in seed germination and postgermination seedling establishment.

PYL13 Interacts with and Antagonizes Other PYLs

To further investigate the molecular mechanism of PYL13 function in plants, transgenic Arabidopsis plants expressing tagged PYL13 under the native PYL13 promoter (ProPYL13: PYL13-HA-YFP (FIG. 8A) were generated. FIG. 8A provides an analysis of YFP expression in ProPYL13: PYL13-HA-YFP lines using Northern blotting. Ethidium bromide stained rRNA bands are shown as the loading control. Purified PYL13-associated proteins were also generated using anti-GFP-agarose in extracts of floral organs of the transgenic plants (FIG. 8B). PYL13-HA-YFP protein was detected with anti-GFP mouse antibodies (ROCHE). PYL13-associated proteins were identified by mass spectrometric analyses. The associated proteins included not only PP2CA and HAI1 but also PYL2 and PYL9. While the result confirmed the interaction of PYL13 and PP2Cs in planta (FIG. 3), it also raised the possibility of PYL13 interaction with and affecting the activities of other PYLs.

To confirm the interaction between PYL13 and PYL2/PYL9 and to determine whether PYL13 may bind with other PYLs, the interaction of PYL13 with PYLs was examined in yeast two-hybrid assays, as shown in FIG. 5. In this experiment, PYL13 interacted with PYR1, PYL1-4, PYL6, and PYL11-12 in an ABA-independent manner (FIG. 5A). PYL13 fused to the GAL4-activating domain (AD) was used as prey, and PYLs fused to the GAL4-DNA binding domain (BD) were used as baits. Interaction was determined by growth assay on media lacking His and His/Ade in the presence and absence of ABA. Dilutions ($10^{-1}$, $10^{-2}$, and $10^{-3}$) of saturated cultures were spotted onto the plates, which were photographed after five days. These results thus confirmed the interaction between PYL13 and PYL2 identified in immunoprecipitation and mass spectrometric experiments, but failed to detect an interaction between PYL13 and PYL9. Without wishing to be bound by theory, the lack of interaction between PYL14 and PYL9 may be caused by the cellular differences between yeast and *Arabidopsis* or because of indirect interactions between the two proteins in *Arabidopsis*.

To further characterize the interactions between PYL13 and PYLs in vivo, their interactions in protoplasts were examined by the firefly luciferase (LUC) complementation assay. PYL13 was fused to the C-terminal domain of LUC (PYL13-cLUC), and PYLs were fused to the N-terminal domain of LUC (PYLs-nLUC), and co-expressed in protoplasts. After transfection, protoplasts were incubated overnight under light at room temperature, and the LUC activities in living protoplasts were measured. Error bars indicate s.e.m. (n=6). The relative LUC activities were measured, and the results suggested that PYL13 binds to all PYLs tested but with different intensities (FIG. 5B). PYL13 binds more strongly to PYR1, PYL1-5, PYL7, and PYL10-11 than to PYL6, PYL8-9, or PYL13 (FIG. 5B).

The direct interactions between PYL13 and two of the PYLs were also verified in pull-down assays with purified recombinant proteins. GST-tagged PYL1 (~51 kD) and PYL2 (~46 kD) were pulled down by His-tagged PYL13 (~22 kD) in an ABA-independent manner (FIG. 5C). Previous structural and biochemical investigations demonstrated that several PYLs (such as PYR1, PYL1, PYL2, PYL3) form homo-dimers in solution and that the dimer formation is important in regulating ABA binding and PP2C interactions (Hao et al., 2011; Santiago et al., 2009; Yin et al., 2009). These results indicate that PYL13 can form heterodimers with other PYLs.

To test the functional significance of potential heterodimer formation between PYL13 and other PYLs, the abilities of PYL1 and PYL2 and the protein complexes PYL13-PYL1 and PYL13-PYL2 to inhibit the phosphatase activity of ABI1 were compared using purified recombinant proteins and the synthetic phosphatase substrate pNPP. The results show that inhibition of ABI1 in the presence of ABA was less for the PYL13-PYL dimers than for the PYLs alone (FIG. 5D). The phosphatase activity of ABI1 was measured (using pNPP) in the absence or presence of 10 µM ABA, with or without PYLs, and with PYL13-PYL dimers. The concentration of ABI1 and PYLs was 0.3 µM. The $A_{405}$ value of reaction without ABI1 was set as 0% and that of the reaction with ABI1 but without ABA and PYLs was set as 100%. Error bars indicate s.e.m. (n=6). In the presence of 10 µM ABA, ABI1 phosphatase activity was reduced to 67±6% by PYL1 but only to 88±8% by PYL13-PYL1. In the presence of 10 µM ABA, ABI1 phosphatase activity was reduced to 50±3% by PYL2 but only to 78±10% by PYL13-PYL2. These results indicate that, by forming heterodimers, PYL13 can reduce the ability of PYL1 and PYL2 to inhibit the phosphatase activity of ABI1 in vitro.

To investigate the physiological significance of the binding between PYL13 and PYLs in vivo, PYL13 was co-expressed with one of the other PYLs, ABI1, SnRK2.6, and ABF2 in wild-type protoplasts. When the transfected PYL13 plasmid was 2-fold of that of the other PYLs, co-transfections with PYL13 decreased the activity of the ABA-responsive PYLs (FIG. 5E). The designation "2×PYL13" indicates that the concentration of PYL13 plasmids was two-fold greater than that of PYL2 plasmids. ZmUBQ-GUS was used as the internal control. After transfection, protoplasts were incubated for 4.5 h under light in the absence of ABA (open bars) or in the presence of 5 µM ABA (closed bars). Error bars indicate s.e.m. (n=3).

As shown in FIG. 9, the level of inhibition by PYL13 depended on the PYL and ranged from 27% with PYL2 to 67% with PYL1. The ABA signaling pathway was reconstituted by co-expression of PYL13, PYLs, ABI1, SnRK2.6, and ABF2. The designation "2×PYL13" indicates that the concentration of PYL13 plasmids was two-fold greater than that of PYL2 plasmids. Error bars indicate s.e.m. (n=3). These results indicated that PYL13 can antagonize the activity of other PYLs in plants. Without wishing to be bound by theory, PYL13 inhibition of other PYLs might result from direct interactions between PYL13 and other PYLs or from competition for the binding sites on PP2Cs.

SUMMARY

PYL13 has dual roles in *Arabidopsis*. In one role, PYL13 serves as a positive regulator of ABA signaling. Yeast two-hybrid, pull-down, and co-IP assays demonstrated that PYL13 interacts with all clade A PP2Cs in an ABA-independent manner (FIG. 3). Phosphatase activity assays showed that PYL13 strongly inhibits PP2CA in an ABA-independent manner (FIG. 4B). The inhibitory mechanism of PYL13 differs from that previously reported for PYL5-PYL10, which also interact with and inhibit PP2C activity in the absence of ABA (Hao et al., 2011; Park et al., 2009). Although these PYLs have high basal activities, ABA can enhance their interaction with PP2Cs and their inhibition of PP2C phosphatase activity (Hao et al., 2011). However, ABA has no effect on PYL13 (FIGS. 3 and 4A). The inhibition of PP2CA phosphatase activity by PYL13 with or without ABA is indistinguishable from that of PYR1/PYL2 with ABA (FIG. 4B). These results are supported by the reconstitution of ABA signaling in protoplasts and by the phenotypes of the PYL13 over-expression transgenic plants (FIGS. 4A, 4C and 4D).

PYL13 can inhibit PP2CA activity in vivo (FIG. 4C). When PYL13 was co-transfected with PP2CA, HAI2, or HAI3 in abi1/hab1/abi2 protoplasts, the basal expression of RD29B-LUC in the absence of ABA was enhanced (FIG. 4C). The PYL13 quadruple mutant Q38K/F71L/N98D/T135N lost the ABA-independent induction of the RD29B-LUC basal expression level (FIG. 4C), suggesting that it is these sequence variations that confer ABA-independent inhibition of PP2CA, HAI2, and HAI3. Moreover, the phenotype of PYL13 over-expression lines is similar to that of pp2ca knockout mutants (Kuhn et al., 2006), whose seed germination is hypersensitive to ABA (FIG. 4D). Consistently, the phenotype of pyl13 mutants is in the same pattern as PP2CA over-expression lines (Kuhn et al., 2006), whose seedling establishment is hyposensitive to ABA (FIG. 4F).

These results suggest that PYL13 acts as a constitutive activator of ABA signaling to maintain a higher basal level of ABA signaling under unstressed conditions and to enhance stress responses under stressed conditions, which would be advantageous in dealing with the unpredictable environmental changes. Indeed, transcripts of RD29A, KIN1, COR15A, and RAB18 were more abundant in OE-PYL13 seedlings than in the wild type Col-0 under unstressed conditions and the stress responses were accelerated in OE-PYL13 seedlings under ABA treatments (FIG. 2H). Thus, the improved drought resistance of over-expression of PYL13 plants (FIG. 2) may be explained by PYL13 inhibition of the PP2Cs in leaf tissues including the guard cells. The fact that no significant defects were observed in drought resistance in pyl13 mutant plants suggests that PYL13 may not have significant expression and/or function in guard cells.

In its second role, PYL13 antagonizes other ABA-responsive PYLs. PYL13 can interact with other PYLs independent of ABA in immunoprecipitation and mass spectrometric analyses, yeast two-hybrid assays (FIG. 5A), LUC complementation (FIG. 5B), and protein pull-down assays (FIG. 5C). PYL13 can moderately reduce the activities of other PYLs in the presence of ABA as indicated by the analysis of ABI1 phosphatase activity (FIG. 5D) and protoplast assays (FIG. 5E). At later time points after ABA treatments, the stress-responsive genes maintain a similar expression level in OE-PYL13 transgenic plants and in wild-type plants (FIG. 2H). These results are consistent with the notion that PYL13 may rein in or desensitize ABA responses by antagonizing the ABA receptors. By acting as a "constitutive activator" (role 1) and a moderate antagonist of other PYLs (role 2), PYL13 may help maintain ABA signaling within a reasonable range.

Over-expression of CBF1 induces COR genes and confers freezing tolerance (Jaglo-Ottosen et al., 1998). Over-expression of DREB1A/CBF3 induces DREB1, DREB2, and RD29A genes and confers increased resistance to drought, high-salt, and freezing stresses (Liu et al., 1998). Although OE-OsMYB3R-2 exhibited enhanced cold tolerance in rice, it also resulted in growth retardation under normal conditions (Ma et al., 2009a). Similarly, OE-DREB1A in *Arabidopsis* caused severe growth retardation (Liu et al., 1998), and over-expression of CBF1 in tomato resulted in a dwarf phenotype (Hsieh et al., 2002). These results indicate that constitutive activation of stress responsive genes increases stress tolerance but may also result in growth retardation. Thus, constitutive activation of stress-responsive genes may not be suitable for crop improvement. However, over-expression of PYL13 did not result in any abnormal growth phenotype under normal conditions. This unexpected result indicates that transgenic plants of the current disclosure perform significantly better than alternative methods of providing drought resistance or increased stress tolerance. Under normal conditions, expression of the stress-responsive genes was only slightly higher in OE-PYL13 lines than in the wild type. Under stress conditions, however, these genes were induced more quickly in OE-PYL13 lines than in the wild type.

PYL13 differs from other PYLs in the highly conserved ABA-binding pocket CL1-4. Q38 differs from K in CL1, F71 differs from L in CL2, N98 differs from D/E in CL3, and T135 differs from N in CL4 (FIG. 6). The residues Q38, F71, N98, and T135 are different in PYL13 (indicated by the single-residue rectangular boxes) than in other PYLs in *Arabidopsis*. Q38 is located in conserved loop (CL) 1, F71 is located in CL2, N98 is located in CL3, and T135 is located in CL4. These conserved loops (indicated by C-labeled rectangular boxes) are important for ABA-binding, dimer formation of PYLs, and interaction of PYL with PP2C (Yin et al, 2009). PYLs from *Arabidopsis* were aligned using ClustalX 2.0.5 (Larkin et al, 2007) with the default settings and were viewed using the GeneDoc software, Nicholas, K. B., Nicholas H. B. Jr., and Deerfield, D. W. II. 1997, *GeneDoc: Analysis and Visualization of Genetic Variation*, EMBNEW.NEWS 4:14.

Q38K, F71L, N98D, and T135N were mutated on PYL13 to mimic other PYLs. None of these single mutants could mimic PYR1 or PYL2 with respect to the activation of RD29B-LUC expression in protoplasts. Double mutations of PYL13 (Q38K/F71L) and triple mutations (Q38K/F71L/ N98D) could partially confer ABA-dependent induction of RD29B-LUC expression (FIG. 1B).

Without wishing to be bound by theory, the residues Q38 and F71 in CL1-2 contribute to the unique mode of action of PYL13 and are conserved in the genus *Arabidopsis* (FIG. 10). Further, T135 in CL4 can enhance the effect of Q38K/ F71L in inhibiting ABI1 in the presence of ABA. These results suggest that the variations in the three residues (Q38 in CL1, F71 in CL2, and T135 in CL4) can explain the functional difference between PYL13 and the other PYLs, which are ABA receptors. The PYL13 homologs were aligned using ClustalX 2.0.5 with the default settings, and viewed using GeneDoc software.

As discussed, PYL13 differs from other PYLs at the Q38 and F71 residue. In FIG. 12, relative luciferase activity generated from stress-tolerance reporters in the presence and absence of 5 µM ABA is provided. FIG. 12 shows PYL13 having Q38K and/or F71L point mutations and optionally including SnRK2.6 and various PP2C enzymes (e.g., AHG1, PP2CA, HAI3, HAI2, HAI1, HAB2, HAB1, ABI2, and ABI1). As shown, PYL13 cannot antagonize the ability of ABI1, HAB1, HAB2, HAI1 and AHG1 to inhibit the ABA-dependent induction of RD29B-LUC expression in protoplasts. The ABA signaling pathway was reconstituted by co-expression of PYL13, ABI1, SnRK2.6, and ABF2. Wild-type (Col-0) protoplasts were used. RD29B-LUC was used as the ABA-responsive reporter. ZmUBQ-GUS was used as the internal control. After transfection, protoplasts were incubated for 4.5 h under light in the absence of ABA (open bars) or in the presence of 5 µM ABA (closed bars). Error bars indicate s.e.m. (n=3).

To confirm that the inability of PYL13 to act as an ABA receptor is mainly contributed by the two amino acid variations (Q38 in CL1 and F71 in CL2), the mutated PYL13-Q38K/F71L was transfected together with all clade-A PP2Cs, SnRK2.6, and ABF2 in wild type Col-0 protoplasts. The Q38K/F71L double mutations of PYL13 conferred an ABA-dependent induction of RD29B-LUC expression with ABI1, HAB1, HAB2, HAI1, and AHG1 (FIG. 12). The Q38K/F71L mutations also enhanced the ability of PYL13 mutants to inhibit PP2CA, HAI2, HAI3 and ABI2 activity in the presence of ABA (FIG. 12). These data confirmed that Q38 and F71 variations confer PYL13 functions different from other PYLs.

The results suggest that PYL13 is not an ABA receptor but that it can inhibit both the PYL receptors and the PP2C co-receptors. The novel functions of PYL13 make it an important modulator of ABA signaling. Because over-expression of PYL13 increases drought resistance, relative photosynthetic rate, and water-use efficiency in transgenic plants, this ABA receptor variant is useful for increasing the drought resistance of crops. Thus, transgenic plants and methods of increasing stress tolerance in plants are provided when over-expressing PYL13.

FIG. 13 provides data relating to an alternative approach to providing transgenic plants and methods of increasing stress tolerance in plants. Shown in FIG. 14, when the Q38 and F71 variations in PYL13 were introduced into other PYL proteins, these PYL mutants gained the ability to initiate ABA-independent activation of a stress responsive reporter. This suggests that transgenic plants that express modified PYL proteins, such as PYL proteins modified with the Q38K and/or F71L variation, may have improved drought tolerance. It should be understood that the position of the modified residue in other PYL proteins may differ from the $38^{th}$ or $71^{st}$ residue in PYL13 but that one skilled in the art could identify the appropriate residue given the sequence alignment, as shown in FIG. 6.

To gain transgenic lines with better drought tolerance, mutations on other PYLs were made to mimic PYL13's variation. FIG. 13 depicts PYL9 and PYL11 mutants that were modified with the variations identified in PYL13. Point mutations (K63Q/L89F in PYL9, and K39Q/L66F in PYL11) were made to PYL9 and PYL11 to mimic Q38 and F71 variations in PYL13, and these mutated PYLs were transfected together with ABI1, SnRK2.6, and ABF2 in protoplasts. Specifically, PYL9 was modified at the 63$^{rd}$ residue from a K to a Q amino acid, analogous to the Q38 variation in PYL13. Similarly, PYL9 was modified at the 89$^{th}$ residue from an L to an F amino acid, analogous to the F71 variation in PYL13. In PYL11, the 39$^{th}$ residue was changed from a K to a Q amino acid and the 66$^{th}$ residue was changed from an L to an F, again analogous to the variations seen in PYL13.

The PYL9-K63Q/L89F and PYL11-K39Q/L66F mutations mimicked PYL13 on the inability to act as an ABA receptor in the presence of ABI1 (FIG. 13). These results confirmed that Q38 and F71 variations are most important for the unique function of PYL13. As a result of these modifications, the mutant PYL9 and PYL11 cannot antagonize the ability of the PP2C enzyme (ABI1) to inhibit the ABA-dependent induction of RD29B-LUC expression in protoplasts. In other words, introducing the variations from the PYL13 protein into PYL9 and PYL11 caused the modified PYL9 and PYL11 proteins to act in a similar manner to PYL13. The ABA signaling pathway was reconstituted by co-expression of PYLs, ABI1, SnRK2.6, and ABF2. Wild-type (Col-0) protoplasts were used. RD29B-LUC was used as the ABA-responsive reporter. ZmUBQ-GUS was used as the internal control. After transfection, protoplasts were incubated for 4.5 h under light in the absence of ABA (open bars) or in the presence of 5 μM ABA (closed bars). Error bars indicate s.e.m. (n=3).

Figure 14:
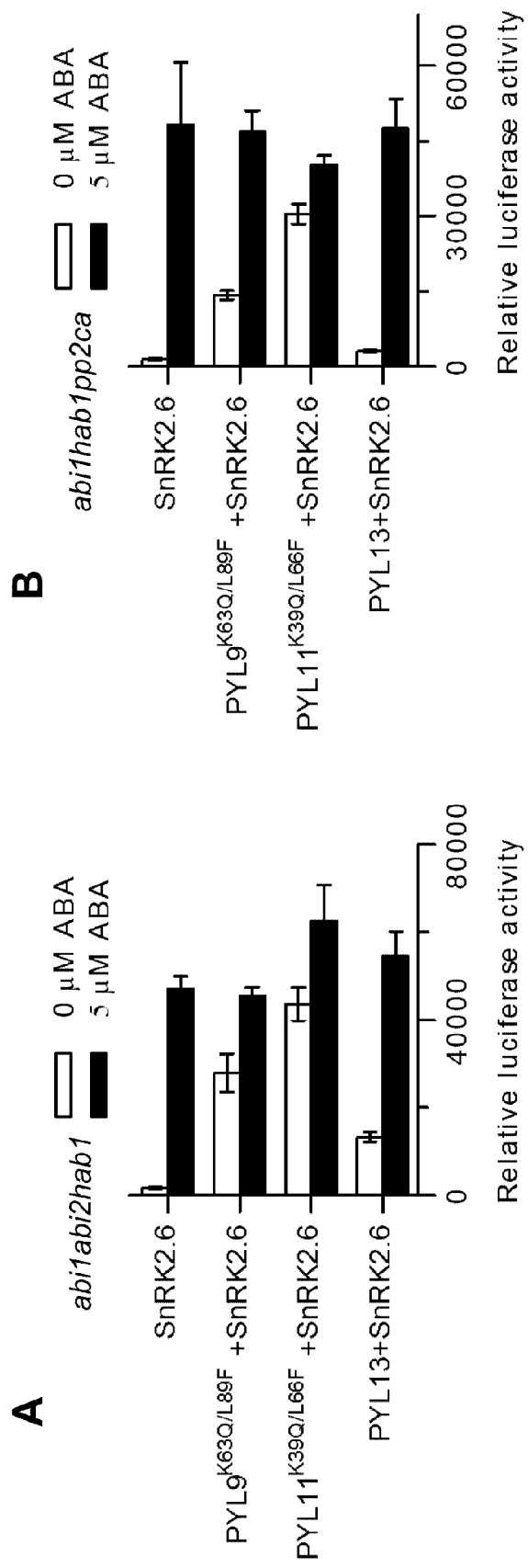

FIG. 14 shows the ABA-independent induction of RD29B-LUC in abi1/abi2/hab1 (A) and abihab1pp2ca (B) triple mutant protoplasts that transiently expressed PYL9 mutants, PYL11 mutants, PYL13, and SnRK2.6. As shown in FIG. 14, To test whether these two PYL mutants can mimic PYL13 to function on ABA-independent selective inhibition of PP2Cs, we co-expressed these two PYL mutants with SnRK2.6 and ABF2 in abi1/hab1/abi2 and abi1hab1pp2ca triple mutant protoplasts. Expression of RD29B-LUC in the absence of ABA was increased in the transfections of PYL9-K63Q/L89F or PYL11-K39Q/L66F together with SnRK2.6 and ABF2 to a considerable level. The ABA-independent RD29B-LUC expression is about 70% of that in the presence of 5 μM ABA in the transfection of PYL11-K39Q/L66F, while about 30~60% in the transfection of PYL9-K63Q/L89F (FIG. 4). These data confirmed that the two amino acid variations Q38 and F71 are responsible for the ABA-independent selectively inhibition of PP2Cs by PYL13. It must be noticed that the ABA-independent induction of RD29B-LUC expression by PYL9-K63Q/L89F and PYL11-K39Q/L66F are even better than PYL13, indicated that the overexpression of PYL9-K63Q/L89F and PYL11-K39Q/L66F may function better than that of PYL13 on drought tolerance in transgenic plants. RD29B-LUC was used as the ABA-responsive reporter. ZmUBQ-GUS was used as the internal control. After transfection, protoplasts were incubated for 4.5 h under light in the absence of ABA (open bars) or in the presence of 5 μM ABA (closed bars). Error bars indicate s.e.m. (n=4).

In an embodiment, a method of producing a transgenic plant with increased drought tolerance as compared to a control plant is provided. In some embodiments, the method includes inserting a gene encoding a PYL protein into a construct, introducing the construct into a cell to yield a transformed cell, generating a transgenic plant using the transformed cell, and growing the transgenic plant. In some embodiments, the PYL protein is a PYL13 protein. In some embodiments, the PYL protein is another PYL protein, e.g., PYL9 or PYL11, modified with point mutations analogous to one or more of the variations identified in PYL13, e.g., Q38K, F71L, and T135N. In an embodiment, the position of the position of the point mutation is identified via sequence alignment. In an embodiment, the transgenic plant comprises overexpression of the PYL protein. In some embodiments, the transgenic plant exhibits increased drought tolerance as compared to the control plant. In some embodiments, the PYL genes originate from *Arabidopsis*. In some embodiments, the PYL13 protein is SEQ ID NO: 1. In some embodiments, the PYL proteins are selected from the group consisting of SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, and SEQ ID NO: 161, which are then modified with one or more of the variations identified in PYL13 based on sequence alignment.

In some embodiments, the native PYL proteins are modified in a target plant. For example, a homologous protein has been identified in rice. Modifying other PYL proteins in the same family in rice and/or overexpressing the PYL13 homology may result in increased drought and/or stress tolerance.

In some embodiments, the transgenic plant exhibits increased drought tolerance in the form of increased survival under drought stress as compared to the control plant. The control plant can be a wild-type plant, a calibrator transgenic line (a transgenic line that does not express the transgenic gene), or any other plant suitable for the purpose of comparison.

In one embodiment, the insertion of the PYL13 gene results in transgenic plants having at least one of decreased transpiration rate, decreased stomatal conductance, increased photosynthetic rate, and increased water use efficiency compared to a control plant.

In a further embodiment, the insertion of the PYL13 gene in transgenic plants results in accelerated stress responsive gene expression compared to a control plant.

In another embodiment, a transgenic plant containing a polynucleotide encoding for the polypeptide comprising: (a) SEQ ID NO: 1 (b) the full-length complement of SEQ ID NO: 1 (c) the reverse full-length complement of SEQ ID NO: 1 or (d) the reverse full-length sequence of SEQ ID NO: 1 is provided.

In another embodiment, the present invention comprises a transgenic plant comprising any portion of a polynucleotide encoding for the polypeptide comprising SEQ ID NO: 1 and having increased drought tolerance.

In one example, the PYL13 gene was inserted under the control of the constitutive cauliflower mosaic virus 35S promoter. Over-expression of PYL13 results in plants with increased drought tolerance than the corresponding non-transgenic control plants.

Although this description mainly refers to using embodiments of the invention in conjunction with the PYL13 gene, it should be appreciated that these embodiments may be used to insert other PYL genes modified in accordance with the disclosure herein, e.g., with point mutations, into plants for modulating or altering drought tolerance.

Specific embodiments of the invention are described herein. Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments and combinations of embodiments are intended to be included within the scope of the appended claims. Although specific terms are employed herein, they are used in a generic and descriptive sense only and not for purposes of limitation.

The disclosure will be further explained with reference to the following examples, which provide exemplary methods and products associated with the transgenic plants disclosed herein.

EXAMPLES

Plant Materials

Arabidopsis thaliana Col-0 was used as the wild type (WT).

The PYL13 cDNA coding region (SEQ ID NO: 1) was amplified by RT-PCR using the gene-specific primers PYL13 CDSF (SEQ ID NO: 2) and PYL13 CDSR (SEQ ID NO: 3). The amplicon was cloned into the EcoRI and SalI sites of the binary vector pCAMBIA99-1 and confirmed by sequencing.

To generate the ProPYL13: PYL13-HA-YFP construct, the 2.79-kb PYL13 promoter fragment amplified from Col-0 genomic DNA with the primers ProPYL13F (SEQ ID NO: 4) and PYL13R (SEQ ID NO: 5) was cloned into the SalI and BamHI sites of the modified pSAT vector with YFP and 3HA tags at the C-terminal. The coding region of PYL13 from pCAMBIA99-1-PYL13 was then subcloned between the PYL13 promoter and the YFP coding sequence, for example SEQ ID NO: 148. The whole insertion cassette was digested with PI-Psp1 and re-inserted into pRCS2-htp binary plasmids.

The resultant plasmids were transformed into Col-0 as mediated by Agrobacterium tumefaciens GV3101, although other methods of transforming plasmids into plants may be used as is known in the art. All transgenic plants were verified by PCR and Northern blot assays. The T3 generation was used for further experiments.

Plasmid Constructs

ZmUBQ::GUS was provided by J. Sheen. RD29B::LUC, ABF2-haemagglutinin (HA), SnRK2.6-Flag, and His-PYLs were the same as reported as reported by Fujii et al. (2009). ABF2 was replaced with ABI1, ABI2, HAB1, HAB2, AHG1, PP2CA, HAI1, HAI2, and HAI3 using transfer PCR with pHBT-PP2CA forward (SEQ ID NO: 72) and reverse (SEQ ID NO: 73) primers. PYR1 was replaced with PYL13 using transfer PCR with pHBT95-PYL13 forward (SEQ ID NO: 6) and reverse (SEQ ID NO: 7) primers. The pHBT-His-PYL13 plasmid was used for mutagenesis with the QuikChange procedure (STRATAGENE) with specific primers. For example, the Q38K mutant in FIG. 1B was generated using the pHBT95-Q38K forward (SEQ ID NO: 8) and reverse primers (SEQ ID NO: 9). All plasmids were confirmed by sequencing.

PP2CA, ABI1, ABI2, AHG1, PYL13, and PYL2 were cloned into the pGEX-6P-1 vector between BamHI and EcoRI sites using transfer PCR with pGEX-PP2Cs or pGEX-PYLs primers. For example, ABI2 was cloned into the pGEX-6P1 vector using the pHBT-ABI1 forward (SEQ ID NO: 66) and reverse (SEQ ID NO: 67) primer.

FIGS. 11A and 11B provides the sequences for the forward and reverse primers used in plasmid construction.

Transient Expression Assay in Arabidopsis

Assays for transient expression in protoplasts were performed as described (Fujii et al., 2009). Leaf strips (0.5 mm) were cut from the middle part of second leaves using a razor blade (VWR SCIENTIFIC) and submerged in 15 mL of enzyme solution containing 20 mM MES, pH 5.7, 1.5% (w/v) cellulase R10 (YAKULT PHARMACEUTICAL INDUSTRY), 0.4% (w/v) macerozyme R10 (YAKULT PHARMACEUTICAL INDUSTRY), 0.4 M mannitol, 20 mM KCl, 10 mM $CaCl_2$, 1 mM 2-mercaptoethanol, and 0.1% BSA. The leaves were vacuum infiltrated for 30 min and then incubated without shaking for 3 h in the dark at room temperature. The enzyme/protoplast solution was diluted with 15 mL of W5 solution (2 mM MES, pH 5.7, 154 mM NaCl, 125 mM $CaCl_2$, and 5 mM KCl) and filtered with a 75-μm nylon mesh. Protoplasts were centrifuged at 100 g for 2 min in a 30-mL round-bottomed tube (SARSTEDT), resuspended in W5 solution, and rested for 30 min at room temperature.

Before transfection, protoplasts were changed into MMg solution (4 mM MES, pH 5.7, 0.4 M mannitol, and 15 mM $MgCl_2$) to a final concentration of 2×105 cells per microliter. Protoplasts (100 μl) were gently and thoroughly mixed with the plasmid DNA mixture (less than 10 μl) and 110 μl of PEG solution (40% w/v PEG-4000, 0.2 M mannitol, and 100 mM $CaCl_2$), incubated for 5 min, washed with 440 μl of W5 solution, and resuspended in 50 μl of WI solution (4 mM MES, pH 5.7, 0.5 M mannitol, and 20 mM KCl). After transfection, protoplasts were incubated in WI solution without ABA or with 5 μM ABA under light. The protoplasts were harvested after 4.5 h, frozen in liquid N2, and stored at −80° C.

The frozen protoplasts were resuspended in 50 μl of protoplast lysis buffer containing 2.5 mM Tris-phosphate, pH 7.8, 1 mM DTT, 2 mM DACTAA, 10% (v/v) glycerol, and 1% (v/v) Triton X-100. Protoplast lysates (20 μl) were mixed with 100 μl of LUC mix (PROMEGA), and LUC luminescence was measured with a plate reader (Wallac VICTOR2 plate reader).

Protoplast lysates (2 μl) were mixed with 10 μl of 4-methylumbelliferyl β-D-glucuronide (MUG) substrate mix (10 mM Tris-HCl, pH 8, 1 mM MUG [GOLD BIOTECHNOLOGY], and 2 mM $MgCl_2$). After the mixture was kept for 30 min at 37° C., 100 μl of 0.2 M $Na_2CO_3$ was added, and GUS activity was measured using the plate reader with the excitation filter at 355 nm and the emission filter at 460 nm.

All the plasmids used in this assay were purified with the QIAGEN Plasmid Maxi Kit or the QIAGEN Plasmid Midi Kit. The quality of plasmid DNA is important for high transfection efficiency. RD29B::LUC (7 μg of plasmid per transfection) was used as the ABA-responsive reporter. ZmUBQ::GUS (2 μg of plasmid per transfection) was used as the internal control. ABF2-HA, SnRK2.6-Flag, PP2Cs-HA (except ABI1), and His-PYLs were used at 3 μg per transfection. ABI1-HA was used at 2 μg per transfection. His-PYL13 was used at 6 μg per transfection when 2×PYL13 was needed and at 12 μg per transfection when 4×PYL13 was needed.

LUC Complementation Assay cLUC and nLUC were PCR amplified from pCAMBIA-NLuc and pCAMBIA-CLuc and cloned into pHBT95 to form pHBT95-nLUC and pHBT95-cLUC using transfer PCR with pHBT-nLUC forward (SEQ ID NO: 100) and reverse (SEQ ID NO: 101) and pHBT95-cLUC forward (SEQ ID NO: 102) and reverse (SEQ ID NO: 104) primers, respectively. PYR1, PYL1-PYL11, and PYL13 were amplified and cloned into pHBT-nLUC, and PYL13 was cloned into pHBT-cLUC between BamHI and SalI using PYL primers. For example, nLUC-PYR1 forward (SEQ ID NO: 104) and reverse (SEQ ID NO: 105) primers were used to amplify and clone PYR1 into pHBT-nLUC. All plasmids were confirmed by sequencing.

All plasmids used in this assay were purified with the QIAGEN Plasmid Maxi Kit or the QIAGEN Plasmid Midi Kit. A 5-μg quantity of purified plasmid was used per transfection. Protoplasts were incubated overnight in WI buffer containing 1% LUC mix (PROMEGA). The LUC luminescence of live protoplasts was measured in 96-well plates with a plate reader (Wallac VICTOR2 plate reader).

Drought-Stress Treatments

Seeds of the WT and OE-PYL13 lines were collected from plants subjected to the same growth conditions and periods. The seeds were imbibed at 4° C. for four days in the dark and planted directly in soil. Plants were grown in a growth room at 22/18° C. under a 14-h light/10-h dark photoperiod with a light intensity of 100 mmoles photons $m^{-2}$ $s^{-1}$. At seven days after sowing (DAS), each pot was thinned to eight seedlings of uniform size. At 14 DAS, the drought-stress treatment was initiated by withholding water for 24 days, after which time most WT plants had died. The plants were watered after 24 days of drought, and the surviving plants were counted two days later. The pots were rotated in the growth chamber every day to minimize the effect of environment. The complete experiment was repeated three times, each time with at least 3 replicates and at least 3 pots per replicate.

Measurement of Photosynthesis Parameters and Water Loss

Plants used for photosynthesis and water-loss assays were grown under short-day conditions (10-h light/14-h dark). After five days of drought treatment as described in the previous section, photosynthesis parameters were measured. Maximal rates of stomatal conductance, transpiration, and photosynthesis were measured with an infrared gas analyzer (6400, LI-COR, Lincoln, Nebr., USA), and water-use efficiency was calculated. After photosynthetic measurements, leaf area was measured with a portable area meter (3000A, LI-COR). The leaves were then dried for 48 h at 65° C. and weighed. For water-loss determination, whole rosettes of 18-day-old plants were cut from the base and weighed at indicated time points.

Protein Purification and Pull-Down Assay

*Escherichia coli* strain BL21 (DE3.0) was used to express the glutathione S-transferase (GST)-tagged recombinant proteins. Protein expression was induced by 1 mM isopropyl β-D-thiogalactoside for 12 h at 22° C. GST-tagged proteins were purified from the soluble fraction using Glutathione Sepharose 4B (AMERSHAM) under native conditions according to the manufacturer's instructions. The GST tag was removed by PRESCISSION Protease at 4° C. overnight in PBS (137 mM NaCl, 10 mM Phosphate, 2.7 mM KCl, and pH 7.3) with 1 mM DTT. His-tagged proteins were purified from the soluble fraction using PREPEASE Histidine-tagged High Specificity Purification Resin (USB) under native conditions according to the manufacturer's protocol.

In the His-mediated pull-down assay, His-PYL13 and His-PYR1 (5 μg) were immobilized on PREPEASE Histidine-tagged High Specificity Purification Resin (USB) and incubated with PP2Cs (10 μg) with or without 200 μM ABA at room temperature for 20 min in 1 mL of binding buffer (PBS containing 0.1% (v/v) Triton X-100). The agarose was rinsed for four times with 1 mL of binding buffer with or without 200 μM ABA to remove unbound proteins, and the agarose was finally resuspended in 40 μl of 1×SDS loading buffer (50 mM Tris-HCl, pH 6.8, 2% SDS, 10% glycerol, 1% β-mercaptoethanol, 12.5 mM EDTA, 0.02% bromophenol blue) for 5 min at 100° C. A 10-μl volume of each suspension was resolved by SDS-PAGE and Coomassie blue staining.

Co-Immunoprecipitation Experiments in Protoplasts

PP2CA-HA, ABI1-HA, and MYC-PYL13 plasmids (20 μg each) were transiently expressed in wild-type (Col-0) protoplasts. After transfection, protoplasts were incubated in WI buffer under light at room temperature for 16.5 h. Protoplasts were treated with 10 μM ABA for 1.5 h before they were harvested, frozen in liquid N2, and stored at −80° C. The frozen protoplasts were resuspended in 1 ml of immunoprecipitation (IP) buffer containing 50 mM Tris-HCl, pH 7.4, 150 mM NaCl, 1 mM EDTA, 0.1% (v/v) Triton X-100, and 1× protease inhibitor cocktail (SIGMA) with or without 10 μM ABA and then centrifuged at 21000 g for 30 min at 4° C. The supernatant was used as input and was incubated for 4 h at 4° C. with 30 μl of monoclonal anti-HA-agarose antibody produced in mouse (SIGMA, A2095). The agarose was washed four times using IP buffer with or without 10 μM ABA and finally resuspended in 50 μl of 1×SDS loading buffer for 5 min at 100° C. Protein samples (8 μl each) were resolved by SDS-PAGE and were electrotransferred onto PVDF membranes (MILLIPORE). Membranes were blocked in blocking buffer (PBS containing 0.1% Tween 20 (PBS-T) and 5% skim milk) for 2 h at room temperature and incubated in blocking buffer containing 1:500 diluted anti-HA (SIGMA, SAB4300603) or 1:2000 diluted anti-c-MYC (ABCAM, ab9106) rabbit antibodies for 1 h at room temperature. After they were washed five times (5 min each) with PBS-T, membranes were incubated for 1 h in blocking buffer containing 1:5000 diluted and stabilized goat anti-rabbit HRP-conjugated antibodies (PIERCE, 32460). They were then washed five times with PBST and proteins were detected using Lumi-Light Western Blotting Substrate (ROCHE).

Phosphatase Activity Assay

Phosphatase activity was measured using the colorimetric substrate p-nitrophenyl phosphate (pNPP, SIGMA). Reactions were performed in a reaction buffer containing 50 mM Tris-HCl, pH 7.5, 25 mM $Mg(OAc)_2$, 2 mM $MnCl_2$, 0.5 mM EGTA, 0.5% β-mercaptoethanol, and 0.5% BSA. ABA and PYLs were added as indicated. The concentration of PP2Cs and PYLs was 0.3 μM. Reactions were initiated by the addition of pNPP to a final concentration of 50 mM. The hydrolysis of pNPP was measured by following the absorbance at 405 nM (A405). Because His-PYL13 is difficult to purify, is prone to degradation, and rapidly loses activity, newly purified PYL13 was used for the phosphatase activity assay.

Northern Blot and Real-Time PCR Assay

For Northern blot analysis, total RNA was isolated with the QIAGEN-RNeasy Mini Kit (QIAGEN, Valencia, Calif., USA) according to the manufacturer's instructions. Four microliters of RNA was loaded onto agarose gels containing formaldehyde, and the gels were run at 72 volts for 4 h. After electrophoresis was completed, all RNA samples were transferred to Hybond-N+ membrane by capillary transfer. Probes for the PYL13 gene (for verification of OE-PYL13 lines) and the YFP gene (for verification of Pro-PYL13-YFP-3HA transgenic lines) were labeled with the PCR-DIG probe synthesis kit (ROCHE, Nutley, N.J., USA) according to the manufacturer's instructions. The following primers were used for PCR reactions: PYL13 forward: 5'-ATG GAA AGT TCT AAG CAA AAA C-3' SEQ ID NO: 134; PYL13 reverse: 5'-TTA CTT CAT CAT TTT CTT TGT GAG-3' SEQ ID NO: 135; YFP forward: 5'-ACG TAA ACG GCC ACA AGT TCA-3' SEQ ID NO: 136; YFP reverse: 5'-ACT GGT AGC TCA GGT AGT GGT TGT-3' SEQ ID NO: 137. Pre-hybridization, hybridization, washes, and detection were performed using the DIG high primer DNA labeling and detection starter kit II (ROCHE, Nutley, N.J., USA) according to the manufacturer's instructions.

For real-time PCR assays, reactions were set up with iQ™ SYBR® Green Supermix (BIORAD, CA, USA). The CFX96 TOUCH™ Real-Time PCR Detection System was used to detect amplification levels and was programmed for an initial step at 95° C. for 2 min, followed by 40 cycles of 15 s at 95° C. and 1 min at 60° C. Quantification was performed with three independent experiments. Relative expression levels of target genes and SD values were calculated using the 2-ΔΔCT method. Primers used for real-time PCR are provided in the following Table:

| Gene | Forward Primers | Reverse Primers |
|---|---|---|
| RD29A | GCCGACGGGATTTGACG SEQ ID NO: 138 | GCCGGAAATTTATCCTCTTCTGA SEQ ID NO: 139 |
| RAB18 | TCGGTCGTTGTATTGTGCTTT TT SEQ ID NO: 140 | CCAGATGCTCATTACACACTCAT G SEQ ID NO: 141 |
| COR15A | AACGAGGCCACAAAGAAAGC SEQ ID NO: 142 | CAGCTTCTTTACCCAATGTATCT GC SEQ ID NO: XX143 |
| KIN1 | TCTCATCATCACTAACCAAAA C SEQ ID NO: 144 | GACCCGAATCGCTACTTG SEQ ID NO: 145 |
| ACTIN2 | CTAAGCTCTCAAGATCAAAGG C SEQ ID NO: 146 | AACATTGCAAAGAGTTTCAAGG SEQ ID NO: 147 |

Immunoprecipitation and Mass Spectrometer Assay

Proteins were extracted from Pro-PYL13-YFP-3HA transgenic lines and the Col WT with an extraction buffer containing 50 mM Tris-HCl, pH 7.5, 150 mM NaCl, 5 mM EDTA, 0.1% NP-40, 10% glycerol, 1 mM phenylmethylsulfonyl fluoride, 5 mM DTT, and one unit of Protease Inhibitor Cocktail (SIGMA-ALDRICH, CA, USA). Immunoprecipitation was performed with GFP polyclonal antibody (INVITROGEN, CA, USA). The protein complex was eluted from Protein A agarose beads with urea elution buffer (8 M Urea, 20 mM Tris-HCl, pH 7.5, and 100 mM NaCl). After in-gel digestion, the protein complex was identified using Q-TOF LC/MS/MS. MS/MS spectra were processed and queried against the NCBInr protein database using the MASCOT algorithm from Matrix Science Inc. for protein identification. Peptides were identified with a Δ mass value (observed mass−theoretical mass) less than ±1.0 D.

Sequence Comparison

PYL13 homologs were obtained from The *Arabidopsis* Information Resource (TAIR), DOE Joint Genome Institute (DOE JGI), and Phytozome. Protein sequences were aligned using CLUSTALX 2.0.5 (Larkin et al., 2007) with the default settings and were viewed using GENEDOC software.

The following PYL13 homologs were identified as having a sequence similarity E-value of <1e-90 to PYL13.

| Species | Protein ID | SEQ ID NO: | Gene Locus | Source Database |
|---|---|---|---|---|
| *Arabidopsis thaliana* | PYR1 | SEQ ID NO: 149 | AT4G17870 | The *Arabidopsis* Information Resource (TAIR) |
| *A. thaliana* | PYL1 | SEQ ID NO: 150 | AT5G46790 | TAIR |
| *A. thaliana* | PYL2 | SEQ ID NO: 151 | AT2G26040 | TAIR |
| *A. thaliana* | PYL3 | SEQ ID NO: 152 | AT1G73000 | TAIR |
| *A. thaliana* | PYL4 | SEQ ID NO: 153 | AT2G38310 | TAIR |
| *A. thaliana* | PYL5 | SEQ ID NO: 154 | AT5G05440 | TAIR |
| *A. thaliana* | PYL6 | SEQ ID NO: 155 | AT2G40330 | TAIR |
| *A. thaliana* | PYL7 | SEQ ID NO: 156 | AT4G01026 | TAIR |
| *A. thaliana* | PYL8 | SEQ ID NO: 157 | AT5G53160 | TAIR |
| *A. thaliana* | PYL9 | SEQ ID NO: 158 | AT1G01360 | TAIR |
| *A. thaliana* | PYL10 | SEQ ID NO: 159 | AT4G27920 | TAIR |
| *A. thaliana* | PYL11 | SEQ ID NO: 160 | AT5G45860 | TAIR |
| *A. thaliana* | PYL12 | SEQ ID NO: 161 | AT5G45870 | TAIR |
| *A. thaliana* | PYL13 | SEQ ID NO: 1 | AT4G18620 | TAIR |
| *A. lyrata* | AlPYR17 | SEQ ID NO: 162 | Aralyl|916866 | DOE Joint Genome Institute |
| *A. lyrata* | AlPYRL8 | SEQ ID NO: 163 | Aralyl|916865 | DOE Joint Genome Institute |
| *A. lyrata* | AlPYRL11 | SEQ ID NO: 164 | Aralyl|914817 | DOE Joint Genome Institute |
| *Glycine max* | GMPYRL19 | SEQ ID NO: 165 | Glyma15g08930.1 | Phytozome |
| *G. max* | GMPYRL20 | SEQ ID NO: 166 | Glyma13g30210.1 | Phytozome |

Homologous PYL Proteins in *Oryza sativa*

Researchers have identified the PYL13 homolog in rice, *Oryza sativa* (He et al., 2014). The researches characterize the PYL13 homolog as OsPYL12 and note that it abrogates the phosphatase activity of PP2Cs in the absence of ABA. The sequence alignment of OsPYL12 differs from the other PYL proteins of *O. sativa* at a glutamine residue (Q) where the other PYL proteins in *O. sativa* have a lysine (K). Similarly, the sequence alignment of OsPYL12 differs from the other PYL proteins of *O. sativa* at a phelyalanine residue (F) where the other PYL proteins have leucine (L). See FIG. 1 of He et al. In this manner, the Q38K and F71L variation is conserved in higher plants and indicates that transgenic plants across higher plants may be modified in the manner suggested herein to produce drought-tolerant varieties.

REFERENCES

Fujii H, Chinnusamy V, Rodrigues A, Rubio S, Antoni R, Park S Y, Cutler S R, Sheen J, Rodriguez P L, Zhu J K (2009) In vitro reconstitution of an abscisic acid signalling pathway. *Nature* 462: 660-664

Hao Q, Yin P, Li W, Wang L, Yan C, Lin Z, Wu J Z, Wang J, Yan S F, Yan N (2011) The molecular basis of ABA-independent inhibition of PP2Cs by a subclass of PYL proteins. *Mol Cell* 42: 662-672

He Y, Hao Q, Li W, Yan C, Yan N, Yin P (Apr. 17, 2014) Identification and characterization of ABA receptors in *Oryza sativa*. *PLOS ONE* 9:1-8

Hsieh T-H, Lee J-t, Charng Y-y, Chan M-T (2002) Tomato Plants Ectopically Expressing *Arabidopsis* CBF1 Show Enhanced Resistance to Water Deficit Stress. *Plant Physiology* 130: 618-626

Jaglo-Ottosen K R, Gilmour S J, Zarka D G, Schabenberger O, Thomashow M F (1998) *Arabidopsis* CBF1 overexpression induces COR genes and enhances freezing tolerance. *Science* 280: 104-106

Kuhn J M, Boisson-Dernier A, Dizon M B, Maktabi M H, Schroeder J I (2006) The protein phosphatase AtPP2CA negatively regulates abscisic acid signal transduction in *Arabidopsis*, and effects of abh1 on AtPP2CA mRNA. *Plant Physiol* 140: 127-139

Liu Q, Kasuga M, Sakuma Y, Abe H, Miura S, Yamaguchi-Shinozaki K, Shinozaki K (1998) Two transcription factors, DREB1 and DREB2, with an EREBP/AP2 DNA binding domain separate two cellular signal transduction pathways in drought- and low-temperature-responsive gene expression, respectively, in *Arabidopsis*. *Plant Cell* 10: 1391-1406

Ma Q, Dai X, Xu Y, Guo J, Liu Y, Chen N, Xiao J, Zhang D, Xu Z, Zhang X, Chong K (2009a) Enhanced tolerance to chilling stress in OsMYB3R-2 transgenic rice is mediated by alteration in cell cycle and ectopic expression of stress genes. *Plant Physiol* 150: 244-256

Ma Y, Szostkiewicz I, Korte A, Moes D, Yang Y, Christmann A, Grill E (2009b) Regulators of PP2C phosphatase activity function as abscisic acid sensors. *Science* 324: 1064-1068

Park S Y, Fung P, Nishimura N, Jensen D R, Fujii H, Zhao Y, Lumba S, Santiago J, Rodrigues A, Chow T F, Alfred S E, Bonetta D, Finkelstein R, Provart N J, Desveaux D, Rodriguez P L, McCourt P, Zhu J K, Schroeder J I, Volkman B F, Cutler S R (2009) Abscisic acid inhibits type 2C protein phosphatases via the PYR/PYL family of START proteins. *Science* 324: 1068-1071

Yin P, Fan H, Hao Q, Yuan X, Wu D, Pang Y, Yan C, Li W, Wang J, Yan N (2009) Structural insights into the mechanism of abscisic acid signaling by PYL proteins. *Nat Struct Mol Biol* 16: 1230-1236

What is claimed is:

1. A transgenic plant having increased drought tolerance compared to a control plant, wherein the transgenic plant is transformed with a recombinant DNA construct comprising a polynucleotide sequence that is expressed to obtain a drought tolerant plant, wherein the polynucleotide sequence has a sequence similarity of E value <1e-90 to PYL13, wherein PYL13 has an amino acid sequence consisting of SEQ ID NO:1 and comprising CL1, CL2 and CL4 conserved regions, wherein the polynucleotide sequence expresses a mutant polypeptide having an amino acid sequence selected from the group consisting of:

SEQ ID NO:149 having at least one homologous point mutation selected from the group consisting of K59Q, L87F and N151T, SEQ ID NO:150 having at least one homologous point mutation selected from the group consisting of K86Q, L114F and N181T, SEQ ID NO:151 having at least one homologous point mutation selected from the group consisting of K64Q, L91F and N157T, SEQ ID NO:152 having at least one homologous point mutation selected from the group consisting of K70Q, L111F and N180T, SEQ ID NO:153 having at least one homologous point mutation selected from the group consisting of K81Q, L109F and N170T, SEQ ID NO:154 having at least one homologous point mutation selected from the group consisting of K87Q, L115F and N176T, SEQ ID NO:155 having at least one homologous point mutation selected from the group consisting of K90Q, L118F and N184T, SEQ ID NO:156 having at least one homologous point mutation selected from the group consisting of K65Q, L91F and N155T, SEQ ID NO:157 having at least one homologous point mutation selected from the group consisting of K61Q, L87F and N151T, SEQ ID NO:158 having at least one homologous point mutation selected from the group consisting of K63Q, L89F and N153T, SEQ ID NO:159 having at least one homologous point mutation selected from the group consisting of K56Q, L83F and N147T, SEQ ID NO:160 having at least one homologous point mutation selected from the group consisting of K39Q, L66F and N129T, and SEQ ID NO:161 having at least one homologous point mutation selected from the group consisting of K39Q, L66F and N128T.

2. The transgenic plant of claim 1, wherein the mutant polypeptide is overexpressed as compared to a control plant.

3. The transgenic plant of claim 1, wherein the polynucleotide is operably linked to a promoter selected from the group consisting of a constitutive promoter, an inducible promoter, a tissue specific promoter, and a stress-responsive promoter.

4. The transgenic plant of claim 1, wherein the transgenic plant exhibits an increased survival rate after drought as compared to a control plant.

5. The transgenic plant of claim 1, wherein the transgenic plant comprises at least one characteristic selected from the group consisting of a decreased relative transpiration rate, a decreased relative stomatal conductance, an increased relative photosynthetic rate, and an increased relative water use efficiency as compared to a control plant.

6. The transgenic plant of claim 1, wherein the transgenic plant exhibits accelerated stress responsive gene expression of a stress gene selected from the group consisting of RD29A, KIN1, COR15A, and RAB18 as compared to a control plant.

7. A transgenic seed obtained from the transgenic plant of claim 1, and wherein the transgenic seed comprises said recombinant DNA construct.

8. A method of increasing drought tolerance of a plant as compared to a control plant, the method comprising:

(a) providing a recombinant DNA construct comprising a polynucleotide sequence that is expressed to obtain a drought tolerant plant, wherein the polynucleotide sequence has a sequence similarity of E value <1e-90 to PYL13, wherein PYL13 has an amino acid sequence consisting of SEQ ID NO:1 and comprising CL1, CL2 and CL4 conserved regions, wherein the polynucleotide sequence expresses a mutant polypeptide having an amino acid sequence selected from the group consisting of:

SEQ ID NO:149 having at least one homologous point mutation selected from the group consisting of K59Q, L87F and N151T, SEQ ID NO:150 having at least one homologous point mutation selected from the group consisting of K86Q, L114F and N181T, SEQ ID NO:151 having at least one homologous point mutation selected from the group consisting of K64Q, L91F and N157T, SEQ ID NO:152 having at least one homologous point mutation selected from the group consisting of K70Q, L111F and N180T, SEQ ID NO:153 having at least one homologous point mutation selected from the group consisting of K81Q, L109F and N170T, SEQ ID NO:154 having at least one homologous point mutation selected from the group consisting of K87Q, L115F and N176T, SEQ ID NO:155 having at least one homologous point mutation selected from the group consisting of K90Q, L118F and N184T, SEQ ID NO:156 having at least one homologous point mutation selected from the group consisting of K65Q, L91F and N155T, SEQ ID NO:157 having at least one homologous point mutation selected from the group consisting of K61Q, L87F and N151T, SEQ ID NO:158 having at least one homologous point mutation selected from the group consisting of K63Q, L89F and N153T, SEQ ID NO:159 having at least one homologous point mutation selected from the group consisting of K56Q, L83F and N147T, SEQ ID NO:160 having at least one homologous point mutation selected from the group consisting of K39Q, L66F and N129T, and SEQ ID NO:161 having at least one homologous point mutation selected from the group consisting of K39Q, L66F and N128T; and (b) introducing the recombinant DNA construct into a plant to produce a transgenic plant, wherein the transgenic plant exhibits increased drought tolerance.

9. The method of claim 8, wherein the mutant polypeptide is overexpressed as compared to a control plant.

10. The method of claim 8, wherein the polynucleotide sequence is operably linked to a promoter is selected from the group consisting of a constitutive promoter, an inducible promoter, a tissue specific promoter, and a stress-responsive promoter.

11. The method of claim 8, wherein the transgenic plant comprises at least one characteristic selected from the group consisting of a decreased relative transpiration rate, a decreased relative stomatal conductance, an increased relative photosynthetic rate, and an increased relative water use efficiency as compared to a control plant.

12. The method of claim 8, wherein the transgenic plant exhibits accelerated stress responsive gene expression of a stress gene selected from the group consisting of RD29A, KIN1, COR15A, and RAB18 as compared to a control plant.

13. The method of claim 8, further comprising crossing the transgenic plant with itself or crossing the transgenic plant with another plant to produce a transgenic seed.

* * * * *